United States Patent
Manautou et al.

(10) Patent No.: US 10,908,062 B2
(45) Date of Patent: Feb. 2, 2021

(54) AIRBORNE PARTICLE MONITOR

(71) Applicant: Scanit Technologies, Inc., Milpitas, CA (US)

(72) Inventors: Pedro Manautou, Milpitas, CA (US); Joel Kent, Fremont, CA (US); An-Chun Tien, San Jose, CA (US)

(73) Assignee: Scanit Technologies, Inc., Milpitas, CA (US)

( * ) Notice: Subject to any disclaimer, the term of this patent is extended or adjusted under 35 U.S.C. 154(b) by 0 days.

(21) Appl. No.: 16/408,355

(22) Filed: May 9, 2019

(65) Prior Publication Data
US 2019/0293539 A1    Sep. 26, 2019

Related U.S. Application Data

(63) Continuation of application No. 15/900,650, filed on Feb. 20, 2018, now Pat. No. 10,330,578, which is a (Continued)

(51) Int. Cl.
*G01N 15/06* (2006.01)
*G01N 15/14* (2006.01)
(Continued)

(52) U.S. Cl.
CPC ....... *G01N 15/0612* (2013.01); *G01N 1/2273* (2013.01); *G01N 15/0227* (2013.01); (Continued)

(58) Field of Classification Search
CPC .......... G01N 15/0227; G01N 15/0612; G01N 15/1434; G01N 15/1463; G01N 15/1475; (Continued)

(56) References Cited

U.S. PATENT DOCUMENTS

H188 H * 1/1987 Thomson ................ 378/44
7,532,314 B1 5/2009 Black et al.
(Continued)

FOREIGN PATENT DOCUMENTS

WO    WO2019210375    11/2019

OTHER PUBLICATIONS

U.S. Appl. No. 62/076,507, filed Nov. 7, 2014; Landon D. Bunderson et al.
(Continued)

*Primary Examiner* — Tri T Ton
(74) *Attorney, Agent, or Firm* — Staniford Tomita LLP

(57) ABSTRACT

An airborne particle collection system includes a monitoring device and a collection media. The monitoring device includes a housing having an air-intake slot, and a motor. The collection media includes an adhesive-coated tape contained within a removable cartridge inserted into the housing. The removable cartridge includes a particle intake zone, proximate to the air-intake slot, and through which the adhesive-coated tape is exposed to capture airborne particles passing through the air-intake slot, and an inspection zone at which the airborne particles captured at the intake zone are transported for optical imaging. The motor moves the airborne particles captured by the adhesive-coated tape from the particle intake zone to the inspection zone.

20 Claims, 43 Drawing Sheets

Related U.S. Application Data continuation of application No. 15/178,170, filed on Jun. 9, 2016, now Pat. No. 9,933,351, which is a continuation-in-part of application No. 15/061,883, filed on Mar. 4, 2016, now abandoned.

(60) Provisional application No. 62/129,571, filed on Mar. 6, 2015, provisional application No. 62/188,606, filed on Jul. 3, 2015, provisional application No. 62/173,280, filed on Jun. 9, 2015, provisional application No. 62/210,253, filed on Aug. 26, 2015.

(51) Int. Cl.
| | | |
|---|---|---|
| *G01N 33/49* | (2006.01) | |
| *G01N 35/00* | (2006.01) | |
| *G06K 9/00* | (2006.01) | |
| *G01N 1/22* | (2006.01) | |
| *G01N 15/02* | (2006.01) | |
| *G01N 1/24* | (2006.01) | |
| *G01N 15/00* | (2006.01) | |

(52) U.S. Cl.
CPC ..... *G01N 15/1434* (2013.01); *G01N 15/1463* (2013.01); *G01N 15/1475* (2013.01); *G01N 33/4925* (2013.01); *G01N 35/00871* (2013.01); *G06K 9/00134* (2013.01); *G01N 2001/2276* (2013.01); *G01N 2001/245* (2013.01); *G01N 2015/0065* (2013.01); *G01N 2015/1465* (2013.01); *G01N 2015/1486* (2013.01); *G01N 2015/1493* (2013.01); *G01N 2015/1497* (2013.01); *G01N 2035/009* (2013.01); *G01N 2035/00881* (2013.01)

(58) Field of Classification Search
CPC ......... G01N 1/2273; G01N 2001/2276; G01N 2001/245; G01N 33/4925; G01N 35/00871; G01N 1/2214; G01N 2001/021; G01N 2001/2223; G01N 2015/0065; G01N 2015/1465; G01N 2015/1486; G01N 2015/1493; G01N 2015/1497; G01N 2035/00881; G01N 2035/009; G01N 21/84; G06K 9/00134
USPC .................................................. 356/335–343
See application file for complete search history.

(56) References Cited

U.S. PATENT DOCUMENTS

| | | | |
|---|---|---|---|
| 8,930,341 | B2 | 1/2015 | Amin et al. |
| 2013/0213945 | A1* | 8/2013 | Stegmann ............... H01J 37/00 219/121.83 |
| 2013/0319020 | A1* | 12/2013 | Neeld ..................... F25D 29/00 62/89 |
| 2018/0087919 | A1* | 3/2018 | Bertaux ............... G09B 29/007 |
| 2018/0284003 | A1* | 10/2018 | Lucas ................ G01N 15/0612 |
| 2019/0066288 | A1* | 2/2019 | Dudzik ............. G01N 21/9018 |

OTHER PUBLICATIONS

Anatharam et al. "Knowledge-driven Personalized Contextual mHealth Service for Asthma Management in Children". Mobile Services (MS), 2015 IEEE International Conference on Mobile Services Jun. 2015, pp. 284-291 (2015).

Platts-Mills, "Local Production of IgG, IgA, and IgE Antibodies in Grass Pollen Hay Fever". The Journal of Immunology 1979, 122, pp. 2218-2225 (1979).

\* cited by examiner

3700  Particle Information Packet Contents

| 3710 | Packet header | 3712 | Particle ID number |
| --- | --- | --- | --- |
|  |  | 3714 | Pointers to packet information |
| 3720 | Particle ID block | 3721 | Time stamp |
|  |  | 3722 | Particle collection device serial number |
|  |  | 3723 | Device GPS coordinates |
|  |  | 3724 | Adhesive-coated tape reel # |
|  |  | 3725 | X coordinate of particle (along length of tape) |
|  |  | 3726 | Y coordinate of particle (perpendicular to length of tape) |
| 3730 | Objectives block | 3732 | Application type |
|  |  | 3734 | definition of particles of interest |
| 3740 | Status block | 3742 | Completed-measurement status bit-coded status flag |
|  |  | 3744 | Completed-analysis status bit-coded status flag |
|  |  | 3746 | Work-in-progress particle classification |
|  |  | 3748 | Definitive particle classification |
| 3760 | Relationship block | 3762 | Sequence numbers of related particles |
|  |  | 3764 | Nature of relationship of related particles |
| 3780 | Data block | 3781 | In-situ - Camera sensor data |
|  |  | 3782 | In-situ - Alternate focus camera sensor data |
|  |  | 3783 | In-situ - Alternate illumination camera sensor data |
|  |  | 3784 | In-situ Alternate tape location camera sensor data |
|  |  | 3785 | Cloud-data - local weather conditions |
|  |  | 3786 | Could-data - Known seasonal allergens/pathogens |
|  |  | 3787 | Remote-viewing - Expert technician notes |
|  |  | 3788 | Remote-viewing - Expert scientist notes |
|  |  | 3789 | Archive - Microscope image data |
|  |  | 3790 | Archive - Bio-assay data |
|  |  | 3791 | Archive - Expert technician notes |
|  |  | 3792 | Archive - Expert scientist notes |

Figure 37

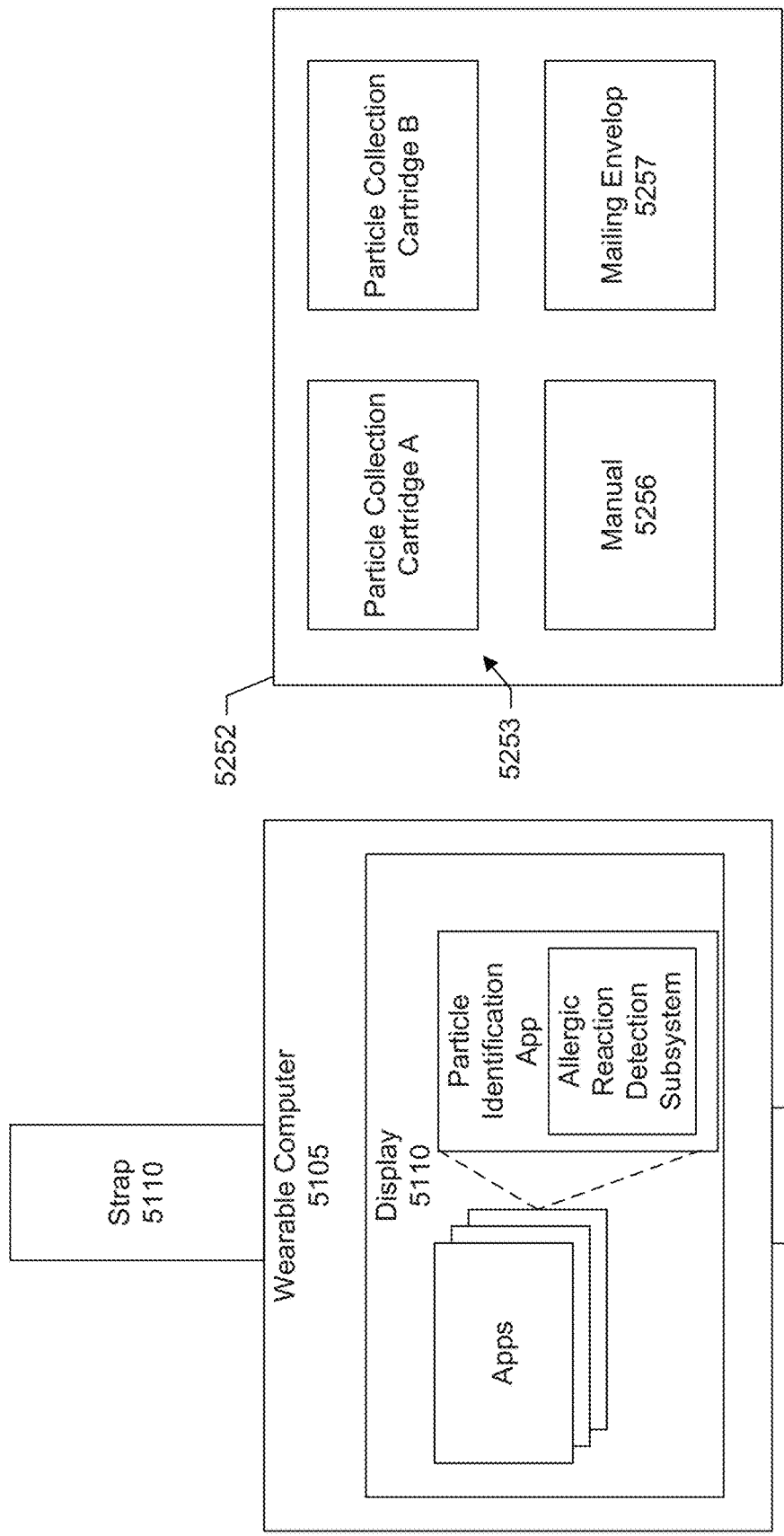

AIRBORNE PARTICLE MONITOR

CROSS-REFERENCE TO RELATED APPLICATIONS

This application is a continuation-in-part of U.S. patent application Ser. No. 15/061,883, filed Mar. 4, 2016, and of International Application PCT/US2016/021058, with an international filing date of Mar. 4, 2016, which claim priority to U.S. provisional patent applications 62/129,571 filed Mar. 6, 2015, and 62/188,606, filed Jul. 3, 2015 and claims the benefit of U.S. provisional patent applications 62/173,280, filed Jun. 9, 2015; and 62/210,253, filed Aug. 26, 2015. These applications along with other cited references in this application are incorporated by reference.

BACKGROUND

Monitoring air quality is of great importance in protecting against adverse health effects and also damage to farm crops such as vineyards. Indeed, there is an unmet need to provide individuals with personalized and actionable information regarding their exposure to allergens. Pollen exposure information may be considered actionable if it aids a user and associated health care providers in diagnosing the type of allergens inducing allergic reactions. Allergen exposure information is also actionable if it enables the user to better avoid allergen exposure. Information is also actionable information if it leads to more effective use of medication or therapy to reduce or eliminate allergic reactions and associated symptoms. One particularly important mechanism for allergen exposure is the inhalation of airborne allergens. Hence actionable information regarding airborne allergen exposure is of particular interest.

Airborne allergens include tree, grass and weed pollens, mold spores, cat or dog dander, as well as particulates associated with dust mites. Troublesome airborne allergens typically are sufficiently small to be easily transported some distance by air currents or wind before settling out of the air. Typically this means small particle sizes that are difficult to see with the naked eye. Airborne allergens are typically an invisible threat to an individuals' well-being.

Similarly, farms and vineyards can suffer from certain types of mold as winds can carry mold spores for many miles. Depending on climatic conditions, losses for vineyards may range from about 15 percent to about 40 percent or more of the harvest. The lost in harvest results in lost revenue, profit, and jobs. There is a need to cost-effectively and rapidly detect damaging mold spores so that control and mitigation measures can be quickly developed and deployed to save a harvest. Likewise, there remains an unmet need to provide individuals with personalized, prompt and actionable information regarding their exposure to allergens.

BRIEF SUMMARY OF THE INVENTION

An airborne biological particle monitoring device collects particles floating in air. The monitor includes a camera sensor, illumination source, and quantum-dot illumination source. The camera sensor captures at least a first image of the particles when the collected particles are illuminated by the illumination source. The camera sensor captures at least a second image of the particles when the collected particles are illuminated by the quantum-dot illumination source. The at least first and second images are analyzed to identify the collected particles.

The camera sensor may include a red-green-blue (RGB) camera sensor. In an embodiment, the quantum-dot illumination source includes a light emitting element; and a film, including quantum dots, and positioned to receive first light from the light emitting element and convert the first light into second light, where the second light illuminates the collected particles for the second image.

The light emitting element may include a light emitting diode (LED). The quantum-dot illumination source may include a light emitting diode (LED) having quantum dots.

In an embodiment, the quantum-dot illumination source includes a light emitting diode (LED); and a collection media that traps the particles, where the collection media comprises quantum dots, and is positioned to receive first light from the LED and convert the first light into second light, and where the second light illuminates the particles trapped by the collection media for the second image.

The collection media may include tape including a layer of adhesive, and a backing material upon which the layer of adhesive is placed, and where the quantum dots are within the layer of adhesive. The collection media may include tape including a layer of adhesive, and a backing material upon which the layer of adhesive is placed, and where the quantum dots are within the backing material.

In an embodiment, the quantum-dot illumination source includes a narrower emission spectra than the illumination source, the narrower emission spectra having a spectral peak with full-width-half-maximum less than 50 nanometers. In another specific embodiment, the narrower emission spectra comprises a spectral peak with full-width-half-maximum less than 25 nanometers. The full-width-half-maximum spectral width may be about 50, 40, 30, 25 nanometers, or less than 25 nanometers.

At least one of the illumination source or the quantum-dot illumination source may illuminate the collected particles with infrared light. At least one of the illumination source or the quantum-dot illuminate source may illuminate the collected particles with ultraviolet light. The illumination source may include a light emitting diode (LED) and the emitted first light by the LED may be white light.

The quantum-dot illumination source may include a light emitting diode (LED) emitting blue light, and a film including quantum-dots that receives the blue light, where the film converts the blue light into a narrow spectrum centered an absorption peak of chlorophyll-a as may be achieved via use of quantum dots that emit light at approximately 665 nanometers. The quantum-dot illumination source may include a light emitting diode (LED) emitting blue light, and a film comprising quantum-dots that receives the blue light, wherein the film converts the blue light into a narrow spectrum centered on an absorption peak of chlorophyll-a.

In an embodiment, the processor is adapted to identify a collected particle as being of a particular type of pollen by transmitting to a remote server a geographical location of the monitor, and obtaining from the remote server context information based on the geographical location of the monitor. The context information may include at least one of pollen types known to be currently blooming at the geographical location, wind patterns at the geographical location, or a listing of pollen types detected by other monitors.

The monitor may further include a battery, connected to and supplying power to the processor, camera sensor, illumination source, and quantum-dot illumination source. The monitor may further include a sensor, connected to the processor, to determine a current location of the pollen monitoring device; and a network interface controller, coupled to the processor, to receive over a network context information associated with the current location. The monitor may include a storage device storing a plurality of images of different types of particles, or parameters for algorithms that discriminate between different types of particles, or both. The quantum-dot illumination source may include size-tuned quantum dots, composition-tuned quantum dots, or both.

In an embodiment, there is a removable collection cartridge that includes a tape upon which the particles are trapped, and a tape guide that supports the tape, where at least a portion of the tape guide includes quantum-dots, the at least a portion of the tape guide thereby being the quantum-dot illumination source.

In another specific embodiment, a method for identifying airborne biological particles includes collecting the particles onto a collection media, illuminating the collected particles with first light, capturing a first image of the collected particles illuminated with the first light, illuminating the collected particles with second light, different from the first light, where the second light comprises light emitted from quantum dots, capturing a second image of the collected particles illuminated with the second light, and analyzing the first and second images to identify the collected particles.

In another specific embodiment, a method for identifying airborne biological particles includes collecting, by a particle monitor, the particles onto a collection media, illuminating, by the particle monitor, the collected particles with first light, capturing, by the particle monitor, a first image of the collected particles illuminated with the first light, illuminating, by the particle monitor, the collected particles with second light, different from the first light, where the second light comprises light emitted from quantum dots, capturing, by the particle monitor, a second image of the collected particles illuminated with the second light, analyzing, by the particle monitor, the first and second images to identify the collected particles, determining, by the particle monitor, that the particles cannot be satisfactorily identified from the analysis of the first and second image, and in response to the determination, issuing, by the particle monitor, a request to a server for context information associated with a geographical location of the particle monitor.

BRIEF DESCRIPTION OF THE FIGURES

FIG. 37 shows a block diagram of a particle information packet according to an embodiment.

FIG. 51 shows a block diagram of a wearable computer having a particle identification app installed.

FIG. 52 shows an example of a kit including particle collection cartridges.

DETAILED DESCRIPTION

Figure 1:
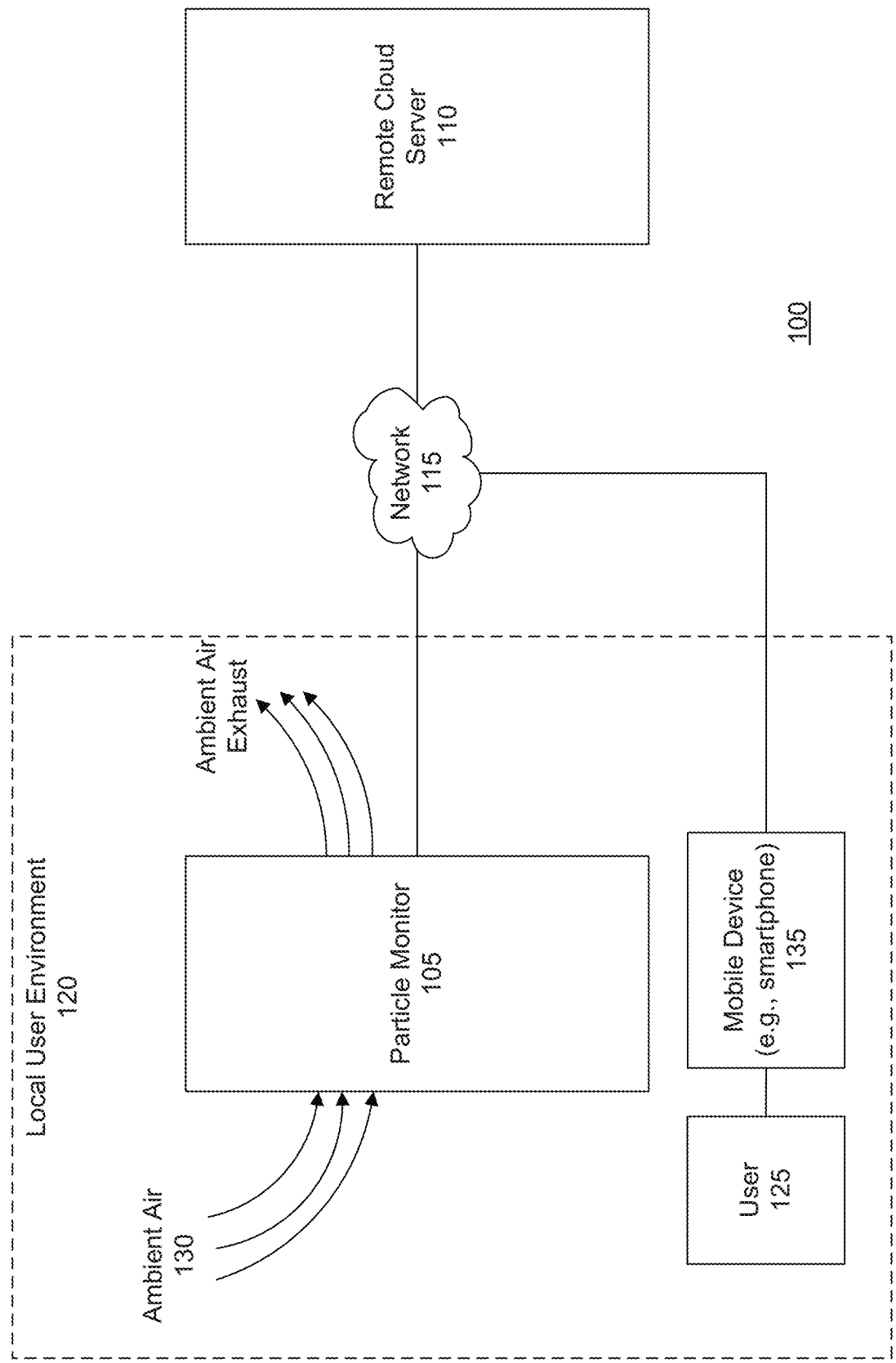
FIG. 1 shows a block diagram of an airborne particle monitoring system according to an embodiment.

FIG. 1 is a block diagram of an airborne particle collection, detection and recognition system 100 according to a specific embodiment. Such a system may address unmet needs of individuals or "users" or "consumers" for personalized and actionable information regarding their exposure to airborne particles such as pollen, mold, or other airborne particles. In a specific embodiment, airborne allergens of interest include tree, grass and weed pollens, mold spores, cat or dog dander, as well as particulates associated with dust mites. Botanically, "pollen" is essentially the plant version of sperm that serves to fertilize an egg, but by itself cannot grow into a plant. In contrast, a spore is self-contained in the sense that it has everything it needs to grow into mold or a plant. Monitoring of airborne allergenic particles is of particular interest to a large number of individuals as many people suffer from pollen allergies.

An airborne particle monitoring system as illustrated in FIG. 1 may also address needs related to monitoring of airborne agricultural pathogens as well as monitoring of air quality.

In the example shown in FIG. 1, the system includes a personal airborne particle monitoring device 105 and a remote cloud server 110 that is connected to the monitoring device via a communication network 115. The particle monitoring device may be referred to as a particle detector, pollen detector, particle collector, pollen monitor, pollen collection machine, or airborne biological particle monitoring device.

The monitoring device is a relatively small device or appliance that is designed to be placed in a local environment 120 of a user 125. For example, in a specific embodiment, the monitoring device is contained within a cylindrical housing having a diameter of about 100 millimeters (mm) and a height of about 150 mm. The relatively small size of the monitoring device allows the device to be placed unobtrusively in the user's home or office without occupying much space. The monitoring device may be deployed in an indoor environment or an outdoor environment (e.g., user's backyard).

The user may be a person who suffers from allergies. The system shown in FIG. 1 can be used to help identify the specific types of airborne particles that are responsible for the user's allergic reaction. With this information, a treatment plan can be developed to reduce or eliminate future allergenic reactions. In a specific embodiment, the monitoring device samples ambient air 130 and collects or traps airborne particles that may be present or floating in the ambient air.

The monitoring device can use a combination of techniques to analyze, discriminate, and identify the collected particles. In a specific embodiment, the analysis includes capturing images (e.g., pictures, photographs, or snapshots) of the particles under various lighting conditions and examining the captured images. Particles, including different types of pollen, can be identified or discriminated based on their morphology (e.g., shape, surface texture, apertures, or size), color, or combinations of these as may be captured by a camera sensor of the particle monitor.

More particularly, particles such as a various types of pollen can include light-absorbing molecules or tissues. When light strikes a particle some of the wavelengths may be absorbed while other wavelengths are reflected. The reflected wavelengths contribute to the color of the particle. For example, chlorophyll-a is generally found in plants. Chlorophyll-a absorbs blue and red light and reflects green light. In other words, plants are green because blue and red light are absorbed while green light is reflected.

In some cases, a particle of interest may have a very narrow spectral range in regards to what wavelengths are absorbed, what wavelengths are reflected, or both. Off-the-shelf components such as mass-produced lighting (e.g., light emitting diodes (LEDs)) and color camera sensors used in consumer-grade cameras are relatively inexpensive but generally do not provide the precision or sensitivity needed to accurately identify or discriminate the vast array of airborne particles that may be present in a user's local environment.

For example, a typical off-the-shelf red LED may emit wavelengths ranging from about 610 nanometers (nm) to about 760 nm. Different manufactures may each provide "red" LEDs, but the actual wavelengths emitted may vary greatly between the general range of 610 nm to 760 nm. While this range is acceptable for many different consumer products such as holiday lighting, vehicle dashboard displays, generic indicator lights, and so forth, such a wide range is not sufficient for discriminating between different types of airborne particles.

Much more color information could be provided by scientific-grade spectroscopy equipment. However, a major drawback of spectroscopy equipment is that such precision equipment is often large, bulky, and very expensive. Lasers, for example, are generally more expensive than LEDs and it can be very expensive to specify and manufacture an LED having a particular narrow emission spectra. Embodiments of the presently described particle monitor provide improvements in airborne particle identification or discrimination, and especially pollen identification, over known devices and techniques. Systems and techniques are provided for a particle monitor that is relatively inexpensive yet can quickly and accurately identify or discriminate different types of airborne particles. The faster airborne allergen exposure information is provided to the user, the more time the user has to take actions based on the information.

In a specific embodiment, quantum dots are used in the particle monitor to provide a narrow emission spectra. Quantum dots, as described in further detail below, are nanoscale particles of semiconducting material that can be embedded in various materials such as a polymer, plastic, glass, acrylic, silicone, adhesive, epoxy, or resin—just to name a few examples. A quantum dot can convert a wide range of incoming light into a precise emission spectra. The color of light emitted by a quantum dot can be precisely controlled based on the size of the quantum dot, composition, or both.

For example, bigger quantum dots (e.g., quantum dots with large diameters) emit longer wavelengths such as red, while smaller quantum dots (e.g., quantum dots with small diameters) emit shorter wavelengths such as green. The emission spectra emitted from the quantum dots can be precisely configured or tuned to correspond to or match the absorption characteristics of particles of interest (e.g., grass pollen, mold spores, and so forth).

As the emerging quantum-dot industry matures, it is anticipated that it will be much less expensive to produce quantum dots as compared to producing an LED (without quantum dots) having a particular narrow emission spectra. Quantum dots offer a level of control over the emission spectra that is very difficult and expensive to achieve with LEDs. In an embodiment, a particle monitor with quantum dots exploits the different absorption characteristics present in different particles. The collected particles are imaged, using an off-the-shelf color camera sensor, but under precise lighting conditions provided via the quantum dots and the collected particles are identified from the images.

In another specific embodiment, the analysis further includes combining the image analysis with context information that is obtained from the remote cloud server. The context information may include, for example, information regarding weather, wind conditions, humidity levels, the types of pollen currently blooming at the geographical location of the collected particles, vegetation known to be present at the geographical location of the collected particles, other context information, or combinations of these.

For example, in a specific embodiment, a particle monitoring device generates a set of candidate particle identifications for a particular particle that has been captured based on analyzing a set of images taken of the captured particle. After the set of candidate identifications have been generated, the particle monitoring device issues a request to the cloud server for context information. The request can include a geographical location of the particle monitoring device, time and date of particle capture, or both. The cloud server receives the request and uses the geographical location of the monitoring device, time and date of capture, or both to retrieve appropriate or relevant context information to transmit to the monitoring device.

The monitoring device receives the appropriate context information and further analyzes the context information in conjunction with the set of candidate particle identifications. Consider, as an example, that one of the candidate identifications is ragweed. If, however, the context information received by the particle monitor from the cloud server indicates that ragweed is currently not blooming at the geographical location of the pollen monitor, the analysis can include a process of elimination where ragweed is eliminated or excluded from the set of candidate particle identifications. This process of elimination can continue until a satisfactory identification has been made. The monitoring device may include a display (e.g., electronic display) which shows the type of airborne particle that has been identified.

The images of the particles captured by the monitoring device may be transmitted or sent to the remote cloud server for further analysis. The analysis may include a review of the images by a human technician. For example, in some cases, an image analysis and context information analysis may not lead to a satisfactory identification. In these cases, the analysis may be escalated to a human technician. In particular, the images, associated metadata, or both can be transmitted to the cloud server for review by a human technician. The associated metadata can include the geographical location of the particle monitor, time and date of particle capture, or both.

In a specific embodiment, the particle monitoring device traps the airborne particles on a piece of media or medium that can be removed by the user from the particle monitoring device. The media, with trapped airborne particles, may additionally be transported to a lab for an in-depth analysis. Consider, as an example, that the human technician is unable to identify with reasonable certainty the particle from the images. The technician can escalate the analysis to an analysis of the actual collected particle. In particular, the technician can notify the user that the collection media should be removed from the particle monitoring device and delivered to a laboratory for an analysis of the actual collected physical particles. For example, the technician may transmit through the system a notification to an app executing on the user's mobile device. The app may display the message, "Please remove particle collection media from your particle monitor and mail it to our laboratory for analysis."

This technique of escalation may be referred to as tiered particle analysis. Such an analysis helps to ensure judicious use of resources including computing resources (e.g., network bandwidth, storage) and human labor. Activities such as accessing a network, sending image files over the network, human review, mailing the physical particles, and so forth consume resources. For example, an image file may be several megabytes in size. It can be desirable to refrain from transmitting the image file over a network unless the transmission is deemed necessary.

In a specific embodiment, there is a first attempt to identify the collected particles where the first attempt is performed locally (e.g., at the particle monitor). If the first attempt fails to result in a satisfactory identification, a second attempt includes accessing a remote cloud server to obtain over a network context information. If the second attempt fails to result in the satisfactory identification, a third attempt includes transmitting over the network the image files to the remote cloud server for human review. If the third attempt fails to result in the satisfactory identification, a fourth attempt includes instructing the user to mail the removable media with collected particles to a laboratory.

In a specific embodiment, the particle monitoring device is paired with one or more mobile devices 135 associated with or belonging to the user. The pairing allows the particle monitoring device and mobile device to exchange information, instructions, data, commands, or other communications. Mobile devices include, for example, smartphones, tablet computers, and wearable computers (e.g., Apple Watch, Google Glass). The mobile device may include sensors such as a microphone, camera, accelerometer, gyroscope, global positioning system (GPS) sensor, other sensors, or combinations of these.

A sensor can be used to detect user motions, actions, sounds, or other physiological events that may indicate the user is currently suffering an allergic reaction (e.g., sneezing sound or coughing sound). The mobile device may include an allergic reaction detection application program or "app" that can determine from the signals generated from the sensors whether or not the user is suffering an allergic reaction. A determination that the user is suffering an allergic reaction can be communicated to the particle monitoring device. The particle monitoring device receives and logs the allergic reaction so that the allergic reaction can be cross-referenced to particles collected by the monitoring device. The cross-referencing helps to determine the particles that may be responsible for the user's allergic reaction. The monitoring device may further transmit results of the particle analysis (e.g., an identification of a particle) to the mobile device for display on the mobile device.

In another specific embodiment, the particle monitor itself may include an allergic reaction detection subsystem including one or more sensors (e.g., microphones) and logic in order to determine whether the user suffered an allergic reaction. Detecting allergic reactions is further described in U.S. patent application Ser. No. 15/061,883, filed Mar. 4, 2016, which is incorporated by reference along with all other references cited herein.

Figure 2:
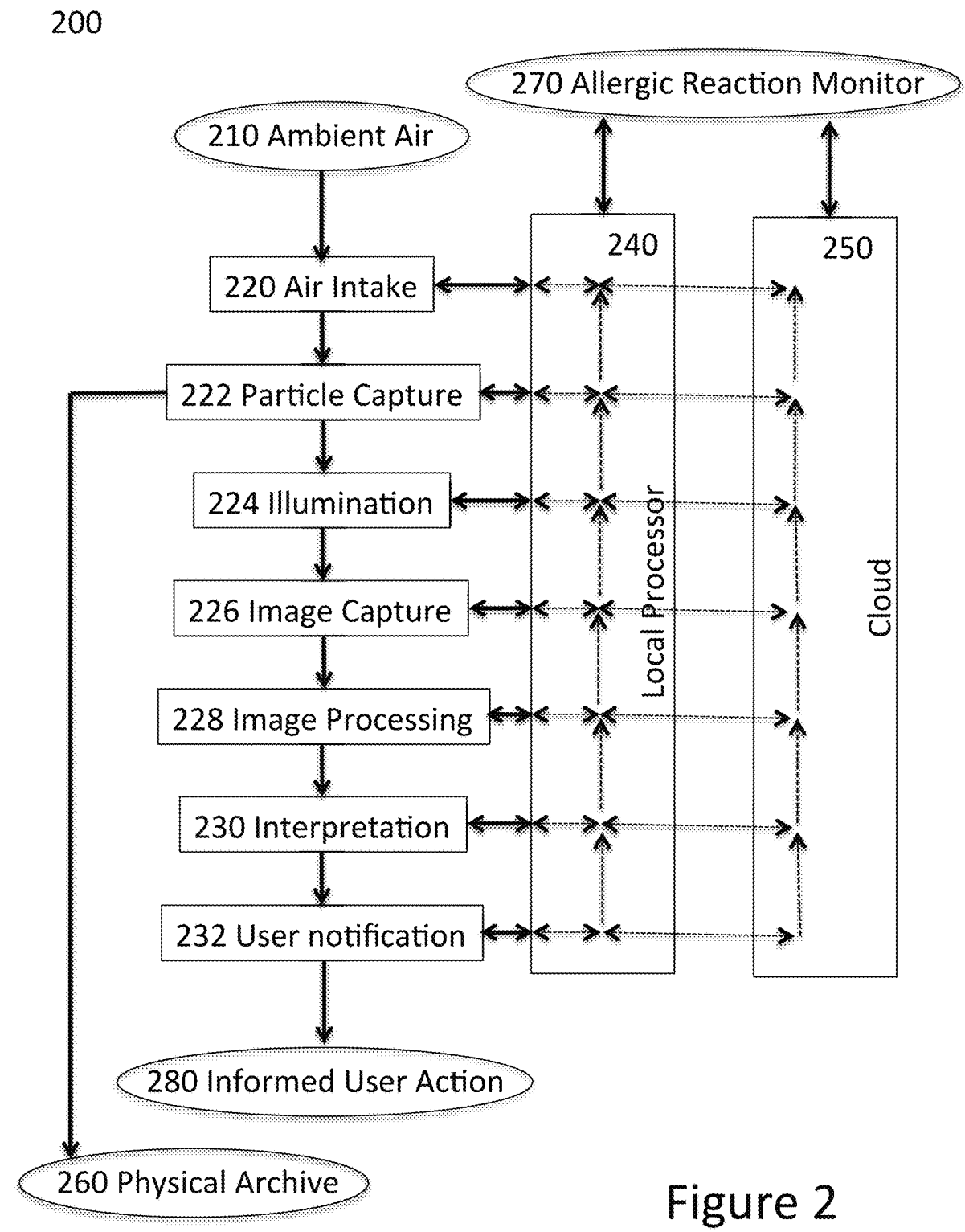
FIG. 2 shows another block diagram of an airborne particle monitoring system according to an embodiment.

FIG. 2 is a block diagram showing some elements and processes of an airborne particle collection, detection, and recognition system 200 according to a specific embodiment. Airborne particle monitoring system 200 includes air intake hardware 220 to sample ambient air 210, particle-capture hardware 222 with which particles removed from ambient are collected and transported for microscopic analysis. The microscope system includes illumination hardware 224 that shines visible, ultraviolet (UV), or infrared (IR) light, or combinations of these on captured particles, and image-capture hardware 226 that may include a lens assembly as well as a camera sensor. The light may include light emitted from quantum dots. Capturing various images of the particles when illuminated under different conditions provides for additional dimensions of analysis to help identify, classify, or discriminate between the collected particles.

Image processing software and hardware 228 processes image data from the image-capture hardware 226. The types of the observed particles are then decided by interpretation software 230. Finally, user-notification software 232 outputs the interpretation results in a form that can be understood by the user. For example, the output may include displaying on an electronic screen a message specifying the airborne particles that have been collected and identified. The value of airborne particle monitoring system 200 can be realized when it beneficially guides the user to take an informed user action 280.

In some embodiments, particle-capture hardware 222 provides for a medium that can be removed with captured particles and archived for possible future laboratory inspection, thus providing a physical archive 260 of captured particles.

The actions and data processing of airborne particle monitoring system 200 is orchestrated through a local processor 240. Local processor 240 is preferably supported by other computing and data resources via digital communication networks that may concisely be referred to as the "cloud"; see, e.g., cloud server of FIG. 1.

Local processor 240 and cloud 250 may support numerous feedback loops. Here is one example. Interpretation software 230 (which may be code executed in a dedicated processor, or by the local processor, or on the cloud) may be unable to reach a definitive result and the system may respond by requesting ultraviolet light illumination from the illumination hardware 224 in order to generate additional fluorescence spectral information.

Local processor 240 or cloud 250 may be in communication with an allergic reaction monitor 270 for the purpose of correlating pollen exposures with allergic reactions. The benefits possible by combining exposure and allergic reaction data is described in detail in U.S. patent application Ser. No. 15/061,883.

In an embodiment, the image capture hardware 226 is based on an imaging sensor designed for use in color cameras. The mass market for digital cameras, including those in smartphones, has resulted in very capable color camera sensors at relatively low prices. Such color camera sensors, such as the SON-IMX028 CMOS image sensor by Sony, provides at low cost rich data for particle detection and discrimination. Furthermore, the spectral richness of data collected with a color camera sensor may be extended by enhancing the capabilities of the illumination hardware 224; more details are given further below. The use of color camera sensors in combination with enhanced illumination hardware is advantageous for the goal of providing a capable airborne particle monitoring system 200 in a price range accessible to individual users.

The ability of airborne particle monitoring system 200 to generate actionable information is greatly enhanced by an aspect of user allergic reactions that will in this document be referred to as the "priming effect." There is much complexity to the physiological mechanisms by which the human immune system reacts to airborne allergenic particles. Fortunately, appreciation of the present system does not require a full detailed knowledge of the human immune system. Nevertheless, some understanding of immune system "sensitization" or "priming" effects is provided to fully appreciate the present system. Here we use "sensitization" and "priming" as synonyms for effects where allergen exposure at an earlier time affects the immune systems reaction to allergen exposure at a later time.

In particular, in some cases an allergen exposure at an earlier time does not directly lead to user suffering from allergy symptoms but may nevertheless "prime" or "sensitize" the immune system such that the user does suffer from allergy symptoms when exposed to allergens at a later time. More generally, if and how much a current exposure to airborne allergens "aggravate" allergic symptoms depends on the degree to which the user's immune system was sensitized or "primed" by past allergen exposures.

Before a user begins to suffer from allergic symptoms, it is particularly useful to have actionable information to know if and when one is being exposed to airborne allergens capable of priming one's immune system. Possible actions include avoiding further allergen exposure or proactively taking medications to reduce suffering from unavoidable further allergen exposure. The priming effect enables proactive responses to pollen exposure information.

In the medical literature, a distinction is sometimes made between "sensitization" and "priming effect" where the term "sensitization" is reserved for some types of physiological immune-system mechanisms and "priming effect" for other types of physiological immune-system mechanisms. Such distinctions can be important to the healthcare professional aiding a patient suffering from allergies. However, such distinctions are less important to the engineer designing hardware and software of airborne particle monitors. In this document, the terms "sensitization" and "priming" are used as synonyms.

Figure 3:
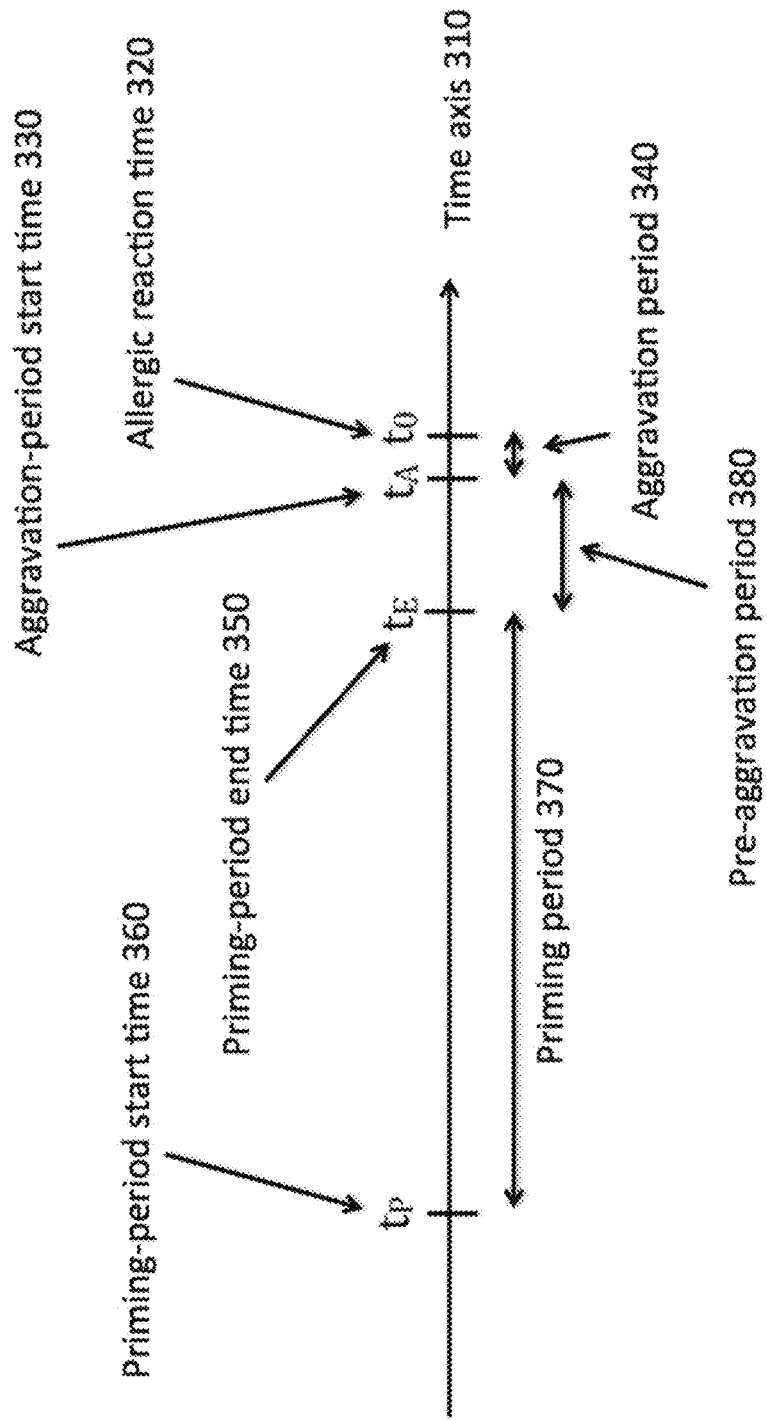
FIG. 3 shows an allergic reaction timing diagram.

Applicant has appreciated the role of the priming effect in identifying particles that may be responsible for a user's allergic reaction. FIG. 3 shows an allergic reaction timing diagram along a time axis 310. Let $t_0$ represent an allergic reaction time 320 at which a user starts suffering from an allergic reaction. The start of user suffering from an allergic reaction is likely to be due to what in medical science is known as "early phase" symptoms rather than "late phase" symptoms. This suggests considering immunoglobulin E (IgE) mediated immune system mechanisms as a specific example.

Immunoglobulin E are antibodies produced by the immune system. Generally, if a user has an allergy, the user's immune system overreacts to an allergen by producing antibodies called Immunoglobulin E. These antibodies travel to cells that release chemicals, causing an allergic reaction.

More particularly, the immediate cause of the allergic reaction may be the inhalation of an allergenic pollen or other airborne allergen that was recognized by immune cells armed with IgE anti-bodies specific to the inhaled allergen. These IgE-armed immune cells initiated a chain of physiological reactions resulting in symptoms experienced by the user. Allergens recognized by such IgE-armed immune cells may be referred to as "aggravating allergens," such as an "aggravating pollen." More generally, aggravating allergens are allergens that are the immediate cause of an allergic reaction.

Some time passes between the inhalation of the aggravating allergen and the resulting symptoms. Hence the allergic reaction starting at time $t_0$ must be due to exposure to the aggravating allergen sometime before time $t_0$. However, there is a limit to how long the onset of symptoms can be delayed with respect to the exposure. Let $t_A$ be the earliest time for which exposure to the aggravating allergen could lead to symptoms that do not occur until time $t_0$. The period of time between time $t_A$ and time $t_0$ may be referred to as the aggravation period 340. The aggravation period 340 is bounded by the aggravation-period start time 330 ($t_A$) and the allergic reaction time 320 ($t_0$).

In some cases, the duration of the aggravation period 340 is generally not precisely known and might vary with the type of allergen or vary from user to user. Nevertheless, it is clearly a time period very short compared to one day and long compared to a second. Medical science research has established reasonable estimates of the duration of aggravation period 340 to include the range from a few minutes to a half hour. For example, the aggravation period may range from about 2 minutes to about thirty minutes. This includes, for example, 5, 10, 15, 20, 25, 29, or more than 29 minutes. The aggravation period may be less than 2 minutes.

The allergic reaction described in the previous paragraph is most likely to occur if the user's immune system has been primed, that is, only if the user's body contains immune cells armed with IgE anti-bodies specific to the aggravating allergen. Such priming is the result of an earlier exposure to an allergen that is either the same as the aggravating allergen or is another allergen that cross-reacts with the aggravating allergen. The allergen that primes the immune system may be referred to as the "priming allergen." The priming allergen may or may not be the same as the aggravating allergen.

When a priming allergen is recognized by immune system memory cells, the memory cells cause the user's immune system to start manufacturing IgE anti-bodies specific to the priming allergen. Once manufactured, these IgE anti-bodies make their way to the immune cells and play a key role in the aggravation period 340. There is a time delay between user exposure to a priming allergen and the arming of immune cells with corresponding IgE anti-bodies.

As a result, there is a time after which it is too late for a priming allergen to have contributed to the chain of events leading to an allergic reaction at time $t_0$. Let $t_E$ represent this priming-period end 350. In some cases, it is not precisely known how far in the past the priming-period end 350 occurs, that is, the quantitative value of the time difference ($t_0 - t_E$) is not precisely known. The value may depend on both the allergen and the user. Nevertheless, it is clearly a time period very short compared to a week and long compared to an hour. Medical science research has established reasonable estimates for the time difference ($t_0 - t_E$) to include the range from 12 hours to 2 days. For example, the priming-period end time 350 may range from about 12 hours to about 2 days. This includes, for example, 15, 20, 25, 30, 35, 40, 45, or more than 45 hours. The pre-aggravation period may be less than 15 hours.

The priming effect is temporary. After exposure to priming allergens end, the corresponding priming effect fades with time. In biochemical terms, after exposure to priming allergens end, manufacture of priming-allergen specific IgE anti-bodies cease and eventually previously manufactured IgE anti-bodies degrade and disappear. As a result, there is a time before exposure to priming allergens that is too early to explain the primed state of the immune system at the allergic reaction time $t_0$. Let $t_P$ represent this time that may be referred to as the priming-period start time 360.

Exposure to priming allergens during the priming period 370, that starts with the priming-period start time 360 and ends with the priming-period end time 350, can explain the primed state of the user's immune system at allergic reaction time $t_0$ (or more precisely can explain the primed state of the user's immune system during the aggravation period 340). The duration of the priming period 370 is equal to ($t_E - t_P$). In some cases, it is not precisely known how long this priming period 370 is. The value may depend on both the allergen and the user. Nevertheless, it is clearly a time period short compared to a month and very long compared to a day. Medical science research has established reasonable estimates for the time difference ($t_E - t_P$) to include the range from one day to one month. For example, the priming period may range from about 3 hours to about 1 month. This includes, for example, 1, 2, 4, 6, 15, 20, or 30 days. The priming period may be less than 1 day.

The time period between the priming-period end time 350 and the aggravation-period start time $t_A$ may be referred to as the pre-aggravation period 380. Allergens inhaled by the user in this pre-aggravation period 380 are too late to be the priming allergen contributing an allergic reaction at time $t_0$ and too early to be the aggravation allergen contributing to an allergic reaction at time $t_0$. Lack of allergic reaction during the pre-aggravation period 380 provides evidence that any allergens inhaled during the pre-aggravation period 380, even if also present in the aggravation period 340, are not the guilty aggravating allergen. Allergens present in the aggravating period 340 but not present in the pre-aggravating period 380 are the prime suspects for aggravating allergens.

In some embodiments, the conclusion of the previous paragraph is tentative or preliminary and the user is prompted by the system to answer questions about medication. It is possible that the user had been taking medication that suppressed allergic reaction symptoms in the pre-aggravation period 380 and then the medication wore off during the aggravation period 340. In this scenario, allergens detected in the pre-aggravation period 380 remain candidates for being aggravating allergens.

FIG. 3 and the associated discussion above is idealized in the sense that transitions at priming-period start $t_P$, priming-period end $t_E$ and aggravation-period start $t_A$ are naïvely presented as sharp boundaries. This idealization is presented for purposes of clarity. In reality, the boundaries are fuzzy and the transitions are more gradual. For example, assuming a value the priming-period $t_P$ of two weeks, common sense tells us not to expect that an exposure to a priming allergen two weeks before allergic reaction time $t_0$ to be 100 percent effective while an exposure to a priming allergen two weeks and one minute before allergic reaction time $t_0$ to be totally ineffective.

In a specific embodiment, a sophisticated mathematical model is provided where the fading of the strength of the priming effect with increasing times into the past can be represented by a factor of $\exp\{-(t_0-t)/\tau\}$ where t is the time of priming allergen exposure and $\tau$ is an exponential time constant. However, for an understanding of the basic principles it is not necessary to delve into such mathematical details. Thus, it should be appreciated that FIG. 3 and associated discussion has been simplified for clarity of presentation and further mathematical refinement can be made without departing from the scope of the present disclosure.

The above discussion of FIG. 3 concerns the human immune system and considered inhaled allergens. When applying this science to particle collection machines, it should be kept in mind that allergen exposures that are measured by particle collection machines may provide imperfect estimates of exposures of the user to inhaled allergens.

To give a clear example where it is important to distinguish between measured allergen exposure and true allergen exposure, consider a user that places a pollen collection machine in a combined kitchen-living room, but sleeps in a well-separated bedroom. Furthermore, let us assume allergenic pollen from outdoors makes its way into the kitchen-living room but not the bedroom. After waking up from a good nights sleep, the user leaves the bedroom and enters the kitchen-living room, and then shortly thereafter has an allergic reaction at allergic reaction time 320.

In this case the user did not inhale the aggravating allergen until entering the kitchen-living room. The user was not exposed to the aggravating allergen in the pre-aggravation period 380. Nevertheless the pollen collection machine did measure the presence of the aggravating pollen in the pre-aggravation period 380. To correctly identify the aggravating allergen, one must allow the possibility that the aggravating allergen is detected during the pre-aggravation period 380 even if true exposure to an allergen in the pre-aggravation period is reason to eliminate the allergen as the aggravating allergen.

Figure 4:
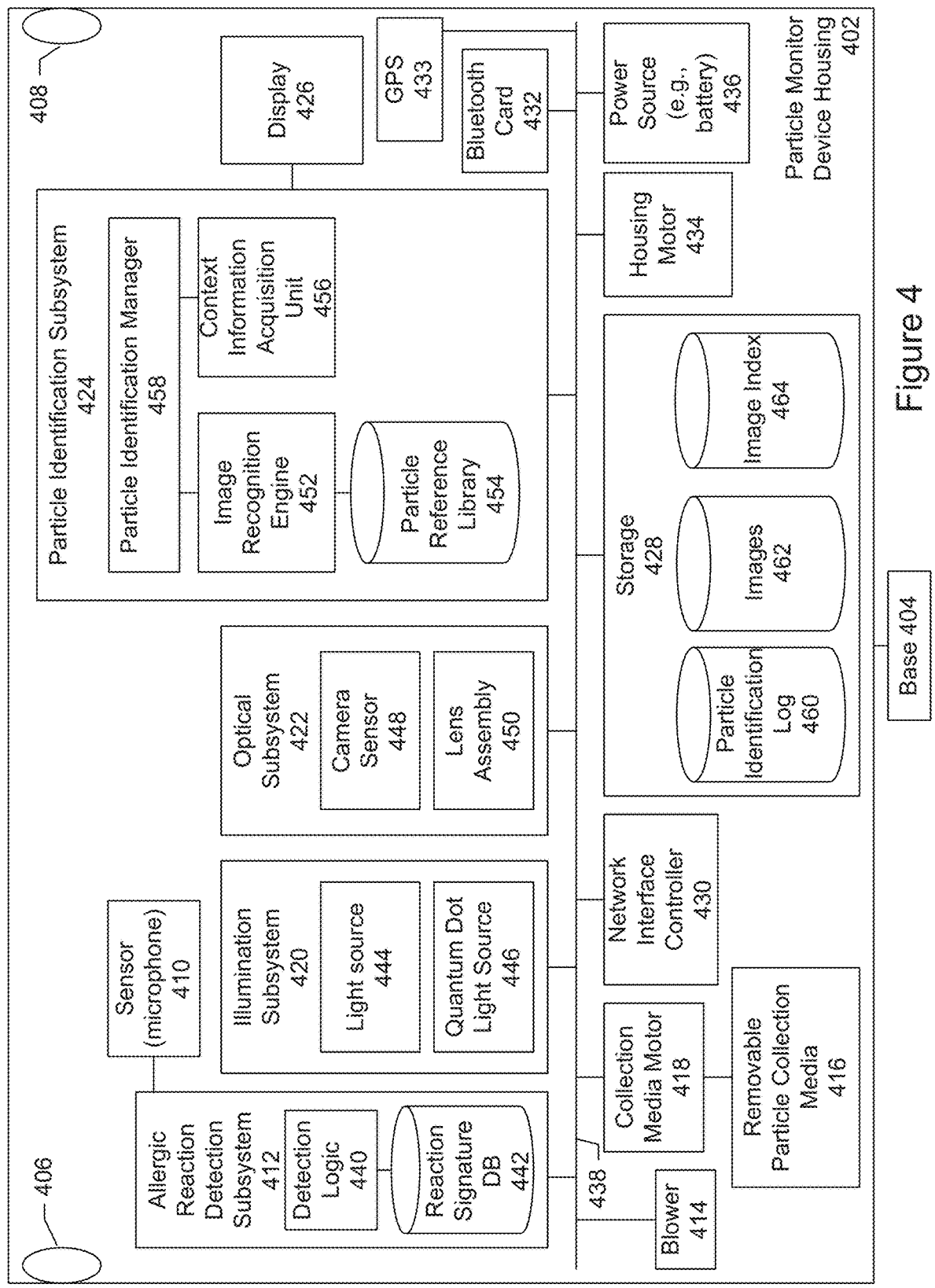
FIG. 4 shows a block diagram of an airborne particle monitor according to one embodiment.

FIG. 4 shows a block diagram of particle monitoring device 105 according to one embodiment. The block diagram shows a number of subsystems, processing modules, and components that can be included in the particle monitoring device. In an embodiment, the particle monitoring device includes quantum dots. The quantum dots are configured emit light having spectral characteristics corresponding to a particle of interest. Particles collected by the monitoring device are illuminated under the light emitted by the quantum dots and a color image (e.g., picture, photograph, or snapshot) is taken while the particles are illuminated by the quantum dots. The image can be analyzed to determine whether the image includes the particle of interest.

The particle monitoring device shown in FIG. 4 includes a device housing or enclosure 402 and a base 404, connected to the housing. The housing includes an air intake opening 406 and an air exhaust opening 408. Contained within or inside the housing is a sensor (e.g., microphone) 410 connected to an allergic reaction detection subsystem 412, blower 414, removable particle collection media 416, collection media motor 418, illumination subsystem 420, optical subsystem 422, particle identification subsystem 424, display 426 connected to the particle identification subsystem, storage 428, network interface controller 430, Bluetooth communication card 432, global positioning system (GPS) sensor 433, housing motor 434, and power source (e.g., battery) 436. There can be a user-operable power switch so that the device can be turned on, turned off, placed in a standby state, or combinations of these.

The subsystems, processing modules, components and so forth are connected by a bus system 438. The power source provides electrical power to the subsystems, processing modules, and components. The power can be DC power such as that provided by a battery. Using a battery to supply power facilitates a particle monitor that can be easily placed at any location such as in the user's home or office because the particle monitor does not have to be located near a wall outlet. The particle monitor may be placed in an outdoor environment such as the user's yard. A battery-operated device also facilitates the particle monitor being portable. The user can take the device with them when traveling and use the device in a hotel room. The battery may be a rechargeable battery or a disposable battery. A particle monitor may include a set of solar cells for recharging the battery. In another specific embodiment, the power can be AC power.

The sensor can be a microphone that detects sounds local to the monitoring device. Allergic reaction detection subsystem includes detection logic 440 and an allergic reaction signature database 442. The allergic reaction signature database stores information including characteristics indicative of an allergic reaction. The signatures can be information indicating coughing, sneezing, or both. The detection logic includes logic to receive a signal from the sensor, compare the signal to the information stored in the allergic reaction signature database, and determine whether the user is having an allergic reaction (e.g., user is coughing or sneezing).

The blower is responsible for moving ambient air outside the monitor device housing, through the air intake opening, into the monitor device housing, and then out through the air exhaust opening. The blower may be referred to a fan.

The removable particle collection media provides a medium for trapping particles that are airborne or floating in the ambient air. In a specific embodiment, the collection media includes an adhesive tape. The tape is flexible so that it can be mounted on or wound upon on a reel or spool. The adhesive tape includes a backing material and an adhesive that is applied to a side of the backing material. The backing material can be made of paper, plastic, plastic film, fabric, polyester, Teflon, nylon, cloth, metal foil, or any other competent material. The adhesive can be any type of adhesive that can trap particles floating in the ambient air. The adhesive may include glue, paste, mastic, rubber cement, or other sticky or tacky substance. The blower directs the flow of air towards or over the collection media. Particles within the air are then trapped by the adhesive-coated side of the tape.

In a specific embodiment, the tape is 3M polyester film tape 850 as provided by 3M Corporation Maplewood, Minn. Applicants have discovered that this particular tape includes features desirable for a particle monitor. In particular, the polyester film includes a wide temperature range resistance (e.g., −50 degrees Celsius to 177 degrees Celsius) which helps to reduce failure caused by film shrinkage or embrittlement. The wide temperature range resistance is desirable because in some embodiments, the monitor device is used outdoors and thus must survive wide temperature fluctuations throughout the day and times of the year. For example, temperatures typically drop during the night and rise during the day. Applicants have discovered that for applications of particle monitoring the tape shows desirable, long lasting cyclic fatigue. This means the tape can be pulled off and coiled again multiple times to re-examine trapped particles again and again and the tape still retains very good adhesion.

In a specific embodiment, the adhesive on the tape includes an acrylic adhesive. This is advantageous because it is not water-based and thus can better survive outdoor environments. For example, outdoor environments can be more subject to moisture as compared to indoor environments. An acrylic adhesive can tolerate moisture better than a water-based adhesive. In a specific embodiment, the tape includes a polyester film. Properties desirable in the polyester film—including its wide temperature range—is that it can be made very thin, possess very high strength, has high moisture resistance, and is resistant to chemicals and solvents (e.g., will not decompose easily if chemicals or solvents floating in the air should fall on the tape).

It should be appreciated that 3M polyester film tape 850 is merely one example of a tape suitable for use with the particle monitor and in other embodiments, other tapes with properties desirable for the particle monitor may instead be used. For example, 3M film tape 850 includes an adhesion to steel specification according to ASTM test method D-3330 of 31.5 N/100 mm). The collection media motor is designed with sufficient power to advance and uncoil the tape. Applicants have found that a lower adhesion to steel value can be desirable (e.g., about 15.7 N/100 mm) because less power is required to advance and uncoil the tape.

In a specific embodiment, a color of the tape is black or a dark color. An advantage of using black or a dark color is that light is less likely to reflect or bounce off the tape as compared to lighter colors (e.g., white). For example, a technique of the system includes capturing images of the particles under different specified illumination conditions. Light (e.g., white light) bouncing off the tape and into the camera sensor may skew the images and, in particular, the colors captured in the images. Particles may be examined using a technique referred to as all-angle. In another specific embodiment, the tape is transparent or at least partially transparent. A transparent tape allows for back-side illumination (e.g., illuminating from below the tape). In another specific embodiment, a tape upon which the particles are collected does not include an adhesive. In this specific embodiment, the tape includes an electrostatic surface. The tape may include, for example, a conducting film. The electrostatic surface attracts particles that come into close proximity to the tape. For example, if the particles are positively charged, the tape can be negatively charged.

In a specific embodiment, a removable cartridge is provided which houses the adhesive coated tape. The cartridge houses a supply reel, an uptake reel, and the adhesive coated tape. An end of the tape is connected to the supply reel. An opposite end of the tape is connected to the uptake reel. The adhesive coated tape is wound upon the supply reel and spent portions of the tape upon which particles have been trapped are wound onto the uptake reel. The cartridge may further include an identification tag such as a radio frequency identification tag (RFID) tag, machine readable code (e.g., barcode, quick response (QR) code), or other label. Depending upon the type of tag, the tag may be attached to a body of the cartridge (e.g., via glue), or printed onto the body of the cartridge. The particle monitor may include a corresponding reader. The identification tag allows the particle monitor to uniquely identify the cartridge. In another specific embodiment, a removable cartridge houses tape that does not include an adhesive-coated surface. For example, the tape may include an electrostatically charged surface which does not have adhesive material but rather an electrically conductive surface In another specific embodiment, the collection media includes a rigid disc. A side of the disc is coated with an adhesive to trap the airborne particles that enter the monitoring device. The disc exposes different regions around an annulus so that particles are trapped within a particular region. The disc may be made of plastic, nylon, metal, or any other rigid material. In another specific embodiment, the collection media includes adhesive-coated glass slides. In each embodiment, the adhesive coated tape (or other particle collection media such as adhesive-coated glass slides or adhesive-coated disc) may be removed from the particle collection device and fresh media inserted into the particle collection device. Anywhere a glass slide may be used, a plastic slide is likely to be an equally viable option. Removed media containing captured particles may be subjected to laboratory inspection and testing, archived for possible future laboratory inspection and testing, or both.

The collection media motor is responsible for advancing the collection media. For example, in an embodiment, the collection media includes a cartridge having a supply reel, an uptake reel, and an adhesive coated tape wound about the supply reel and connected to the uptake reel. Upon collecting some airborne particles on a portion of the adhesive coated tape, the media motor can advance the tape so that new particles can be trapped on another portion of the adhesive coated tape. The portion having the previously trapped airborne particles can be advanced to the particle identification subsystem for imaging and examination.

The collection media motor may include a counter that tracks a position of the tape. The position of the tape can be associated with the image. Storing the position information allows the tape to be later advanced (or unwound) to the same position at which the image was taken and additional analyses to be performed. The counter may count a number of units between a reference point on the tape (e.g., a beginning of the tape or an ending of the tape) and a location of the tape at which the image was taken. The units may be distance-based. For example, the location of the tape may be a distance as measured from the beginning of the tape.

The illumination subsystem includes various optical elements for generating and emitting light or radiation (e.g., visible light, ultraviolet light, infrared, or combinations of these) into the particles that have collected on the collection media. The illumination subsystem includes one or more light sources (e.g., two light sources). Each light source includes one or more light emitting elements.

In a specific embodiment, a lighting element includes a light emitting diode (LED). A light source may include a cluster of light emitting elements such as a cluster of LEDs (e.g., two or more LEDs). A cluster may include any number of light emitting elements such as LEDs. For example, a cluster may include one, two, three, four, five, six, seven, eight, or more than eight LEDs. In another specific embodiment, a lighting element includes a laser diode. There can be a combination of different types of light emitting elements such as a combination of LEDs and lasers.

The illumination subsystem may include lenses, filters, diffusers, or combinations of these for directing or modifying the light as desired. For example, a diffuser may be used to spread out the light from a lighting element and provide a soft light. A diffuser can help to ensure that the area around the collected particles is illuminated. In a specific embodiment, the illumination system includes optical fiber. The optical fiber can be used to collect light emitted by a light source and direct the light onto the collected particles.

In an embodiment, the illumination subsystem includes a first light source 444, and a second light source 446. In an embodiment, at least one of the first or second light sources includes quantum dots. In a specific embodiment, the quantum dots are suspended or dispersed within a film. The film can include a material in the form of a thin flexible sheet. The film is positioned to receive and convert the light from a lighting element. The film may be positioned at a distance from the light source or proximate or even inside the light source. For example, the quantum dots (or a layer having the quantum dots) may be placed so that they contact a surface of an LED chip. (see, e.g., FIG. 23). In another specific embodiment, the quantum dots may be mixed into an adhesive of the adhesive coated tape of the collection media. In another specific embodiment, the quantum dots may be placed on or into the backing material of the adhesive coated tape. In another specific embodiment, instead of absorbing and re-emitting light by quantum dots, an electrical current is passed through quantum-dots resulting in direct generation of light of the desired wavelength. Further discussion is provided below.

The optical subsystem includes various optical elements for capturing one or more images of the collected particles while the collected particles are being illuminated or radiated by the illumination subsystem. In an embodiment, the optical subsystem includes a microscope including a camera sensor 448 and lens assembly 450. A microscope is an optical instrument having a magnifying lens or a combination of lenses for inspecting objects too small to be seen or too small to be seen distinctly and in detail by the unaided eye. The lens assembly includes a set of lenses for bringing the collected particles into focus, magnifying the collected particles, or both. The camera sensor collects light scattered or reflected back from the particles to capture images or photographs.

The particle identification subsystem includes an image recognition engine 452, particle reference library 454, and context information acquisition unit 456. A particle identification manager 458 manages the particle identification or discrimination process.

The particle reference library stores reference information identifying different types of airborne particles. In a specific embodiment, the reference information includes particle-discrimination algorithm parameters. Optionally, these particle-discrimination algorithm parameters are determined by machine learning algorithms and a learning set of reference files that includes images including color photographs of different types of known particles. The machine learning algorithms that determine the particle-discrimination algorithm parameters may run locally, on the cloud, or both but the cloud is generally preferred in order to reduce the cost of computing hardware in the local device. The set of learning files may include reference images of tree pollen, grass pollen, weed pollen, mold spores, cat dander, dog dander, and so forth. Table A below shows an example of a data structure that may be used to store the reference information.

TABLE A

| Filename | Description |
| --- | --- |
| grass_pollen.jpg | Picture of grass pollens. |
| mold.jpg | Picture of mold spores. |
| . . . | . . . |

A first column of the table is labeled filename and lists the various files stored in the particle reference library. A second column of the table includes metadata (e.g., a description) that identifies the object in the corresponding file.

In an embodiment, the image recognition engine receives the image of the collected particles taken by the optical subsystem and analyzes the image using particle-discrimination algorithm parameters it previously received from the cloud. For example, particle-discrimination algorithms running in the particle identification subsystem may identify the collected particle as grass pollen. Some examples of parameters that may be considered in a particle-discrimination algorithm include autofluorescence properties (e.g., intensity of autofluorescence), size, shape, length of polar axes, length of equatorial axes (or diameter), ratio of polar axis to equatorial axis (P/E ratio), number of apertures, type of apertures, shape of apertures, position of apertures, lack of apertures, color characteristics, geometrical features, type of symmetry (e.g., radial symmetry or bilateral symmetry), lack of symmetry, other parameters, weights, or combinations of these. One or more of these parameters may be derived or extracted from optical system measurements, specified as a threshold, and then used as a discrimination algorithm parameter to discriminate particles.

The image recognition engine may use any competent technique or combination of techniques for recognizing the particles imaged by the optical subsystem. Some examples of image recognition techniques include edge detection, edge matching, changes in color, changes in size, changes in shape, divide-and-conquer searches, greyscale matching, gradient matching, histograms of receptive field responses, large model bases, interpretation trees, hypothesize and test, post consistency, pose clustering, invariance, geometric hashing, scale-invariant feature transform (SIFT), and speeded up robust features (SURF), among others.

The context information acquisition unit is responsible for obtaining context information associated with the particles that have been collected by the monitoring device. The context information may be based on a geographical location of the collected particles, a time and date of the collection, or both. In an embodiment, the context information includes blooming data. For example, spring blooming plants include oak, birch, hickory, and pecan. Fall blooming plants include ragweed. The context information may include weather conditions, temperature, wind speed, wind patterns, and so forth.

The context information may include a listing of particle types that have been identified by other nearby particle monitors, mobile drones, or both. For example, nearby particle monitors may include particle monitors that are within a specified radius of the requesting particle monitor. The radius may be, for example, 50, 100, 500, 1000, 2000, or more than 2000 meters. The radius may be less than 50 meters. The radius may be configurable such as by a user or administrative user. The radius may be determined dynamically. For example, the radius may vary proportionally to current wind speed as high winds can increase the likelihood of particles being carried into the local environment from remote areas.

The context information is used by the particle identification subsystem to help narrow the list of candidate particle types. Results of the particle identification subsystem may be outputted to the display, recorded in a log, or both.

The storage may include a particle identification log 460, images repository 462, and image index 464. The particle identification log records identifications of particles as determined by the particle identification subsystem. Table B below shows an example of information that may be recorded in the log.

TABLE B

| Image File | Context Info File | Particles Present | Timestamp | Location |
|---|---|---|---|---|
| 001.jpg | Context1.txt | Grass pollen | April 10, 2016, 11:34 AM | 45 Appleseed Drive, Santa Rosa, CA 94555 |
| 002.jpg | Context2.txt | Grass pollen | April 10, 2016, 1:36 PM | 45 Appleseed Drive, Santa Rosa, CA 94555 |
| 003.jpg | Context3.txt | Mold spores | April 11, 2016, 2:00 PM | 45 Appleseed Drive, Santa Rosa, CA 94555 |

In the example shown in table B above, a first column of the table lists the name of the file containing the image of the collected particles. A second column lists the name of the file containing the context information that may be associated with a geographical location of the collected particles, time and date of the collected particles, or both. The context information may be formatted as a text file, Extensible Markup Language (XML) formatted file, or in any other file format as desired. A third column of the table stores a timestamp indicating a time and date that the particles were collected. A fourth column of the table stores a location of the particle collection.

It should be appreciated that the data shown in table B above is merely an example of some of the metadata information associated with particle identification that may be stored in the database. In a specific embodiment, a particle information packet and particle information packet history is stored. Further details are provided below.

The images repository stores the image files generated by the optical subsystem. The files store digital images of the particles that have been captured. The files may include raw image files (e.g., digital negatives), raster images, bitmapped images, or combinations of these. The files may be formatted using any type of image file format (e.g., jpeg, exif, tiff, gif, bmp, png, and so forth).

The image index database stores metadata associated with the image files. The metadata may include, for example, image filenames, time and date that the image was taken, geographical location data, optical settings, and so forth. The metadata may include a description or specification of the lighting conditions, as provided by the illumination subsystem, under which the images were made. For example, the metadata may indicate that a first image was taken while particles were illuminated by white light, a second image was taken while the particles were illuminated by red light emitted from quantum dots, a third image was taken while the particles were illuminated by ultraviolet light, a fourth image was taken while the particles were illuminated by infrared light, and so forth. The index can be accessed and searched.

In a specific embodiment, the particle identification log, particle image files, image index, or combinations of these are transmitted from the particle monitor to the cloud server for further review, archival storage, backup. For example, the particle image files may be transmitted to the cloud server periodically or in batch such as nightly, weekly, or at any other frequency or time as desired. Once the image files have been transmitted to the cloud server, the image files may be deleted from the particle monitoring device. Deleting the images from the particle monitoring device frees up storage space for new images.

The GPS sensor provides geographical location information. The geographical location information allows the images of the collected particles to be tagged with the location of collection. As discussed, the location information is used to obtain context information such as the plants, flowers, or other vegetation currently in bloom at the geographical location of collection, weather conditions, identify other nearby particle monitors, or combinations of these.

The Bluetooth communication card or chip allows for a wireless pairing of the particle monitor and a user's mobile device. Bluetooth includes a communication protocol that allows for communicating over short distances (e.g., about 10 meters). The wireless pairing allows the particle monitor device and mobile device to exchange communication and other information. For example, in a specific embodiment, the particle monitor transmits to the mobile device a message including an identification of a particle that was collected. It should be appreciated that Bluetooth is merely one example of a standard for wireless communication. Other embodiments may include other communication standards in addition to or instead of Bluetooth such as WiFi.

In another specific embodiment, some of the components shown in the example of the particle monitor shown in FIG. 4 may be omitted and the data they provide may be fulfilled by the user's mobile device. For example, the sensor and allergic reaction detection subsystem may be omitted in another embodiment of the particle monitor. In this specific embodiment, the allergic reaction detection subsystem may be installed onto the mobile device as a mobile application program or "app" and the subsystem may rely on the sensor provided by the manufacturer of the mobile device to detect user actions, motions, and so forth. In this specific embodiment, when the "app" determines that the user has suffered an allergic reaction, the app sends a notification of the allergic reaction to the particle monitor so that the event can be logged and recorded.

Bluetooth (or WiFi) can further be used to determine that a user has entered the local environment in which the particle monitor is located by detecting the specific mobile device that the user may have on their presence. For example, a mobile device may be identified based on its International Mobile Equipment Identifier (IMEI), Media Access Control (MAC) address, or both. The IMEI includes a string of numbers that is unique for every device. A MAC address uniquely identifies wireless transmitters such as Bluetooth and WiFi chips that may be located in the device.

Detecting that the user has entered the local environment can be used to help move the particle monitor from a standby mode to an active mode. Conversely, detecting that the user has left the local environment can be used to help move the particle monitor from an active mode to a standby mode. A user does not have to remember to turn on the particle monitor each time the user enters the room (or to turn off the monitor each time they leave the room).

When the particle monitor is in standby mode, the particle monitor consumes less power (e.g., battery power) as compared to when the particle monitor is in active mode. The standby mode of operation helps to conserve power. Low power consumption is desired to minimize or lower electricity costs for the user and reduce the carbon footprint of the devices. For example, when the particle monitor is in standby mode, the particle monitor may not perform particle collection. When the particle monitor is in the active mode, the particle monitor may perform particle collection such as on a periodic basis. In a specific embodiment, a method includes receiving at a particle monitor a signal from a mobile device of a user indicating that the user is in a local environment of the particle monitor, transitioning in response to the signal from a standby mode to an active mode where the active mode includes collecting particles in the local environment, detecting based on an absence of the signal that that the user has left the local environment, and in response to the detection, powering down from the active mode to the standby mode where the standby mode does not include the collecting particles.

A power subsystem of the particle monitor may include a low-battery indicator unit. When the available battery power drops below a threshold (e.g., 20 percent battery remaining), the low-battery indicator unit can transmit a notification such as text message notification to the user's mobile device to notify the user that the particle monitor should be recharged.

The detection of a particular device can be used to identify different users of the particle monitor as long as each user has their own mobile device. For example, a user may be part of a family in a house where other family members also suffer from allergies. The particle monitor can track which user is currently in the local environment so that particle collections can be associated with a particular user. Being able to distinguish which user is currently in the local environment of the particle monitor helps to identify the specific airborne allergens that may affect each different user.

The housing motor turns or rotates the particle device housing about the base. The turning allows the air intake opening to pull in ambient air from different directions so that there is a good or representative sampling of air. The housing motor can be used to ensure that the air intake openings are aligned with a direction of wind so that airborne particles in the wind will enter through the air intake opening.

In a specific embodiment, the power source includes one or more batteries. The battery may be a rechargeable battery. Examples of rechargeable batteries include nickel cadmium (NiCd) batteries, nickel metal hydride (NiMH) batters, lithium ion (Li-ion) batteries, and others. When the rechargeable battery within the particle monitor is depleted, the batteries can be recharged by an AC adapter and cord that may be connected to the particle monitor.

Instead or additionally, the particle monitor may include a universal serial bus (USB) port. The USB port allows the particle monitor to be connected to a computer such as a desktop computer for charging. The port may also be used to configure the particle monitor via the desktop computer, transfer data from the particle monitor to the desktop computer, transfer data from the desktop computer to the particle monitor, or combinations of these. In another specific embodiment, the power source includes one or more disposable batteries.

The network interface controller provides the gateway to communicate with the mobile device, server, or both. In an embodiment, the network interface is connected to the Internet. The network interface controller may include an antenna for wireless communication, an Ethernet port to connect to a network via a cable, or both.

The housing may be made from a material such as plastic, nylon, metal, wood, or combinations of these. In a specific embodiment, the housing is made of plastic. A material such as plastic is desirable because a plastic housing allows for the passage of radio waves so that the particle monitor can communicate wirelessly. For example, an antenna located inside a plastic housing will be able to receive and transmit wireless signals through the plastic housing. Plastic is also relatively inexpensive to form and manufacture. In other cases, however, a metal housing may be desired. Metal can be less likely to crack as compared to plastic and users may prefer the aesthetic appearance of metal. In embodiments where the housing is made of metal, the antenna may be located or embedded on an outside surface of the housing.

Figure 5:
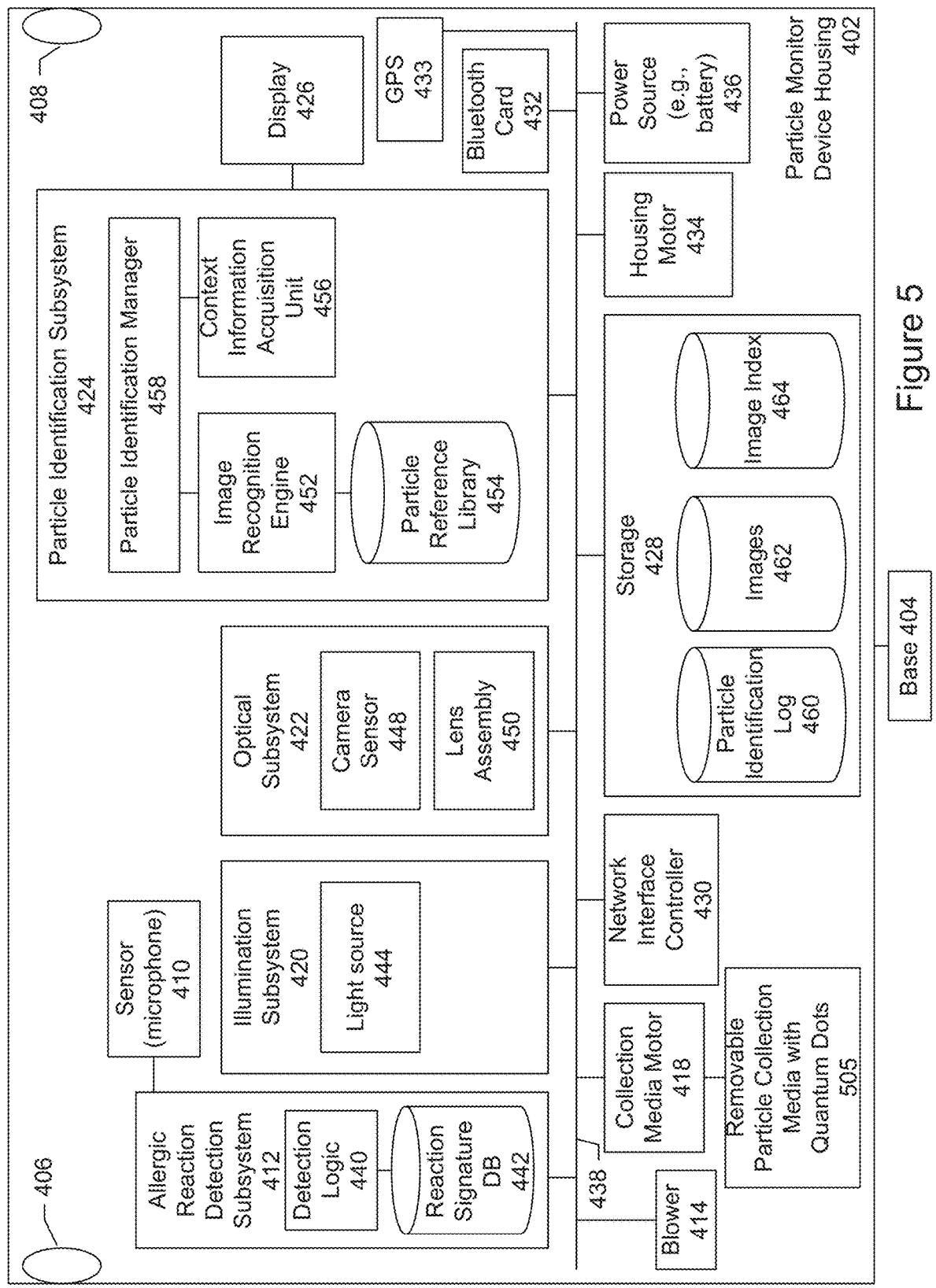
FIG. 5 shows a block diagram of an airborne particle monitor according to another embodiment.

FIG. 5 shows another specific embodiment of particle monitor 105. The particle monitor shown in FIG. 5 is similar to the particle monitor shown in FIG. 4. The particle monitor shown in FIG. 4, however, includes a removable particle collection media with quantum dots 505. In a specific embodiment, the collection media is contained within a cartridge. The cartridge includes a pair of spools and a tape wound about the pair of spools. The tape includes an adhesive and a backing material where the adhesive has been applied to a side of the backing material. In a specific embodiment, the quantum dots are within the backing material. In another specific embodiment, the quantum dots are within the adhesive. In another specific embodiment, the quantum dots may be included in a guide structure within the cartridge. Further detail is provided below.

Figure 6:
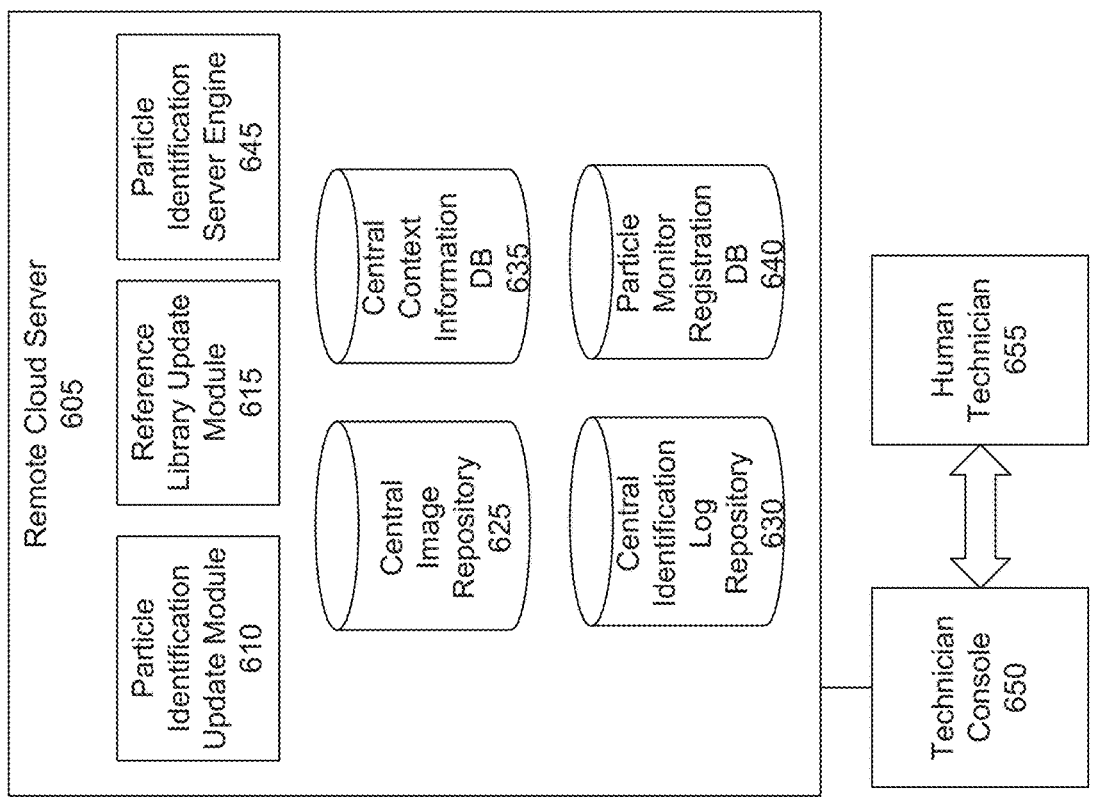
FIG. 6 shows a block diagram of a cloud server according to an embodiment.

FIG. 6 shows a block diagram of a remote cloud server 605 according to a specific embodiment. The server includes a particle identification update module 610, reference library update module 615, context information processing unit 620, central particle image repository 625, central particle identification log repository 630, context information database 635, database 640 storing information about various registered particle monitors that have been deployed, and particle identification server engine 645. A technician console 650 is connected to the server.

The particle identification update module is responsible for sending code updates to the various particle monitors that have been deployed throughout the world. The code updates may include firmware updates. The updates help to ensure that each monitor is equipped with the most recent versions of the algorithms for particle identifications.

The reference library update module is responsible for sending new or updated reference images of particles. For example, as new reference images of particles are made, these reference images can be distributed to each of the various particle monitors.

The context information database stores context information such as blooming periods of various plants and flowers, geographic location data for the various plants and flowers, weather conditions, and so forth. The context processing unit can receive from a particle monitor a request for context information where the request specifies a geographical location of the particle monitor, time of particle collection, or both. The context processing unit can access the context information database to retrieve a subset of relevant context information corresponding to the geographical location, time, or both and transmit the subset of relevant context information to the requesting particle monitor.

The central particle image repository stores images of particles that have been taken by the various particle monitors and transmitted to the cloud server. The images can be accessed and viewed via the technician console by a human technician 655. The central image repository (or other central repository) may further store the analysis results from the various particle monitors. This allows the technician to perform manual spot checks of the analysis to help ensure that the particle identifications made by the particle monitors are accurate. The image repository further allows the technician make a manual identification of particles by reviewing images where the local particle monitor is unable to make a satisfactory identification.

The central particle log repository stores particle identification logs generated by the various particle monitors and transmitted to the cloud server. As discussed, the particle identification logs can include listings of particle types that have been identified and associated metadata such as a time and date of particle capture, location of particle capture, and so forth.

The deployed monitors database stores information about the various particle monitors that have been deployed throughout the world. The database may be referred to as a particle monitor registration database. The information may include, for example, a geographical location of a particle monitor, particle identification logs containing information about particles captured by the particle monitor, images or an index to images taken by the particle monitor, user information (e.g., user first name, user last name, user email address, or user mailing address) date particle monitor was purchased, device serial number, firmware version, and other information. Table C below shows an example of information that may be stored in the deployed monitor database.

TABLE C

| Monitor ID | Location | Particle ID Log | Images Captured |
|---|---|---|---|
| 312945 | 45 Appleseed Drive, Santa Rosa, CA 94555 | 2016-05-12__31245_log.txt . . . | 2016-05-12__31245_image1.jpg . . . |
| 987431 | 32 Pear Lane, Philadelphia, PA 19042 | 2016-05-12__987431_log.txt . . . | 2016-05-12__987431_image1.jpg . . . |

A first column of the table lists an identifier that uniquely identifies a particle monitor. A second column of the table lists a location where the particle monitor is located. In this example, the location includes a street address. The location may instead or additionally include longitude and latitude coordinates, or any other value or set of values that identifies a geographic location of the particle monitor. A third column of the table lists particle identification logs received from the particle monitor. A fifth column of the table lists particle images received from the particle monitor.

The particle identification server engine is responsible for performing a server-side analysis of the imaged particles. For example, the cloud server may have access to computing resources not available locally at the particle monitor. The particle monitor is designed to be a relatively compact and inexpensive device. The server, however, may include processors more powerful than those at the particle monitor, be able to execute more complex particle identification algorithms than the particle monitor, and so forth.

In an embodiment, when the particle monitor is unable to identify a captured particle, the particle monitor notifies the server. The server can coordinate with the particle monitor in making an identification. For example, the server may use a different set of algorithms to analyze the particle images transmitted from the particle monitor to the server. Based on the analysis, the server may issue instructions to the particle monitor for additional images or other data. The instructions may include a request to capture additional images of the particles. The request may include a specification of the conditions or parameters under which the particles should be imaged. For example, the request may specify a focal depth at which an image should be taken, illumination under which the image should be taken, and so forth.

It should be appreciated that the cloud server is merely representative of an embodiment. There can be multiple cloud server and storage systems. Context information or portions of context information may be provided by one or more third parties. For example, weather conditions may be obtained from a third party that offers weather provider services (e.g., AccuWeather).

Figure 7:
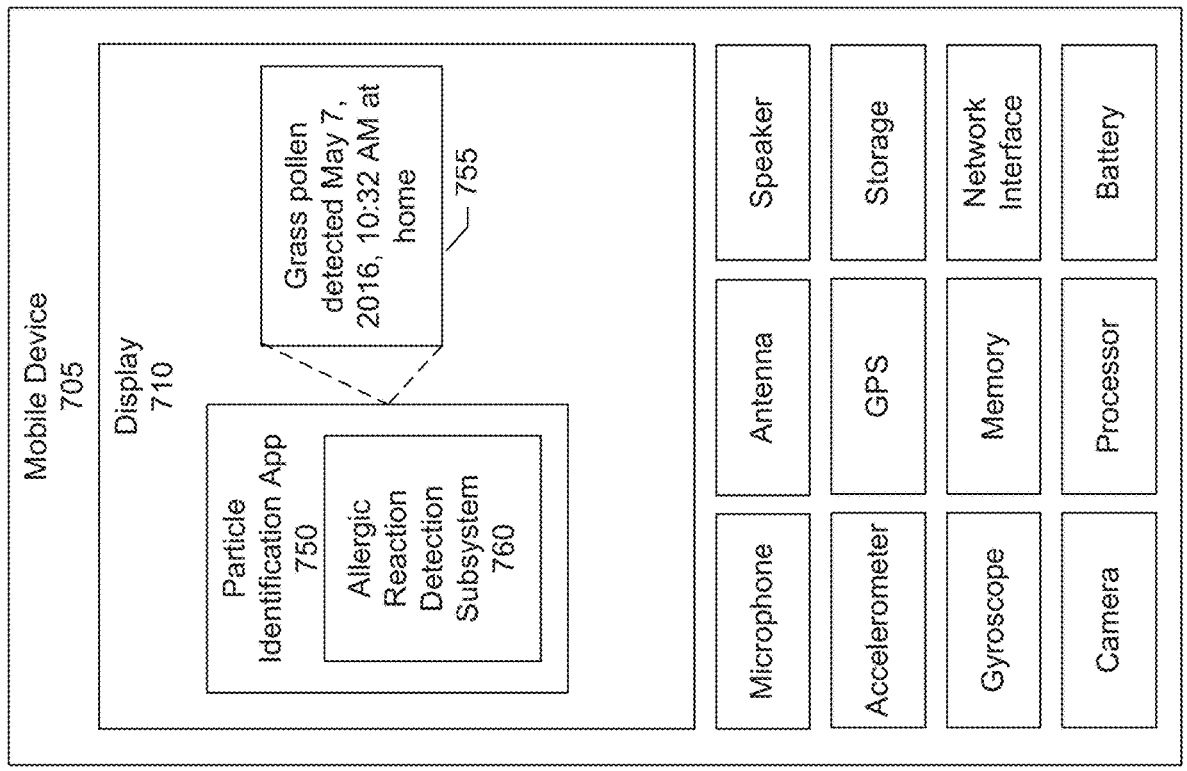
FIG. 7 shows a block diagram of a mobile device according to an embodiment.

FIG. 7 shows a block diagram of a mobile device 705 according to a specific embodiment. In the example shown in FIG. 7, the mobile device includes a display 710 and other hardware components such as a microphone, accelerometer/gyroscope, camera, GPS, memory, processor, storage, network interface, antenna, speaker, and battery. The mobile device includes a particle identification app 750 that allows the mobile device to be paired with a particle monitor as described herein. The particle identification app can display messages from the particle monitor such as a message 755 specifying the particles that have been collected and identified, e.g., "Grass pollen detected May 7, 2016, 10:32 AM at home."). The particle app may or may not include an allergic reaction detection subsystem or logic 760.

Figure 8:
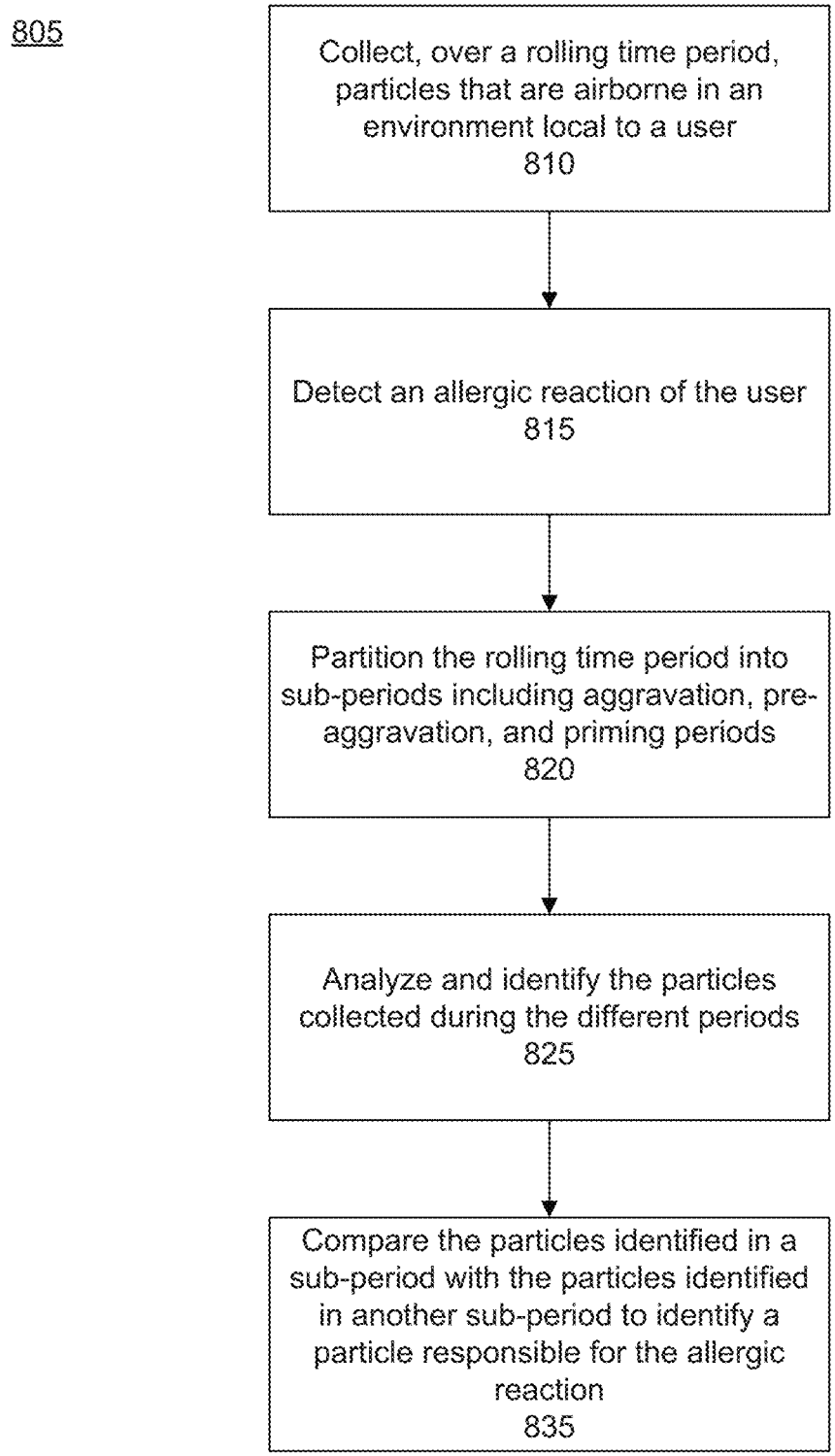
FIG. 8 shows an overall flow of a process for detecting and identifying airborne allergens according to an embodiment.

FIG. 8 shows an overall flow 805 of a system for collecting and identifying or discriminating airborne particles. Some specific flows are presented in this application, but it should be understood that the process is not limited to the specific flows and steps presented. For example, a flow may have additional steps (not necessarily described in this application), different steps which replace some of the steps presented, fewer steps or a subset of the steps presented, or steps in a different order than presented, or any combination of these. Further, the steps in other embodiments may not be exactly the same as the steps presented and may be modified or altered as appropriate for a particular process, application or based on the data.

In a step 810, a particle monitor collects, over a period of time, particles that are airborne in an environment that is local to a user. The local environment may include the user's house, a room in the user's house, the user's backyard, the user's front yard, the user's office, and the like. The local environment may be an area within about a 10 meter radius from the particle monitor.

In a step 815, an allergic reaction of the user is detected. In a specific embodiment, the allergic reaction detection subsystem receives via one or more sensors local to the user information indicating that the user may have experienced a physiological event.

The information may include, for example, an audio signal generated by a microphone local to the user, motion data generated by an accelerometer attached to the user, or both. The received information is compared to the database storing allergic reaction signatures. The signatures may include coughing sounds, sneezing sounds, coughing motions (e.g., motion data indicating a heaving of the chest or motion data indicating a covering of the mouth), and the like.

The signatures may be generated as part of a configuration or initial setup process in which the system prompts the user simulate an allergic reaction, records user activity associated with the simulated allergic reaction, and generates allergic reaction signature data based on the recorded user activity. Allergic reaction signatures may be generated for a particular user. This helps to ensure good accuracy in identifying an allergic reaction because the specific sounds, movements, or both of an allergic reaction may differ among individuals. In another specific embodiment, the system may store a set of default or generic allergic reaction signatures so that users are not required to simulate an allergic reaction as part of the configuration.

In another specific embodiment, upon detecting a potential allergic reaction, the system prompts the user to confirm whether or not they have indeed just suffered an allergic reaction. For example, the system may detect what appears to be a coughing or sneezing sound. In response, the system may display on an electronic screen of the user's mobile device a message, "Potential allergic reaction just detected. Please confirm 'Yes, I just had an allergic reaction,' or 'No, that wasn't an allergic reaction.'" Upon receiving a confirmation of an allergic reaction, the system classifies the event as an allergic reaction.

In a step 820, upon determining that the user has suffered an allergic reaction, the time period over which particles have been collected is partitioned into a set of sub-periods. The sub-periods include an aggravation period, pre-aggravation period, and priming period.

In a step 825, airborne particles collected during one or more of the sub-periods are analyzed and identified. In a specific embodiment, the analysis includes emitting first light to illuminate the collected particles, capturing a first image of the particles while the particles are illuminated under the first light, emitting second light, different from the first light, to illuminate the collected particles, and capturing a second image of the particles while the particles are illuminated under the second light. The emitted second light includes light emitted from a set of quantum dots. The emitted light enters the collected particles and, depending upon the absorption characteristics of the particles, may or may not be reflected back. The images are stored and analyzed to identify the particles that have been collected. There can be an any number of different illumination conditions and images made. Generating more images of the particles under different illumination conditions can be used to provide greater accuracy in identifying the collected particles.

In a step 835, particles identified in one sub-period are compared with particles identified in another sub-period to identify a particle responsible for the allergic reaction. For example, as discussed above, a particle detected during the aggravation period but not detected during the priming period may indicate that the particle is not responsible for the allergic reaction.

Figure 9:
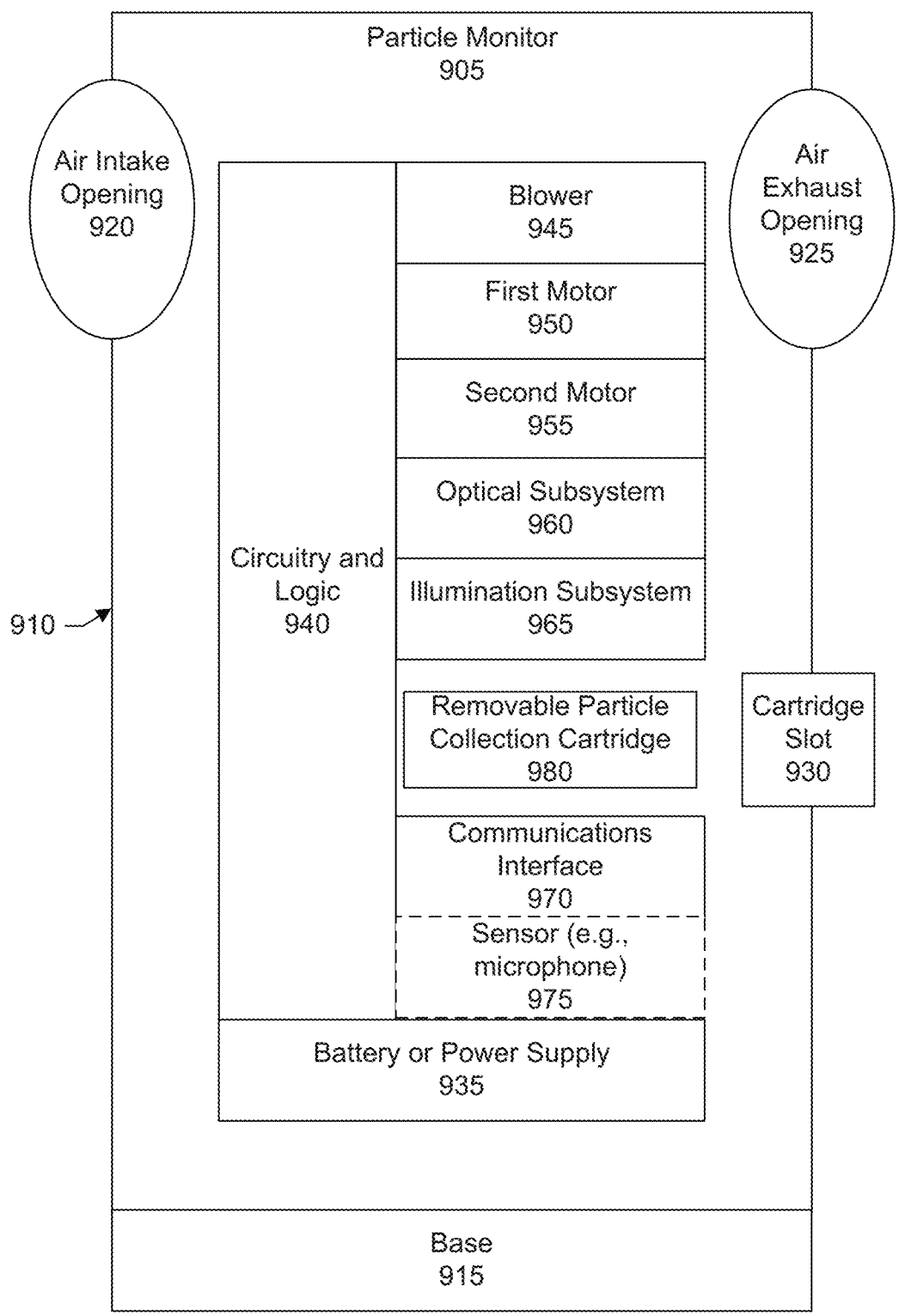
FIG. 9 shows a block diagram of an airborne particle monitor according to another embodiment.

FIG. 9 shows another block diagram of particle monitor 105 according to one embodiment. In the example shown in FIG. 9, a particle monitor 905 includes a housing 910 mounted to a base 915. The housing includes an air intake opening 920, an air exhaust opening 925, and a cartridge slot opening 930. There can be a door connected to the cartridge slot opening via a hinge. The door can open into the cartridge slot. Shown inside the housing are a battery or power supply 935 which is connected to circuitry and logic 940 which in turn is connected to a blower 945, first motor 950, second motor 955, optical subsystem 960, illumination subsystem 965, communications interface 970, and sensor 975 (e.g., microphone). The sensor is shown in broken lines to indicate that it is not included in some embodiments.

Further shown in FIG. 9 is a removable particle collection cartridge 980. The particle collection cartridge includes a reel of tape media. The tape media is wound about the reel and includes an adhesive to collect airborne particles (e.g., pollen or mold spores). The collection cartridge is removable from the collection device. That is, a user can remove the cartridge from the collection device without breaking or destroying the device. There can be an eject button that the user can press to eject the cartridge from the particle collection device. For example, when the collection cartridge is full (or as desired), the user can remove the collection cartridge from the collection device through the cartridge slot opening. The user can then install a new collection cartridge by inserting the new collection cartridge into the collection device through the cartridge slot opening. The user can then mail the removed collection cartridge—which contains the collected airborne particles—to a laboratory for a further in-depth analysis.

The design of the particle monitor and cartridge allows for a very flexible approach for collecting and analyzing particles. In particular, in another specific embodiment, the cartridge is used for surface particle sampling. Surface particle sampling may be instead of or in addition to airborne pollen or particle sampling. The cartridge facilitates a collection system or mechanism that is handheld and easily portable. A user can hold a body of the cartridge in their hand, position an opening or slot of the cartridge through which a portion of the tape is exposed, and press the slot against a surface of an object. Particles on the surface may then be transferred from the surface of the object to the exposed portion of the tape. The user can then insert the cartridge into the particle monitor for analysis of the particles that have been collected on the tape.

In a specific embodiment, a handheld portable particle monitor with removable collection cartridge is provided. In this specific embodiment, the monitor is a relatively small, lightweight, inexpensive, and compact device. The monitor is powered by a battery. This allows the monitor to be easily portable and mobile because the monitor does not have to be connected to an electrical outlet to operate. A user can take the monitor and cartridge to an environment where there might not be any electrical outlets such as to a vineyard, farm, plantation, ranch, forest, or other field environment to collect and analyze airborne particles, surface-borne particles, or both.

Particles that may be associated with diseases including agricultural diseases, plant diseases, animal diseases, and so forth can be easily collected, analyzed, and identified in the field before widespread damage occurs. The handheld particle monitor may include a handle connected to a body of the monitor so that the monitor can be carried. Instead or additionally, at a least a portion of an outside surface of the monitor body may be textured or knurled to facilitate carrying. Further, because the monitor may be used in outdoor environments, as well as indoor environments, the monitor may include seals to provide a weather-resistance or weather-proof construction. Examples of seals include O-rings, gaskets, all-weather glue, and others.

The particle collection device may include an electronic screen to display a status associated with operations of the particle collection device (e.g., "collection cartridge tape 80 percent full," "analyzing particles," "device error," "transmitting data to remote cloud server," "firmware update in progress, please wait," and so forth). There can be status lights such as LED status indicators. The particle collection device may include an input device such as a keypad through which the user can power the device on or off, configure various settings and parameters such as collection frequency (e.g., sample air every 5 minutes, every 10 minutes, every 20 minutes, or every 30 minutes), other settings, and so forth. Instead or additionally, at least some settings may be configured remotely.

The blower may include a fan and is responsible for creating a vacuum in which air is sucked into the collection device thorough the air intake opening. A flow path of air is directed to the particle collection cartridge. Particles that may be floating or suspended in the air are trapped by the adhesive tape of the particle collection cartridge. The air then exits the collection device through the air exhaust opening.

The first motor operates to rotate the housing of the collection device about the base. The collection device may include an airflow sensor or airflow direction sensing unit that detects a direction of the flow of the ambient air. Based on the direction of the airflow, the first motor can rotate the collection device to orient or align the air intake opening with a direction of the flow of the ambient air. Instead or additionally, the first motor may be configured to continuously or periodically rotate to obtain good representative samples of the ambient air.

The second motor engages the reel of the tape media to unwind the adhesive coated tape media. For example, as airborne particles such as pollen become trapped in a portion of the adhesive coated tape, the second motor can unwind the reel to expose a new portion of the adhesive coated tape upon which new airborne particles can be collected.

The second motor is further responsible for advancing the tape containing the trapped particles to the optical and illumination subsystems. One or more lighting sources of the illumination subsystem illuminate the trapped particles while a camera sensor of the optical system captures images (e.g., pictures) of the trapped particles for analysis and identification.

The communications interface is responsible for communications with, for example, the mobile device, remote cloud server, or both. The communications interface may include an antenna for wireless communication. The sensor (e.g., microphone) may be as described above.

Figure 10:
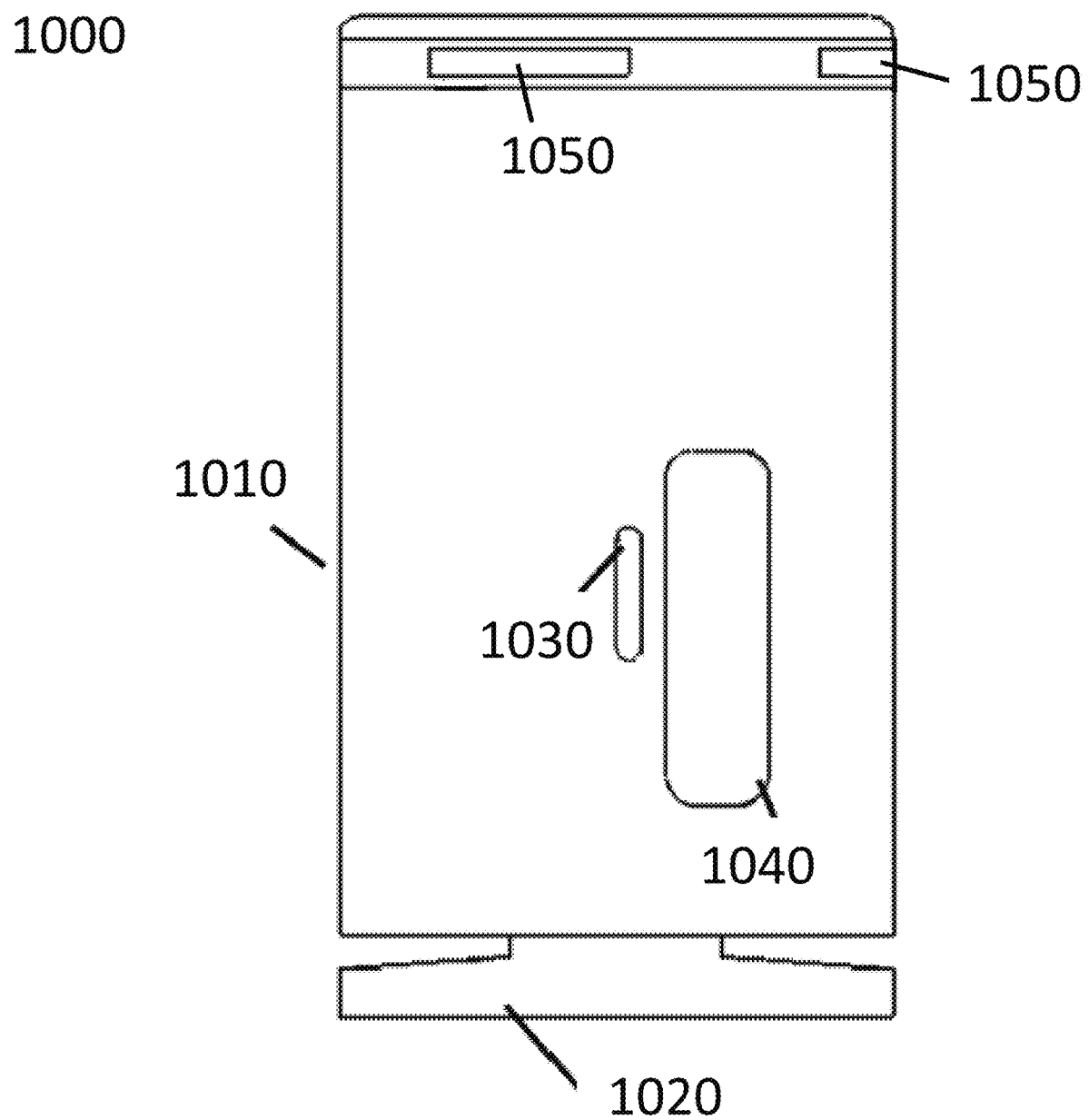
FIG. 10 shows an exterior view of an airborne particle monitor according to a specific embodiment.

FIGS. 10-18 show various views of particle monitor device 105 (and particle collection cartridge) according to an embodiment. FIGS. 10 through 18 illustrate in more mechanical design detail a specific embodiment of an airborne particle monitoring device. FIG. 10 shows an exterior view of a particle monitoring device 1000 including a cylindrical housing 1010 that contains most of the device components as well as a base 1020. Cylindrical housing 1010 contains an air-intake slot 1030 that may be a few centimeters in length and a width that varies from about 3 millimeters (mm) to about 1 mm in funnel-like fashion as it penetrates the thickness of the cylindrical housing 1010. The length of the air-intake slot may range from about 3 centimeters (cm) to about 10 centimeters. This includes, for example, 4, 5, 6, 7, 8, 9, or more than 10 centimeters. The length may be less than 3 centimeters.

Figure 11:
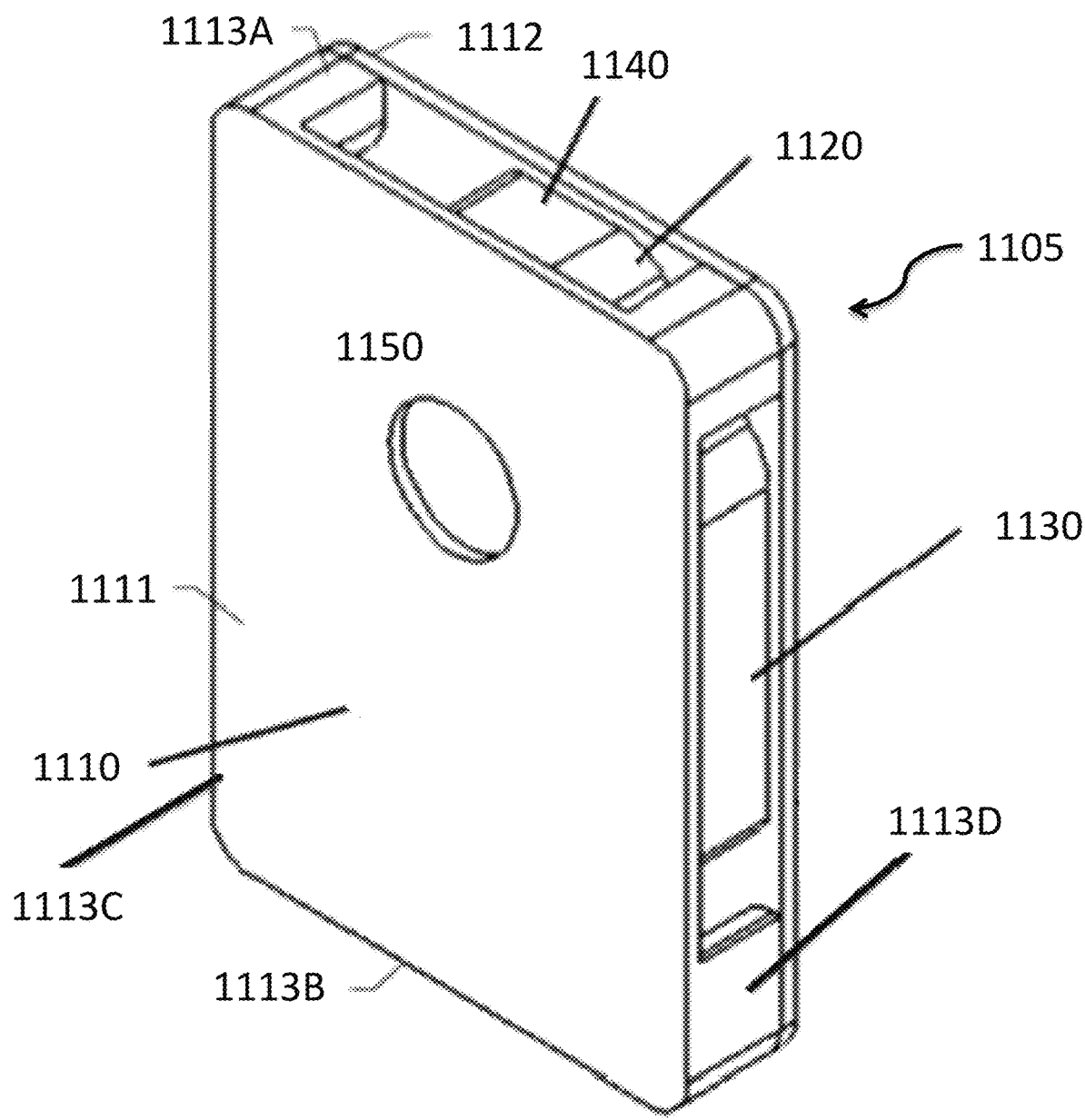
FIG. 11 shows an isometric view of a particle media cartridge that may be used with the particle monitor shown in FIG. 10.

The cylindrical housing 1010 also contains a particle-media-cartridge door 1040 that may be opened in order to insert or remove particle media cartridges such as shown in FIG. 11 and discussed below. The air-intake slot is adjacent or next to the cartridge door. A shape of the cartridge door includes a rectangle. The cartridge door is oriented vertically with respect to a central axis passing through the particle collection device. The door may be positioned closer to the base of the monitor than the top of the monitor.

As shown in the example of FIG. 10, in embodiment, the cartridge door includes a top door edge, a bottom door edge, opposite the top door edge, and left and right door edges extending between the top and bottom door edges. The bottom door edge is closer to the base than the top door edge and the bottom and top door edges are parallel to each other. The left and right door edges are opposite and parallel to each other.

The air-intake slot includes a top intake edge, a bottom intake edge, opposite the top intake edge, and left and right intake edges extending between the top and bottom intake edges. The bottom intake edge is closer to the base than the top intake edge and the bottom and top intake edges are parallel to each other. The left and right intake edges are opposite and parallel to each other.

In an embodiment, the air-intake slot is located relatively close to the cartridge door. This helps to allow particles in the air entering through the air-intake slot to be collected on the media cartridge. For example, an arc length as measured clockwise along the outside surface or circumference of the cylindrical housing from the left door edge to the right intake edge may be A1. An arc length as measured clockwise along the outside surface or circumference of the cylindrical housing from the right intake edge to the left door edge may be A2. Arc A1 may be less than arc A2. A ratio of A1 to A2 may be about 1:80. The ratio, however, may vary greatly and in other embodiments may be about 1:40, 1:45, 1:50, 1:55, 1:60, 1:65, 1:70, 1:75, 1:85, 1:90, 1:95, 1:100, 1:105, 1:110, 1:115, or 1:120. In an embodiment, the air-intake slot is between a first line or arc about the housing extending from the top door edge and a second line or arc extending from the bottom door edge, the first and second lines being parallel to each other. The air-intake slot may be shaped as a rectangle, oval, obround, circle, or any other shape as desired. There can be multiple air-intake slots (e.g., two, three, four, five, or more than five air-intake slots).

The cylindrical housing 1010 and its contents may rotate about its cylindrical axis with respect to the base in order to orient the air-intake slot 1030 in a desired direction. In some cases, it may be desired to systematically vary the orientation of the air-intake slot 1030 in order to average over all directions. Alternatively, the particle collection device 1000 may orient itself so that the air-intake slot 1030 faces upwind to any breeze or other flow of ambient air. In this latter case, it is advantageous for the particle collection device 1000 to include wind or airflow sensors. Visible in FIG. 10 are two of four wind-detector recesses 1050 in which may be mounted airflow sensors in such a way that they are both exposed to ambient airflow and mechanically protected from accidental impact or contact. In a specific embodiment, a wind-detector recess includes a cantilever deflection detector. Wind detectors of many types, including hot-wire airflow detectors, cantilever deflection detectors, or both may be placed in the wind-detector recesses 1050.

The generally cylindrical elongated shape of the housing helps to reduce interference with other external objects (e.g., furniture) when the collection device rotates to sample airborne particles such as pollen, mold spores, or both from different directions. In this specific embodiment, a cross-sectional shape of the housing includes a circle. In other specific embodiments, a cross-sectional shape of the housing may include a square, rectangle, oval, triangle, or any other shape.

Figure 12:
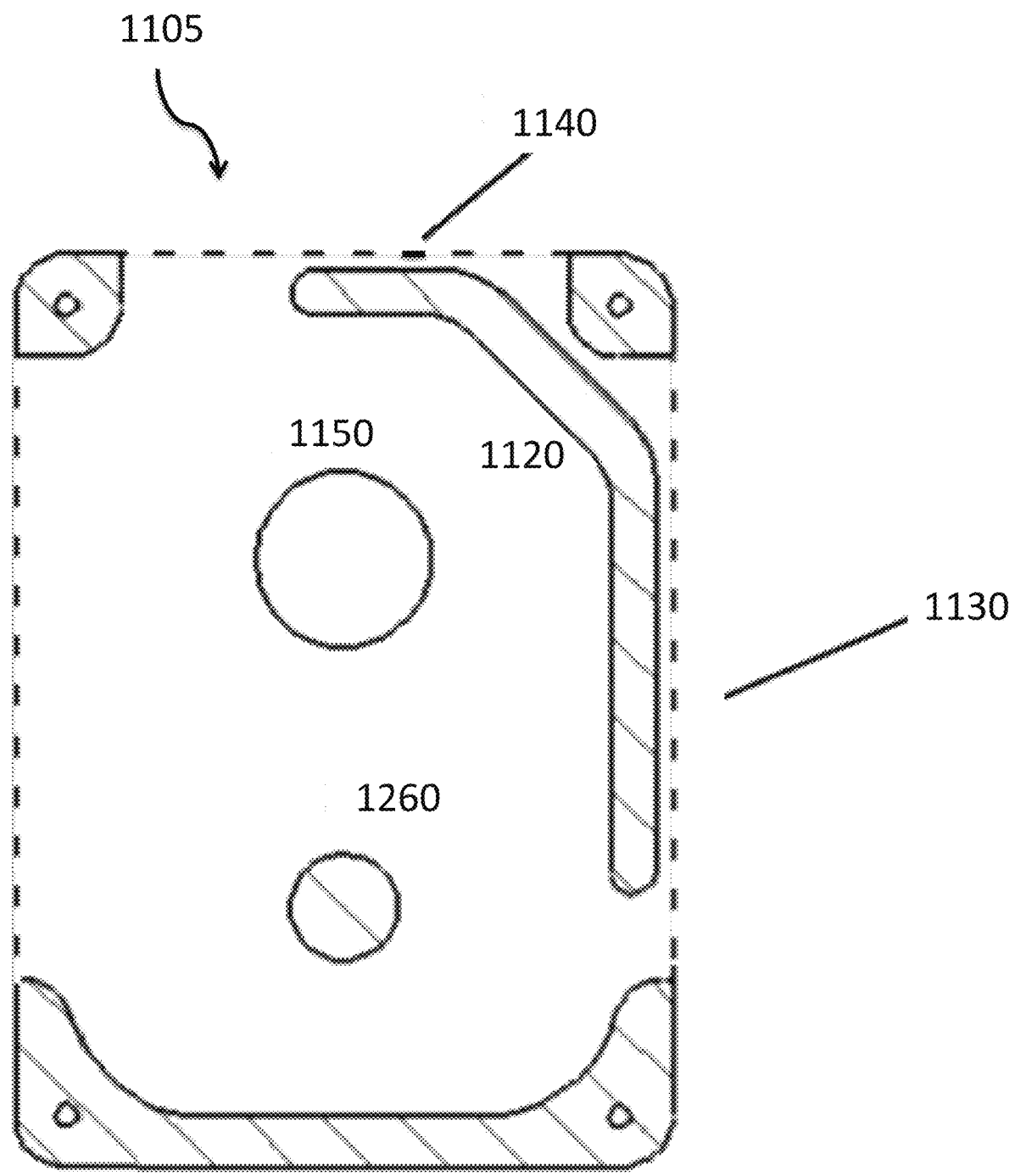
FIG. 12 shows a plan view of a cross section of the cartridge shown in FIG. 11.
Figure 13:
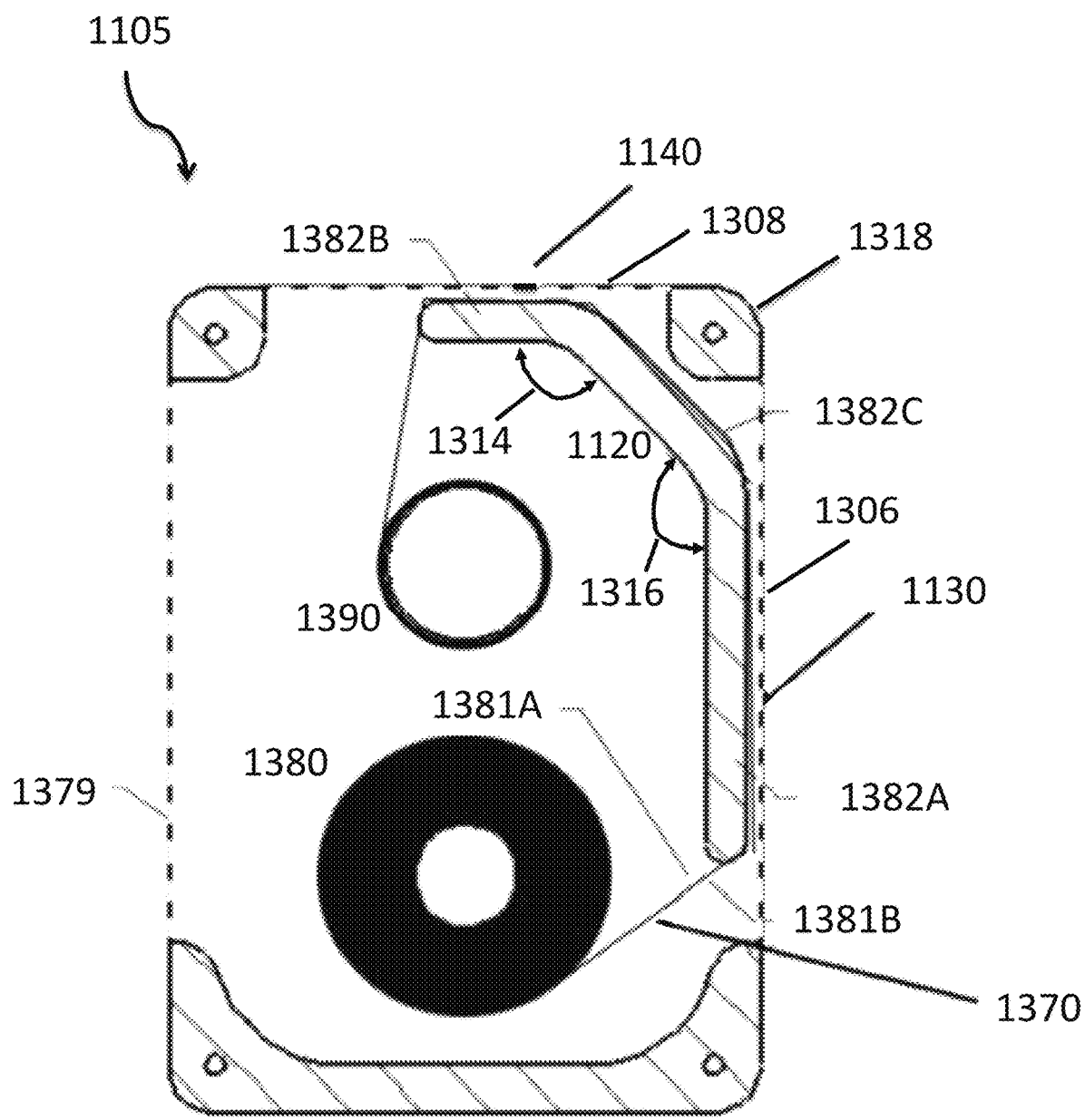
FIG. 13 shows a plan view of a cross section of the particle media cartridge including media of the cartridge shown in FIG. 11.

FIGS. 11-13 illustrate a particle media cartridge 1105 that may be loaded or removed from the particle collection device 1000 via the particle-media-cartridge door 1040. The cartridge includes a media for capturing particles as well as a cartridge body 1110. In this specific embodiment the media includes an adhesive coated tape, however, in other embodiments a different media may be used such as adhesive coated slides. The cartridge body 1110 includes a tape guide structure or wall 1120 that includes portions including an air-intake zone 1130 and a particle inspection zone 1140. The cartridge body 1110 includes a gear-shaft hole 1150 that will be discussed further below. In alternate embodiments, particularly in cases where it is desired to be able to rewind as well as advance the tape, there may be a second gear-shaft hole (not shown).

FIGS. 12 and 13 show a cross-section of the cartridge body with the media (FIG. 13) and without the media (FIG. 12). The cross-section is for a plane parallel to, in the middle of, planes corresponding to front panel 1111 (FIG. 11) and back panel 1112 (FIG. 11). The dashed lines in FIGS. 12 and 13 represent portions of the plan-view edges of front panel 1111 and back panel 1112 shown in FIG. 11.

Referring now to FIG. 13, a supply reel 1380 of adhesive coated tape 1370 is mounted to supply-reel post 1260 (FIG. 12). In the air-intake zone 1130, the tape guide structure 1120 both fixes the location of the adhesive coated tape 1370 where it collects particles in the face of air pressure from air entering the cylindrical housing 1010 (FIG. 10) via the air-intake slot 1030 (FIG. 10). The adhesive coated tape 1370 then passes the particle inspection zone 1140 and is finally collected at the uptake reel 1390. Optionally, after use within the particle collection device 1000, the particle-media cartridge may be removed from device 1000 and sent to a laboratory where particles captured by media can be further studied optically or with bio-assays. Such a particle-media cartridge physically containing captured airborne particles is one embodiment of physical archive 260 of FIG. 2.

Referring now to FIG. 11, in a specific embodiment, a user-removable or replaceable particle media cartridge is provided. The cartridge includes a front panel 1111, a back panel 1112, opposite the front panel. Side panels including a top side panel 1113A, a bottom side panel 1113B, a left side panel 1113C, and a right side panel 1113D extend between the front and back panels. The top and bottom side panels are opposite to each other. The left and right side panels are opposite to each other. The top and bottom side panels are orthogonal to the right and left side panels. As shown for left, top and right sides, side "panels" may cover only a small portion of their respective side. The cartridge has a shape of a rectangle.

Referring now to FIG. 13, the right side panel includes a first opening or slot that may be referred to as air intake zone 1130. The top side panel includes a second opening or slot that may be referred to as particle inspection zone 1140. The left side panel includes a third opening or slot that may be referred to as an exhaust port 1379. A length of the cartridge between the top and bottom side panels is L1, a width of the cartridge between the left and right side panels is W1, a length of the air intake zone opening is L2, a length of the particle inspection zone opening is L3, and a length of the exhaust opening is L4. In an embodiment, a ratio of L2 to L1 may be about 1:1.5, but may vary greatly such as 1:1.3, 1:1.4, 1:1.6, or 1:1.7. A ratio of L3 to W1 may be about 1:1.4, but may vary greatly such as 1:1.2, 1:1.3, 1:1.5, or 1:1.6. A ratio of L4 to L1 may be about 1:1.5, but may vary greatly such as 1:1.3, 1:1.4, 1:1.6, or 1:1.7.

A thickness of the cartridge between the front and back panels is T1. A width of the air intake zone opening is W2. A width of the particle inspection zone opening is W3. A width of the exhaust opening is W4. In an embodiment, the width of the openings W2, W3, and W4 are equal. In another embodiment, a width may be different from another width. In an embodiment, a ratio of at least one of W2, W3, or W4 to T1 is about 1:1.4, but may vary greatly such as 1:1.2, 1:1.3, 1:1.5, or 1:1.6. A shape of the intake zone, particle inspection zone, and exhaust openings may be a rectangle or other shape (e.g., oval, round, obround, or circle).

Inside the cartridge is supply reel 1380, uptake reel 1390, and tape guide structure 1120. The supply reel includes the roll of tape. The tape includes an inside or bottom surface 1381A and an outside or top surface 1381B, opposite the inside surface. The tape is wound so that the inside surface faces towards a center of the roll, and the outside surface faces away from the center of the roll. The outside surface of the tape includes an adhesive. The tape may be made of a thin flexible material such as narrow strip of plastic. In an embodiment, the tape is non-magnetic or not magnetic or does not include a magnetizable coating. The tape includes an adhesive coating on the outside surface of the tape to trap particles. In some embodiments, tape may be clear, translucent, transparent, or at least partially transparent to facilitate illumination of trapped particles. That is, the tape may be made of a material that allows at least some light to pass through.

The inside surface of the tape may not include the adhesive and preferably moves with minimal or low friction against tape guide 1120. The inside surface may be treated with a coating that allows the inside surface of the tape to glide freely across the tape guide. For example, in an embodiment there is a roll of tape including an inside surface and an outside surface. A coating or treatment is applied to the inside surface such that a coefficient of friction of the inside surface after the treatment is less than a coefficient of friction of the inside surface before the treatment. In another specific embodiment, the tape or portions of the tape may include a magnetizable coating. Such a magnetizable coating may be used to mark and read locations along the length of the tape of interesting particles that may merit later laboratory testing such as bio-assays.

The tape guide structure is sandwiched between the first and second panels of the cartridge. The tape guide includes a first segment 1382A, a second segment 1382B, orthogonal to the first segment, and a third segment 1382C extending between ends of the first and second segment. The first segment extends in a direction parallel to the right side panel. The first segment extends along at least a portion of the length of the front and back panels. The first segment includes a surface that faces the first opening (e.g., air intake zone) of the cartridge.

The second segment extends in a direction parallel to the top side surface. The second segment extends along at least a portion of the width of the front and back panels. The second segment includes a surface that faces the second opening (e.g., particle inspection zone). A length of the first segment may be greater than a length of the second segment. A length of the first segment may be less than a length of the second segment. A length of the first segment may be the same as a length of the second segment.

The tape extends from the supply reel, across the top surfaces of the first, second, and third segments of the tape guide structure, and terminates at the uptake reel. The uptake reel is closer to the top side of the cartridge than the supply reel. The supply reel is closer to the bottom side of the cartridge than the uptake reel. The tape is configured so that the inside surface contacts the top surfaces of the first, second, and third segments of the tape guide structure while the outside surface of the tape, which includes the adhesive, is exposed at the air intake and particle inspection zones. Thus, particles entering the air intake zone can be trapped by the adhesive and then inspected at the particle inspection zone. The air can pass from the air intake zone and out the exhaust port of the cartridge. The inside surface of the tape may be smooth or without the adhesive so that the tape can glide across the tape guide structure.

The first segment of the guide is positioned so that it is slightly recessed within the opening of air intake zone 1130. That is, right side edges 1306 of the front and back panels of the cartridge extend slightly past the first segment. A distance from the right side edges of the panels to the first segment may be at least a thickness of the tape. The recessing of the first segment helps to protect the tape from unintended contact with other objects.

Similarly, the second segment of the guide is positioned so that it is slightly recessed within the opening of particle inspection zone 1140. That is, top side edges 1308 of the front and back panels of the cartridge extend slightly past the second segment. A distance from the top side edges of the panels to the second segment may be at least a thickness of the tape. The recessing of the second segment helps to protect the tape from unintended contact with other objects.

In the example of the cartridge shown in FIG. 13, the first and second segments of the tape guide are on adjacent sides of the cartridge. That is the first segment is on the right side of the cartridge and the second segment is on the top side of the cartridge. The position of the tape guide segments corresponds to the design of the particle monitor. For example, when the cartridge is inserted into the particle monitor, the second segment of the tape guide will be located directly below the optical subsystem or microscope including camera sensor and lens assembly. It should be appreciated, however, that the tape guide segments may be positioned at other locations depending upon the design of the particle monitor.

An angle 1314 is between the second and third segments. An angle 1316 is between the first and third segments. In an embodiment, the angles are obtuse, i.e., the angles are more than 90 degrees but less than 180 degrees. The angles and positioning of the tape guide segments help to prevent creases in the tape as the tape transitions from the supply reel, to the intake zone, below and past an upper right corner 1318 of the cartridge, to the inspection zone, and to the uptake reel. The ends and corners of the tape guide may be rounded as shown in the figure to help ensure that the tape glides smoothly over the tape guide and does not snag.

The cartridge, including the tape guide structure, may be made of plastic, nylon, metal, or other material, or combination of materials. The tape guide structure may be formed or molded as a single unit with one of the front or back panels of the cartridge. Alternatively, the tape guide structure may be formed as a unit separate from the front and back panels. When the tape guide structure is formed as a separate unit, the tape guide structure may be attached to at least one of the front or back panels using any number of a variety of techniques. Such techniques may include snap-fits, fasteners (e.g., screws), glues, and others.

Likewise, the front and back panels may be fastened together using any number of a variety of techniques. For example, the front and back panels may be snap-fitted together. The front and back panels may be glued together. In an embodiment, the front and back panels are connected using screws. In this embodiment, each corner of one of the front or back panel may include a screw boss. The boss provides a mounting structure to receive a screw. The screw passes through a hole in a corner of one of the front or back panels and is received by a screw boss located in a corresponding corner of another of the front or back panels.

Figure 14:
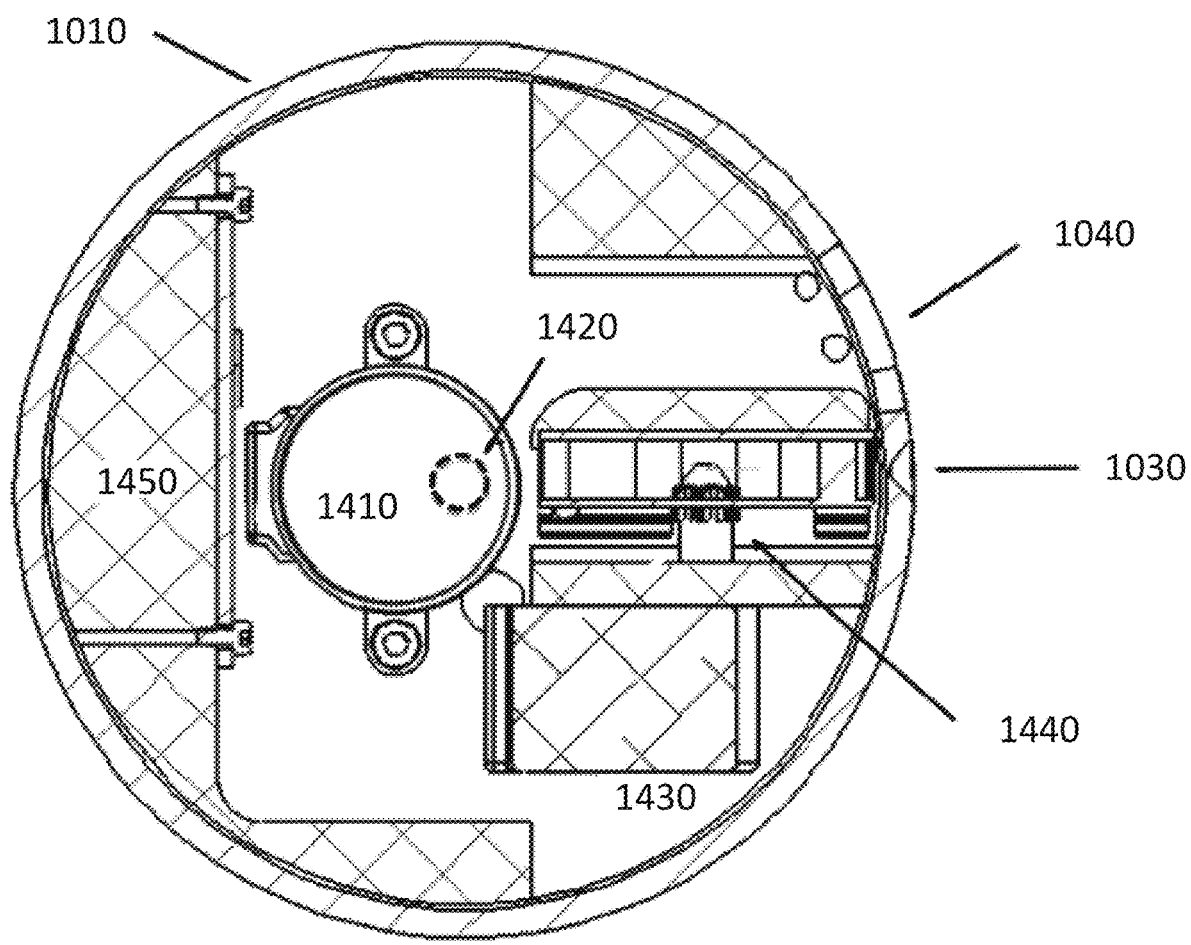
FIG. 14 shows a plan-view of the particle monitor shown in FIG. 10 including motors.

FIG. 14 shows a plan-view of selected items of the particle collection device 1000 shown in FIG. 10. The device includes two electric motors. Orientation motor 1410 rotates the cylindrical housing 1010 and its contents about its vertical axis and relative to the base 1020 (FIG. 10). While the orientation motor 1410 is not centered with respect to the axis of the cylindrical housing 1010, the orientation motor's gear shaft 1420 is centered. The intake-reel gear shaft 1440 of the cartridge-reel motor 1430 extends horizontally and controls the rotation of the uptake-reel 1390 (FIG. 13) of the cartridge. The gear shaft hole 1150 (FIG. 12) allows the intake-reel gear shaft 1440 to enter the particle-media cartridge body 1110 (FIG. 11). Many of the contents contained within the cylindrical housing 1010, including motors 1410 and 1430, are mechanically supported by the internal mounting structure 1450. For example, internal components of the monitoring device such a printed circuit board, motors, and so forth may be attached to the internal mounting structure using various fasteners, welding, adhesives, or combinations of these. Examples of fasteners include nuts, bolts, screws, and washers. Adhesives include epoxy or glue. Examples of welding include plastic welding. The internal mounting structure 1450 may be formed of a sculpted volume of plastic. The mounting structure may be formed using injection molding.

Figure 15:
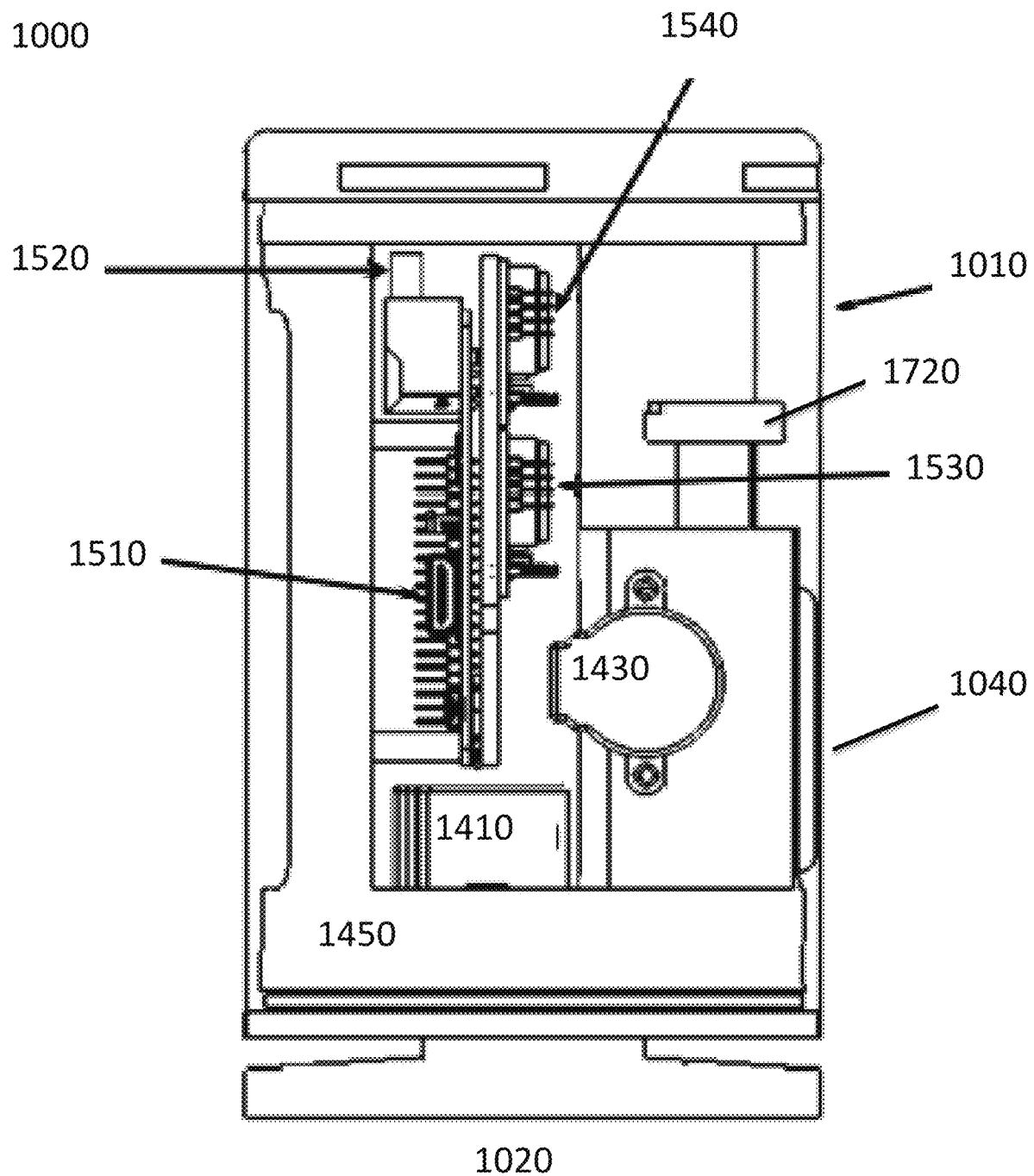
FIG. 15 shows a vertical cross-section of the particle monitor shown in FIG. 10 illustrating the placement of electronic boards.

FIG. 15 shows a vertical cross section of particle monitor device 105 according to a specific embodiment. In this specific embodiment, the particle collection device includes three electronic boards. There is a motherboard 1510, an orientation-motor circuit board 1530, and a cartridge reel motor circuit board 1540.

Motherboard 1510 contains many electronic components including a microprocessor (e.g., Raspberry Pi) and a wifi antenna 1520. Alternatively Bluetooth or any other wireless protocol may instead or additionally be used. For effective wireless communication, it is preferable that cylindrical housing 1010 be constructed from a non-conductive material such as plastic rather than a metal.

Additional circuit boards (not shown) may be included. Also not shown in FIG. 15 for purposes of clarity are numerous wires interconnecting various components such as wires between the motors and their corresponding circuit boards. Motherboard 1510 may contain the hardware of local processor 240 of FIG. 2.

The motors are located closer to a bottom of the particle monitor than a top of the particle monitor. Motors can be relatively heavy. Locating the motors towards the bottom of the particle monitor helps to lower the center of gravity and provide stability so that the monitor is unlikely to tip over. Likewise, a power supply such as a battery may be located closer to the bottom of the monitor than the top of the monitor.

Specifically, with respect to a vertical positioning, the orientation motor is between the bottom of the monitor and the motherboard. The cartridge reel motor is between the orientation motor and the camera sensor. The camera sensor, being relatively light, is positioned closer to the top of the monitor than the bottom of the monitor. The camera sensor is between the cartridge reel motor and the top of the particle monitor. With respect to a horizontal positioning, the cartridge reel motor is between the motherboard and the cartridge door.

Figure 16:
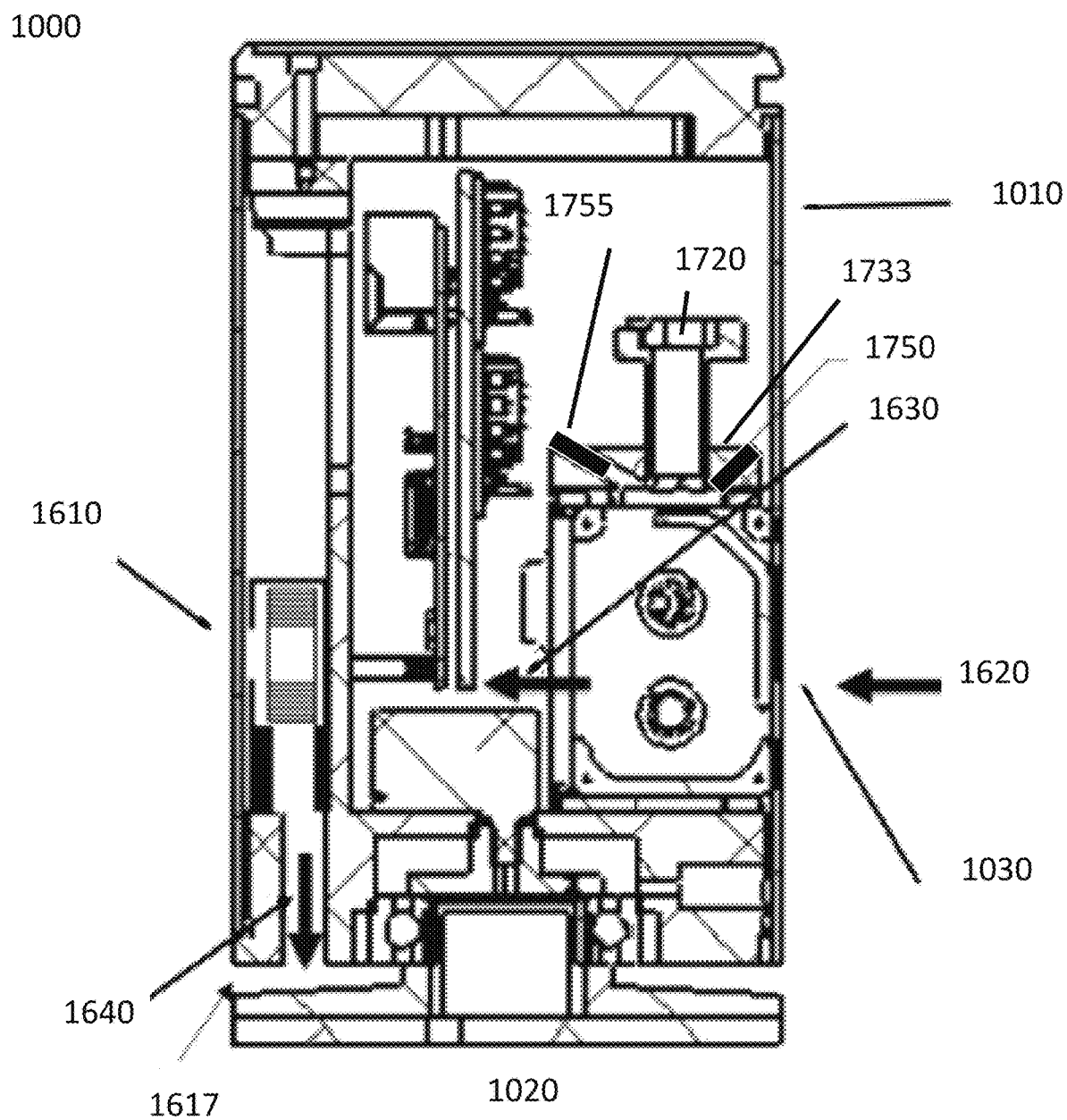
FIG. 16 shows some detail of the particle monitor shown in FIG. 10 with optics and particle media cartridge, as well as illustration of air flow.

FIG. 16 illustrates how sampled ambient air flows through the monitor device 1000. Sampled ambient air 1620 enters through the air-intake slot 1030 and immediately encounters the air-intake zone 1130 (FIG. 13) of the particle-media cartridge. Here the adhesive-coated tape 1370 (FIG. 13) captures many of the particles within the sampled ambient air 1620. Device-interior air 1630 then exits out the back side of the particle-media cartridge body 1110 (FIG. 11); for this purpose and as seen in FIG. 13, the back side of the cartridge is open rather than closed. Finally exhaust air 1640 (FIG. 16) leaves the device. This airflow is driven by blower 1610 which pushes out exhaust air 1640 and sucks in sampled ambient air 1620. The blower is opposite the air intake slot and above the exhaust. A gap 1617 between a bottom of the housing and a top of the base allows the exhaust air to escape. The mechanisms for ambient air sampling illustrated in FIG. 16 represents one embodiment of air intake hardware 220 of FIG. 2.

Air intake slot 1030 is opposite the blower and is configured to direct a flow path of ambient air created by the blower towards or over the first opening of the cartridge or air intake zone. For example, there can be channel, duct, conduit, tube, or passageway that directs the flow path of the air from the air intake zone. Particles, such as pollen, mold spores, or both, in the air are trapped by the adhesive on the tape. Preferably, the airflow in the air intake zone is turbulent in order to maximize or increase the chances that particles in the sampled air will be separated from the air and adhered to the capturing medium. When desired, cartridge reel motor 1430 (FIG. 14) advances the tape containing the trapped particles to the second opening of the cartridge or inspection zone. The camera sensor can then capture images of the particles trapped within the adhesive tape.

Figure 17:
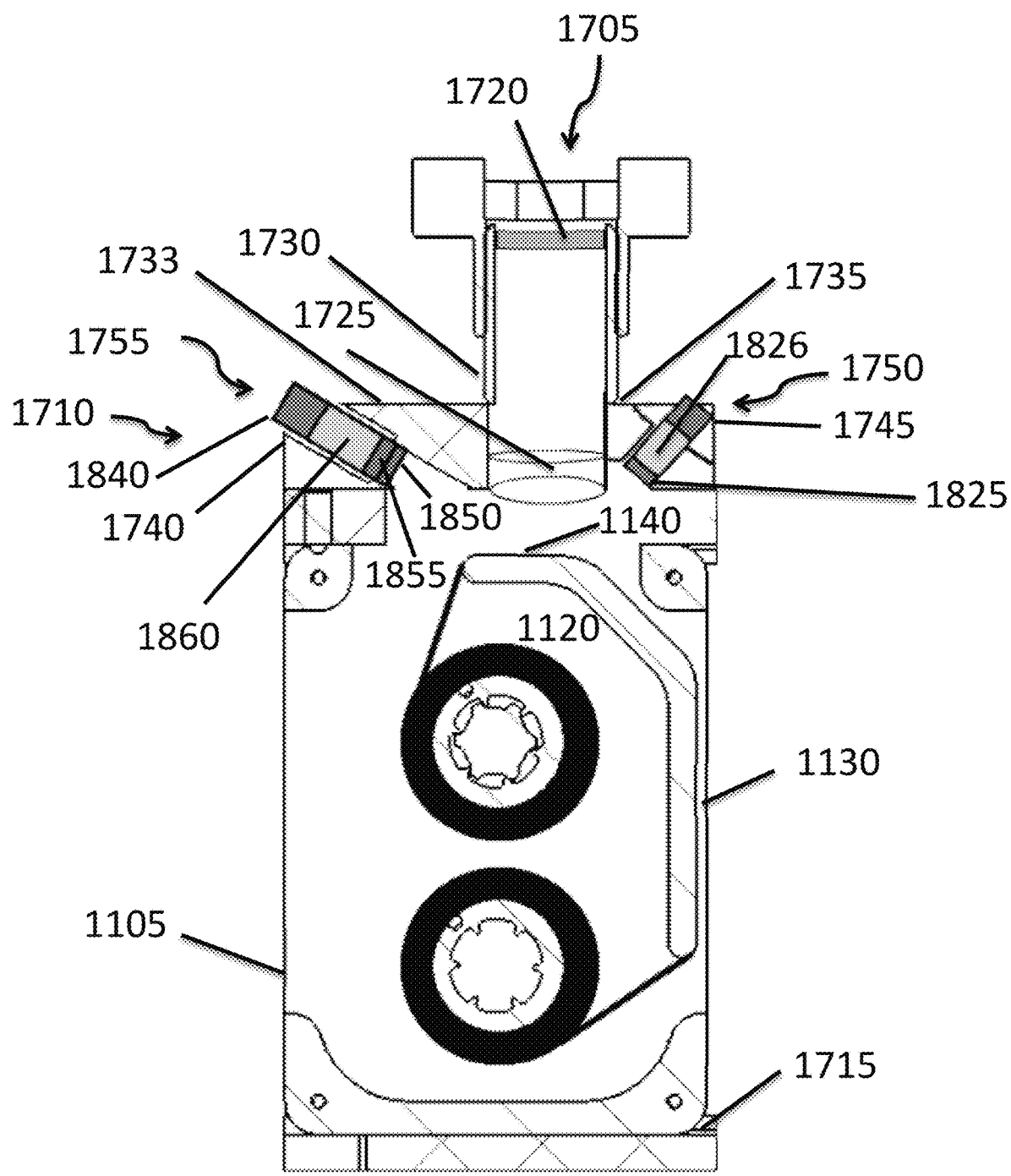
FIG. 17 shows a side view of an inside portion of the particle monitor shown in FIG. 10.
Figure 18:
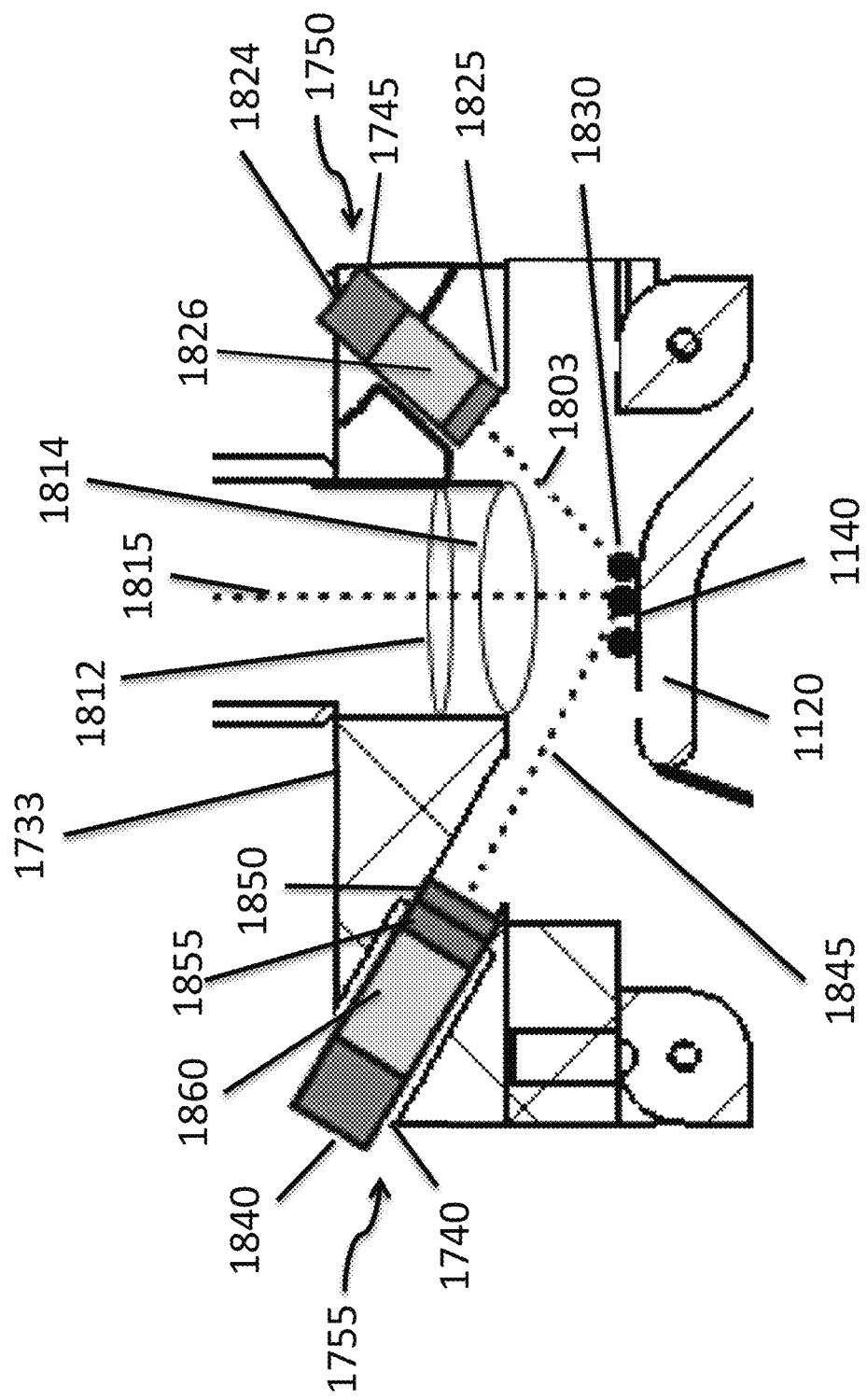
FIG. 18 shows an enlarged side-view cross-section of the particle monitor shown in FIG. 10 showing further details of the optical and illumination system according to a specific embodiment.

FIG. 17 shows a side view of an inside portion of monitor device 1000. The monitor device includes an optical subsystem 1705, illumination subsystem 1710, cartridge well 1715, platform 1733, and particle-media cartridge 1105. FIG. 17 illustrates a loaded particle-media cartridge in the cartridge well along with an optical subsystem for particle inspection. FIG. 18 provides more detail on the optical and illumination subsystems. During a collection period, particles entering the monitor are trapped within air intake zone 1130 by the adhesive of the tape. The tape or, more specifically, a portion of the tape having the trapped particles, is then advanced to particle inspection zone 1140 for inspection. The duration of the collection period can be configured by a user or administrative user. For example, the collection period may be configured to be 5, 10, 15, 20, 30, 60, 90, 120, or more than 120 seconds (e.g., 3, 4, 5, 6, 7, 8, 9, 10, 15, 30, 45, or more than 45 minutes; 1, 2, 3, 4, 5, or more than 5 hours). The collection period may be less than 5 seconds.

The optical subsystem includes a camera sensor 1720, lens assembly 1725, and tube 1730. The lens assembly is positioned at a bottom end of the tube and the camera sensor is positioned at a top end of the tube, opposite the bottom end of the tube. The cartridge well receives and holds the particle-media cartridge in a vertical position.

Platform 1733 is positioned above the cartridge well. The platform can be between the cartridge well and illumination and optical subsystems. The platform includes a first hole 1735, a second hole 1745, and a third hole 1740. The bottom end of the tube of the optical subsystem extends into the first hole which opens to face particle inspection zone 1140 of the particle media-cartridge. In other words, when the particle media-cartridge is inserted into the particle monitor, the particle inspection zone of the cartridge aligns with the first hole. The camera sensor is directly above the lens assembly which is directly above the particle inspection zone. The arrangement allows the camera sensor to capture images of particles that have been trapped by the adhesive coated tape.

In other words, in the example shown in FIG. 17, the platform is above the cartridge well that receives the collection cartridge. The camera sensor is positioned within the particle monitor device to be above or over the second opening or particle inspection zone of the cartridge. The camera sensor is closer to a top of the particle monitor than the cartridge.

Positioning the camera sensor above the particle inspection zone helps to reduce the probability of particles falling onto the camera lens and obscuring the images. For example, in some cases, the bond between the adhesive coated tape and collected airborne particles may be weak, the adhesive coated tape may include a large collection or mound of particles and particles at the top of the mound may not be secured to the adhesive coated tape, and so forth. The collection cartridge and camera sensor may be aligned such that a line passing through the supply and uptake reels passes through the particle inspection zone and lens to the camera sensor.

In a specific embodiment, the cartridge well is rotatable about a vertical axis parallel to the central axis passing longitudinally through the housing. For example, at least one of the top, bottom, or side of the cartridge well may be connected to a pin (e.g., rod, spindle, shaft, or axle). The pin may sit or revolve within a hole, bushing, or ball bearing connected to the housing. In this specific embodiment, when the media cartridge is loaded through the cartridge door and into the monitor, the cartridge well can pivot so that the air-intake slot of the housing aligns with or faces the air intake zone of the cartridge. This helps to facilitate airflow towards the air intake zone of the cartridge.

In an embodiment, the cartridge well pivots through a distance at least a thickness of the cartridge. The cartridge well may pivot through any number of degrees (e.g., 1, 2, 3, 4, 5, 10, 15, 20, 30, 60, 90, 120, or 180 degrees). The ability of the cartridge well to pivot allows the air-intake slot to be located anywhere on the housing. For example, the air-intake slot may be located on an opposite side of the cartridge door. In other words, a distance between the air-intake slot and the cartridge door may be equal to a diameter of the housing or half the circumference of the housing.

Rotating the cartridge away from the cartridge door helps to ensure that ambient or outside light that may enter or leak through the cartridge door and into the interior space of the monitor does not enter the particle inspection zone when the trapped particles are being illuminated by the illumination subsystem. Reducing or minimizing the amount of ambient or outside light entering the particle inspection zone helps to ensure accurate measurements.

In a specific embodiment, the illumination and optical subsystems remain stationary or are fixed-in-place while the cartridge well pivots. This helps to ensure consistent measurements. In another specific embodiment, one or more of the illumination or optical subsystems may pivot with or with respect to the cartridge well.

The cartridge well may pivot through any number of positions. For example, there can be a first position in which the cartridge well faces the cartridge door so that the cartridge can be loaded into the well. The cartridge well may then pivot from the first position to a second position where the air intake zone of the cartridge faces the air intake slot of the housing. The cartridge well may remain in the second position while the collected particles are illuminated and particle images captured. The cartridge well can then pivot from the second position back to the first position so that the cartridge can be removed and another cartridge inserted.

In another specific embodiment, there can be a first position in which the cartridge well faces the cartridge door so that the cartridge can be loaded into the well. The cartridge well may then pivot from the first position to a second position where the air intake zone of the cartridge faces the air intake slot of the housing. Once a collection period has ended, the cartridge well may pivot from the second position to a third position, away from the air intake slot, where the collected particles are illuminated and particle images captured. The cartridge well can then pivot from the third position back to the second position for another particle collection session, or pivot back to the first position so that the cartridge can be removed and another cartridge inserted.

In other embodiments, the cartridge well may be designed to translate. For example, in another specific embodiment, a particle monitor may include a tray that slides out of the particle monitor. The tray receives the cartridge and slides back into the particle monitor. In the example shown in FIG. 10, the cartridge door is shown as being on a side of the particle monitor between the top and bottom of the monitor. The side entry helps to facilitate a short overall height and small diameter of the monitor.

In other embodiments, however, the cartridge door may be located on the bottom of the monitor and the cartridge may be inserted through the bottom of the monitor. Locating the cartridge door on the bottom helps to reduce the probability of unwanted water (e.g., rain) or other debris entering into the monitor. The cartridge door may be located on the top of the monitor and the cartridge may be inserted through the top of the monitor. Locating the cartridge door at the top can allow a cartridge to be loaded and removed without having to pick-up the monitor.

As shown in FIG. 17, the optical subsystem is slightly offset towards a right side of the platform. The optical subsystem is closer to the right side of the platform than a left side of the platform, opposite the right side. The optical subsystem may be closer to a side of the cylindrical housing than a central axis passing longitudinally through the cylindrical housing. This offsetting or arrangement of the optical system helps to facilitate the compact design of the particle monitor device as other internal components may be located to the left of the optical tube. Also, to better approximate real-time monitoring, such an offset also has the benefit of reducing the distance between the particle capture at air intake zone 1130 and particle inspection zone 1140. In another specific embodiment, the optical axis may be symmetric with respect to the light sources.

The second hole 1745 houses a first illumination or light source 1750. Light from a first light emitting element 1824 (FIG. 18) is directed within a guide 1826 to a diffuser 1825. The third hole 1740 houses a second illumination or light source 1755. The illumination sources illuminate the particle inspection zone so that the camera sensor can capture images of the trapped particles when illuminated by the illumination sources.

For example, FIG. 18 shows an enlarged view of a portion of the section view shown in FIG. 17. Particles 1830 collected on the tape have been moved to particle inspection zone 1140. First light source 1750 illuminates 1803 the particle inspection zone with first light. Camera sensor 1720 (FIG. 17) captures images of particles in particle inspection zone 1140 (or a scene) within a field view of the camera sensor to generate a first image. That is, the first image is generated while the particles are illuminated with the first light. Second light source 1755 illuminates the particle inspection zone with second light, different from the first light. The camera sensor captures particles in the particle inspection zone within the field view of the camera sensor to generate a second image. That is, the second image is generated while the particles are illuminated with the second light.

In an embodiment, it is desirable that the area around the particle inspection zone be dark. This helps to provide a controlled lighting environment for illuminating the particles under different specified lighting conditions and image capture. Thus, components within the area around the particle inspection zone may be black, colored black (e.g., painted black or a dark color), non-reflective, processed so that the resulting surface finish is darker as compared to the surface before the processing, and so forth.

The first and second lights have different spectral characteristics. For example, the first light may include white light (e.g., light having a broad range of wavelengths and is perceived by the human eye as being colorless) and the second light may include light corresponding to an absorption spectrum of a particle of interest. In an embodiment, the first and second images are analyzed to identify or discriminate the particles. For example, the first and second images may be compared to each other to detect changes or differences in the appearance of the particles in the images based on the different lighting conditions under which the particles were photographed.

Detecting such changes (or the lack of changes) can provide an indication of what a particle might be (or not be) because different types of particles can have different light absorption characteristics. These differences in light absorption characteristics can be exploited in order to identify or discriminate the particles. Capturing various images of the same particles but under various different lighting conditions can be used to "probe" and identify or discriminate the particles.

As discussed, lens assembly 1725 images the particles within particle inspection zone 1140 on camera sensor 1720 (FIG. 17). The lens assembly may include one or more lenses. FIG. 18 illustrates the case where the lens assembly includes a weak (i.e., longer focal length) lens 1812 in combination with a strong (i.e., shorter focal length) lens 1814. In the example shown in FIG. 18, the strong lens is closer to the particle inspection zone than the weak lens. Optionally, the lens assembly 1725 may provide an electrically controlled focal length, for example, through a combination of a strong lens 1814 of fixed focal length and a weak lens 1812 whose focal length is electrically controlled.

Given a fixed location of camera sensor 1720 and of lens assembly 1725, increasing the net or effective focal length of the lens assembly 1725 moves the object focal plane down and decreasing the focal length moves the object focal plane up. That is by properly adjusting the focal length of the lens array 1725, one can bring into focus particles 1830. Furthermore, for larger particles or for optical arrangements with shallower depths of field, different adjustments of net focal length of the lens assembly 1725 can bring into focus different horizontal layers of a translucent particle like pollen grains. A set of images focused on different horizontal layers may provide information on the three-dimensional structure.

A lens with an electrically controlled focal length is generally more reliable than a moving mechanical mechanism. In other words, the reliability of modern electronic devices depends heavily in replacing moving mechanical mechanism with electronic mechanisms. From this perspective, it is very attractive to be able to be able to adjust in real-time the focus of the particle monitor's optical system with no or few mechanical movements, but instead control the focal length of the lens assembly purely electronically. Available lenses with electronically controller focusing tend to be weak lenses, too weak for identifying or discriminating particles. A weak lens in combination with a strong lens, however, can provide for reliability identifying or discriminating particles. In other words, this problem can be overcome with a strongly focusing lens assembly comprising a fixed strong lens and a weak electronically controlled lens.

In any case, an optical axis 1815 of the lens array intersects the particle inspection zone 1140 where particles 1830 such as pollen grains may be located. Such a lens assembly may be part of image capture hardware 226 of FIG. 2.

The camera sensor 1720 (FIG. 17) may be a black-and-white camera sensor, but in order to generate richer spectral information it is preferable that the camera sensor 1720 be color sensitive such as providing the ability to capture RGB (red-green-blue) color images. Indeed, the large volume or scale at which color camera sensors are manufactured as compared to black-and-white camera sensors have resulted in color camera sensors being less expensive than black-and-white camera sensors.

Both black-and-white cameras and color cameras provide information on the shape and structure of imaged objects, in other words the "morphology" of imaged objects. Color cameras also provide color information. The particle monitor can analyze an image to distinguish between types of particles through morphological features (e.g., is it round or rod like?, is it smooth or spikey?, is it large or small?, and so forth).

In another specific embodiment, the camera sensor 1720 may be a light-field camera sensor. These items represent embodiments of the image capture hardware 226 of FIG. 2.

Referring back now to FIG. 18, third hole 1740 within platform 1733 houses second illumination source 1755. The second illumination source includes a second light emitting element 1840, a quantum-dot film 1855, an optional diffuser 1850, and an optical shaft 1860. Second hole 1745 within the platform houses first illumination source 1750. A diffuser can be optional as the quantum-dots themselves will randomize the directions of emitted light.

Second light emitting element 1840 provides light reaching the particle inspection zone 1140 via light propagation approximately parallel to an illumination axis 1845. The illumination light may be visible light, UV light, or infrared light, or a combination thereof. As discussed, different types of particles can have different light absorption characteristics. For morphology analysis, visible light, or even one color of visible light can be sufficient. However, in some cases, a morphology analysis will not be sufficient to make a conclusive identification as there can be particles of different types but which have the same or similar geometric features. Color information becomes particularly interesting when it provides even a crude level of biochemical analysis without the delays and cost of wet-laboratory techniques. The differences in light absorption characteristics of different particles can be exploited to identify particles or discriminate between particles.

For example, pollen grains tend to have a yellowish color, so color as perceived by the human eye, or an RGB camera sensor under white light illumination is of value to check if a candidate pollen grain is indeed yellowish. Illuminating with white light and capturing the resulting scene provides a useful indication of the colors of the particles that have been captured. Grass pollens tend to have bio-molecule chlorophyll-a and hence a pollen grain with visible light absorption peaks of chlorophyll-a is likely to be a grass pollen.

Fluorescence under UV illumination is a marker of biomolecules that can be used to distinguish between organic and inorganic particles. Biochemcial information can be provided by UV fluorescence. Fluorescence is a property some molecules have in which they absorb light of one color and emit light of a different color (e.g., different wavelength). While UV light might not be detected by the camera sensor, the resulting fluoresced or emitted light from the particle may be detected by the camera sensor. As another example, illumination in near infra-red (near enough in wavelength to visible light to be detected by the camera sensor) may provide useful information in regards to identifying particles or discriminating between particles.

Camera sensor 1720 (FIG. 17) may image scattered light, fluorescent light, or both. Light scattering, where photons bounce off objects in a different direction without changing their wavelength/color is the workhorse of light imaging. With rare exceptions, this is how we see objects in our daily lives when we use our eyes. Just as with our human eyes, in the particle monitor's basic object shape and color information comes from light scattering. UV fluorescence is less common (such as in "black lights") and is of interest in particle identification and discrimination because UV fluorescence indicates the presence of biological materials and may provide information about the types of biological materials.

Optionally, to provide a more uniform illumination of the particle inspection zone 1140, a diffuser 1850 may be placed along the illumination axis between second light emitting element 1840 and the particle inspection zone 1140. The second light emitting element 1840 and the diffuser 1850 may be mechanically connected with an optical shaft 1860 forming a rigid illumination-source sub-assembly.

Preferably, optical shaft 1860 has optical wave-guiding properties so as to more efficiently direct light from second light emitting element 1840 to particle inspection zone 1140. Third hole or illumination channel 1740 may penetrate platform 1733 in order to hold the rigid illumination-source sub-assembly in place and to remove material around the illumination axis 1845.

As shown in the example of FIG. 18, there is a 55-degree angle between the optical axis 1815 and the illumination axis 1845; however other angles are also possible. This includes angles larger than 90-degrees if the adhesive-coated tape and the tape guide 1120 under the particle inspection zone 1140 are at least partially transparent. Larger than 90-degree illumination angles are also an option for alternate embodiments for which sampled particles are captured on transparent glass or plastic slides instead of with adhesive-coated tape. FIG. 18 illustrates just one possible azimuthal angle for an illumination axis 1845; optionally any azimuthal angle may be used. Such illumination options represent embodiments of illumination hardware 224 of FIG. 2.

Light emitting element 1840 may be an LED (light emitting diode) including possibility an OLED (organic light emitting diode), or a laser, or any other type of light generating device. Furthermore, light emitting element 1840 may be of the downstream end of an optical fiber bringing light from a light emitting element mounted elsewhere. Light emitting element 1840 may provide a wide range of wavelengths, such as with a white-LED, or provide a narrow range of wavelengths, such as with a laser. To provide more information for recognition of particle types, there can be multiple illumination sources.

The holes formed in the platform for light sources, optical shaft, or both may have a cross-sectional shape of a circle. In other embodiments, the cross-sectional shape of a hole may be an oval, square, rectangle, or other shape. In some applications it may be useful to use cross-sectional hole shape as part of a keying system that controls what type of illumination source sub-assemblies are inserted into which holes. A light source may include a light emitting element and optical fiber. The use of optical fiber allows the light emitting element to be located anywhere within the particle monitor and not necessarily within the platform. The ability to locate the light emitting element anywhere within the particle monitor helps to facilitate a compact design.

For example, the light emitting element may be located in the base of the platform. An end of an optical fiber may be connected to the light emitting element. An opposite end of the optical fiber may be connected to a hole or opening in the platform. The optical fiber transmits light from the light emitting element to the platform or particle inspection zone so that the collected particles can be illuminated for the camera sensor. There can be multiple strands of optical fiber. A cross-sectional shape of the optical fiber may be a circle or other shape.

As previously stated, image capture hardware 226 of FIG. 2 may advantageously take advantage of commercially available camera sensors. Due to mass market demand for color digital cameras including cameras built into smart phones, sophisticated RGB (red, green, blue) camera sensors are available at relatively low cost. A feature of the system allows for the use of such relatively low-cost camera sensors for an automated pollen detection systems based on optical imaging of sampled pollen. Pollen color information is of interest for differentiation between types of pollen and other allergens as well as differentiation between allergens and background non-allergenic particulates. Now let us take a closer look at the spectral characteristics mass produced camera sensors.

Figure 19:
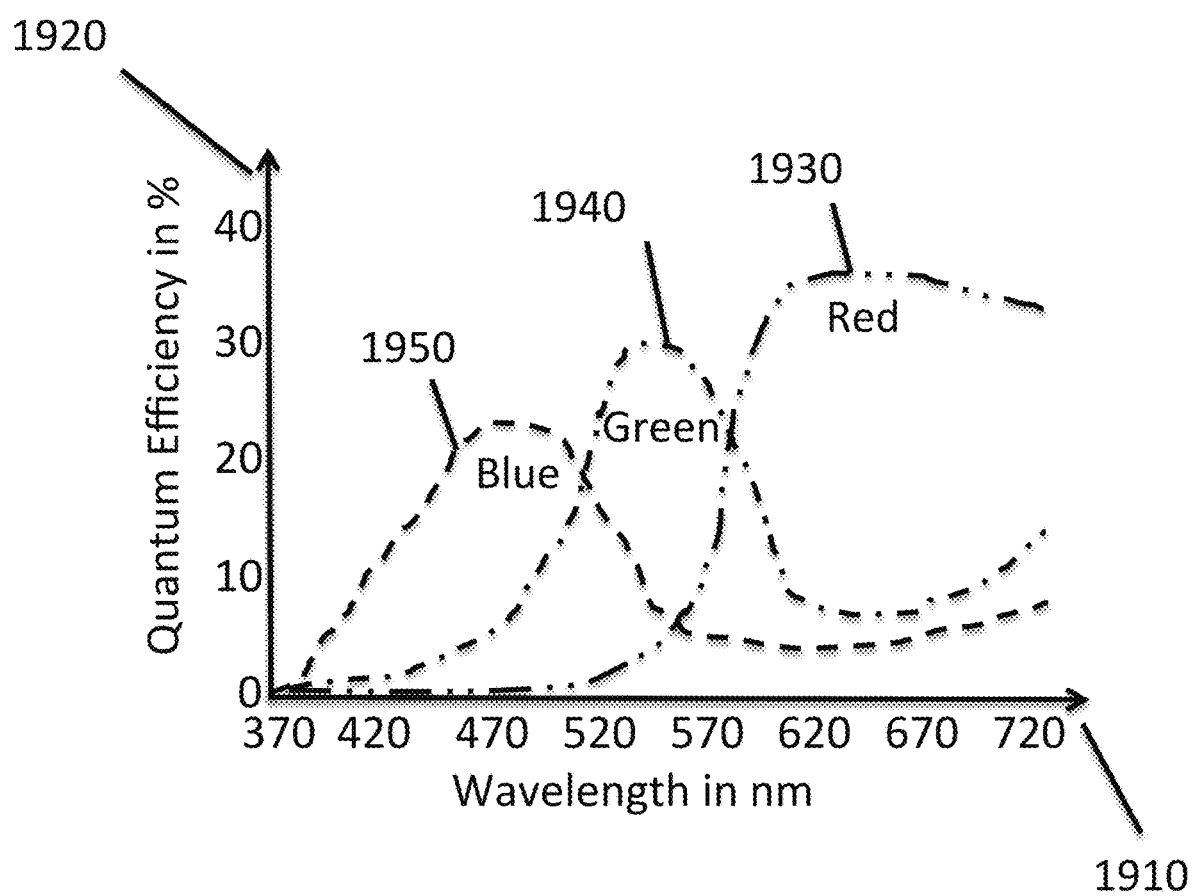
FIG. 19 is a graph showing spectral characteristics typical of an RGB camera sensor.

FIG. 19 illustrates spectral characteristics typical of an RGB camera sensor such as may be found in consumer-level digital cameras. Horizontal axis 1910 represents optical wavelengths within the visible spectrum from violet at the left to red at the right. Vertical axis 1920 represents the quantum efficiency (percentage of photons resulting in one electron of current) of a camera sensor sub-pixel. The dot-dot-dashed curve 1930 represents the spectral response of red or "R" sub-pixels of an RGB camera sensor. The dot-dashed curve 1940 represents the spectral response of green or "G" sub-pixels of an RGB camera sensor. The dashed curve 1950 represents the represents the spectral response of blue or "B" sub-pixels of an RGB camera sensor.

These spectral responses are determined in large part by color filters placed in front of sub-pixels as part of the construction of the camera sensor. Often, the color filters include more green elements as compared to red or blue elements. This is because the human visual system peaks in sensitivity in the green spectral region (e.g., peaks at approximately 550 nm wavelength). Thus, the abundance of green sensor pixels in the imaging device allows for approximating the color response of the human visual system.

As can be seen, the spectral response curves are quite broad and overlapping. For conventional digital camera purposes, this has the advantage that there is no visible light wavelength for which a color digital camera is blind. However, from the perspective of quantitative spectral analysis, the broad and overlapping spectral characteristics is a disadvantage because the absorption characteristics of particles of interest (e.g., grass pollen) may be much more narrow. Thus, in some cases, it can be very difficult to distinguish and discriminate different particle types based on color using a broad and overlapping emission spectra to illuminate the particles.

A close look at the spectral profiles in FIG. 19 reveals a significant amount of what may be described as "color crosstalk." For example, even red light at a wavelength of 700 nm will not only excite red RGB pixels with a quantum efficiency of about 35 percent, but also excite "green" RBG pixels with a quantum efficiency of order 10 percent and excite "blue" RGB pixels with a quantum efficiency of order 5 percent. It is an over-simplification to say that "red" RGB pixels detect "red" light, "green" RGB pixels detect "green" light and "blue" RGB pixels detect "blue" light. For a deeper appreciation of the system discussed herein, and in particular various embodiments of the illumination hardware 224 (FIG. 2) presented further below, it is useful to keep this fact in mind.

In conventional applications of RGB camera sensors, such as in color digital cameras, color digital microscopes, and so forth, it is taken for granted that associated lens assemblies must be achromatic so that the red, green and blue sub-pixel images are all brought to an equally sharp focus. RGB camera sensors are conventionally associated with achromatic optics. The requirement that RGB camera optics be achromatic adds to the complexity of the optics, and hence its cost, particularly if a relatively large aperture is required.

Applicants have appreciated, however, the advantages provided by quantum dots for a particle (e.g., pollen or mold spore) imaging system. At present, from a commercial perspective, quantum dots are a new and unconventional technology. With the recent development of quantum dot films for use in backlight systems of liquid crystal displays (LCDs), only recently have quantum dots started to go beyond the research lab and become a significant commercial technology. One example of a company developing quantum dots is Nanosys of Milpitas, Calif. (www.nanosys-inc.com). As mass production of quantum dots ramps up, it is reasonable to assume that there will be dramatic cost reductions for quantum-dot based illumination sources, such as quantum-dot enhanced LED light sources.

Quantum dots are very small particles of semiconductor materials that are only a few nanometers in diameter. This small size affects the band gap energy, and hence light emission wavelength, of the quantum dot. By adjusting the quantum dot diameter during its manufacture, the wavelength of its emitted light may be tuned. A quantum dot (QD) is a nanocrystal made of semiconductor materials that is small enough to exhibit quantum mechanical properties. Different sized quantum dots emit different color light due to quantum confinement.

In other words, electronic characteristics of a quantum dot are closely related to its size and shape. For example, the band gap in a quantum dot which determines the frequency range of emitted light is inversely related to its size. In fluorescent dye applications the frequency of emitted light increases as the size of the quantum dot decreases. Consequently, the color of emitted light shifts from red to blue when the size of the quantum dot is made smaller. This allows the excitation and emission of quantum dots to be highly tunable. Since the size of a quantum dot may be set when it is made, its electronic and optical properties may be carefully controlled. Quantum dot assemblies consisting of many different sizes, such as gradient multi-layer nanofilms, can be made to exhibit a range of desirable emission properties.

Figure 20:
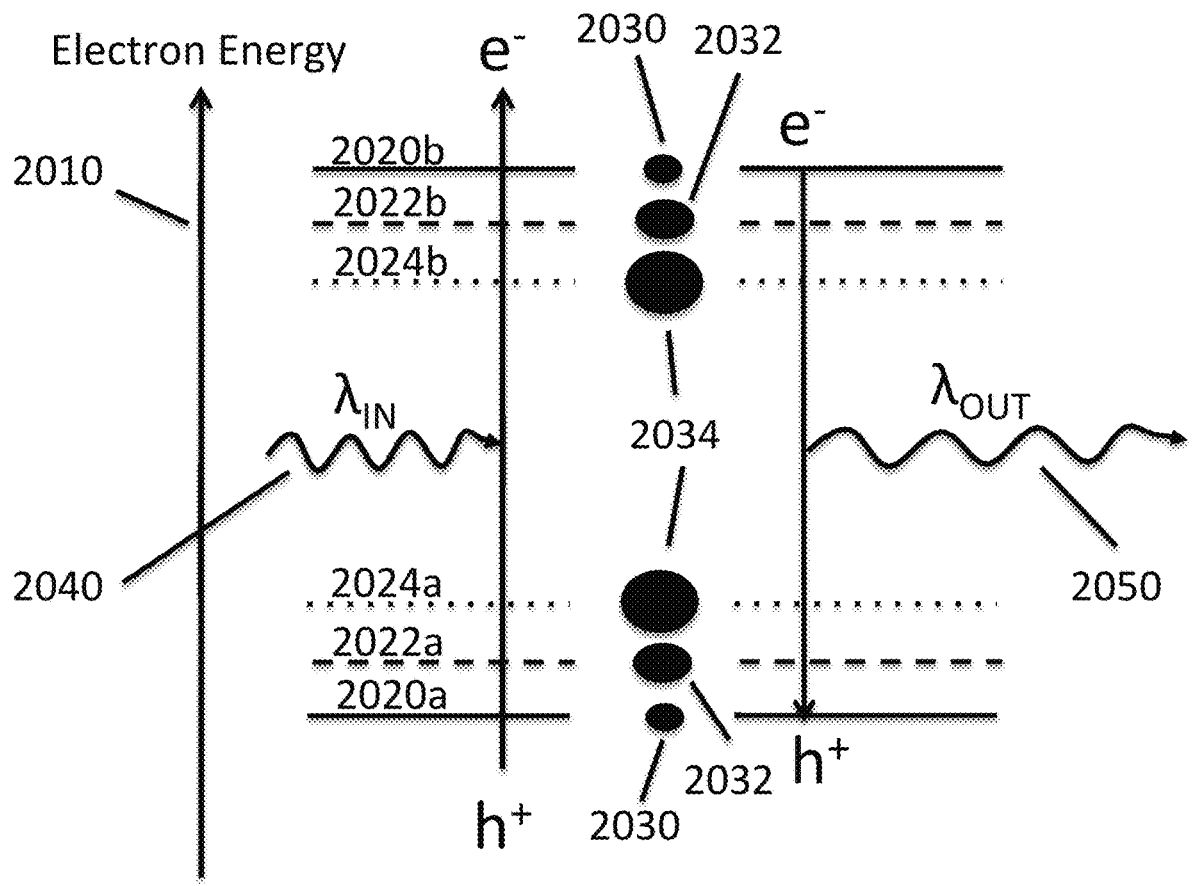
FIG. 20 shows the expansion of band-gap of energy levels for small quantum dots due to the quantum confinement effect.

Specifically, as schematically illustrated in FIG. 20, its small dimensions affect its band gap. FIG. 20 shows quantum dots 2030, 2032, and 2034 in varying sizes. There are incoming photons of light 2040 into the quantum dots and outgoing photons of light 2050 from the quantum dots. The vertical direction 2010 in FIG. 20 represents electron energy (e.g., a vertical electron energy axis). The horizontal dotted, dashed and solid lines 2024a-b, 2022a-b, and 2020a-b, respectively, represent the band gap limits of quantum dots of small, smaller and even smaller diameters respectively.

The lower sets of horizontal lines represent the top of the valence band and the upper sets of horizontal lines represent the bottom of the conduction band. A photon of light may be absorbed if its energy exceeds the band gap energy, that is, if its wavelength $\lambda_{IN}$ is sufficiently short. When such a photon is absorbed, a electron $e^-$ previously in the valence band is excited into the conduction band, leaving a hole $h^+$ in the valence band. This is illustrated to the left of FIG. 20.

The resulting electron $e^-$ and hole $h^+$ quickly loose energy until they are at the bottom of the conduction band and at the top of the valence band, and then the electron $e^-$ at the bottom of the conduction band will emit a photon of wavelength $\lambda_{OUT}$ loosing sufficient energy to occupy the hole$^+$ in the valance band. This is illustrated to the right of FIG. 20 for the case of the smallest of the three quantum-dot diameters considered in the figure. The wavelength $\lambda_{OUT}$ of the lower energy re-emitted photon is longer than the wavelength of the higher energy absorbed photon $\lambda_{IN}$.

Such a process of photon absorption at a shorter wavelength followed by the emission of a photon at a longer wavelength is an example of fluorescence. The mechanisms illustrated in FIG. 20 may be summarized by saying quantum dots fluoresce at wavelength $\lambda_{OUT}$ when excited by light of a shorter wavelength $\lambda_{IN}$. A key observation is that while quantum dots may absorb photons of a broad range of wavelengths corresponding to any photon energy exceeding the band gap, the emitted or fluorescent photons are approximately monochromatic with a wavelength corresponding to the band gap energy. A desired emitted wavelength $\lambda_{OUT}$ may be provided by appropriately tuning the diameter of the quantum dots during their manufacture.

The ability to fabricate quantum dots corresponding to any desired color or wavelength has been well demonstrated. In a specific embodiment, a particle monitor includes "size-tuned quantum dots." In this specific embodiment, the emission wavelength is mainly tuned via manufacturing control of particle size.

In another specific embodiment, a particle monitor includes "composition-tuned quantum dots." In this specific embodiment, the emission wavelength is mainly tuned via manufacturing control of the particle composition (e.g., adjusting the material composition in order to control the quantum-dot emission wavelength). Composition-tuned quantum dots may be composed of a mixture of $CsPbI_3$, $CsPbCl_3$ and $CsPbBr_3$ where (referring to the periodic table) Cs is cesium, Pb is lead, I is iodine, Cl is chlorine and Br is bromine. By mixing these three compounds in different proportions, the nanoparticle's bandage and hence emission wavelength may be tuned.

In some cases, "composition-tuned" quantum dots can provide a narrow spectral width ("<25 nm FWHM" or less than 25 nm full width half maximum) because there is no requirement to precisely control the size of the quantum-dot particles (as their emission wavelength is controlled more by composition than size), but instead by precisely controlling the composition of the quantum dots. Quantum dots may be provided for UV or infrared wavelengths. Particle sizes (e.g., diameter) of composition-tuned quantum dots may range from about 5 nm to about 50 nm. The size may be greater than 50 nm or less than 5 nm.

Figure 21:
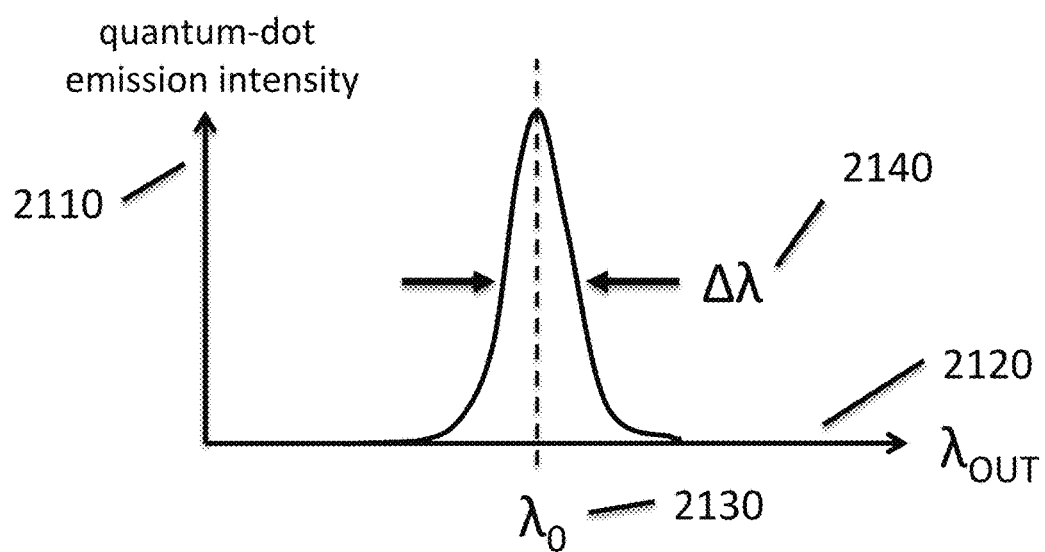
FIG. 21 is a graph showing a quantum-dot emission spectrum.

Quantum dots may be defined as nano-scale particles (<1 um in largest dimension) of semi-conductor material with a band gap controlled peak emission wavelength. In embodiments where an approximately monochromatic illumination is desired quantum dots with a narrow distribution of sizes may be used. A corresponding spectral distribution is schematically shown in FIG. 21. FIG. 21 shows a vertical axis 2110 and a horizontal axis 2120. The vertical axis indicates light intensity. The horizontal axis indicates a wavelength of emitted light. The spectrum has a peak wavelength 2130 and a wavelength spread 2140. The peak wavelength can be tuned by adjusting the band gap which in turn is controlled by adjusting the quantum dot size. A narrow wavelength spectrum helps to identify particles such as pollen based on color.

Full-width-at-half-maximum (FWHM) spectral widths of $\Delta\lambda$=50 nm, and even 25 nm, are presently achieved by commercial quantum dot suppliers. Narrower spectral widths may well be possible with quantum dots in the future. For many purposes, such as interferometry measurements, a spectral widths of $\Delta\lambda$=25 nm is far from monochromatic and the much narrower spectral widths of lasers are required.

Figure 22:
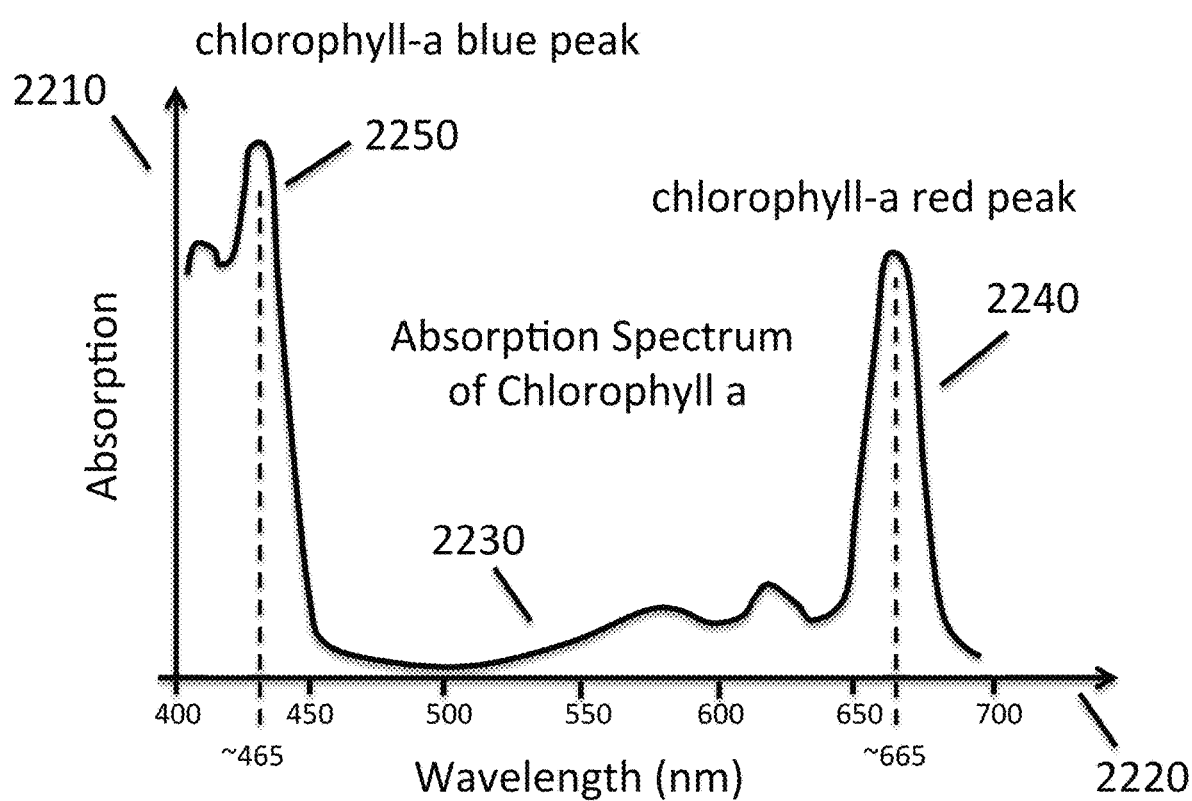
FIG. 22 is a graph showing the absorption spectrum of chlorophyll-a.

However, fortuitously, the spectral widths that are possible from illumination sources using quantum dots is a good match to the spectral widths of, for example, the absorption peaks of chlorophyll-a as shown in FIG. 22. FIG. 22 shows an absorption spectrum of chlorophyll-a. With a vertical axis 2210 representing absorption strength and a horizontal axis 2220 for light wavelength, a curve 2230 shown in FIG. 22 represents the absorption spectra of chlorophyll-a.

This absorption spectrum has a pronounced "chlorophyll-a red peak" 2240 and a pronounced "chlorophyll-a blue peak" at 2250. In the plot above the two absorption peaks are centered near 665 nm and 465 nm wavelengths. As one of skill in the art would recognize, the solvent solution environment of the chlorophyll-a has a significant effect on the locations of the peaks. Thus, depending upon factors such as the solvent solution environment, the location of the peaks may differ such as for chlorophyll-a on grass pollen. It should be appreciated that the principles of choosing quantum-dots based on the locations of the peaks remain the same.

The presence of chlorophyll-a distinguishes grass pollens from other pollens as well as other particles, and hence a quantum-dot illumination source tuned to an absorption peak of chlorophyll-a is of interest in the identification of allergenic grass pollens.

Quantum dots may be made of binary compounds (e.g., lead sulfide, lead selenide, cadmium selenide, cadmium sulfide, indium arsenide, and indium phosphide) or ternary compounds (e.g., cadmium selenide sulfide). Quantum dots can contain as few as 100 to 100,000 atoms within the quantum dot volume, with a diameter of 10 to 50 atoms. This corresponds to about 2 to 10 nanometers.

Quantum dots absorb photons (perhaps with a broad range of wavelengths) from a light source such as an LED, and then emit photons (of a longer wavelength) with a narrow spectral spread. Alternatively, quantum dots may be excited electronically and serve as the original source of photons. For example LEDs (more specifically organic light emitting diodes or OLEDs) may be modified so that its light originates from electron-hole recombination within quantum dots. Whether quantum dots are used to create light, or to modify light, the result is light with narrow spectral peaks.

In a specific embodiment, a method includes identifying an absorption peak of a particle of interest, and providing a quantum dot containing product having a set of quantum dots configured to correspond to the absorption peak of the particle of interest. The quantum dot containing product may be a film, LED, tape, adhesive, backing material for an adhesive, or disk. The quantum dot containing product may be installed within a particle monitoring device.

Figure 23:
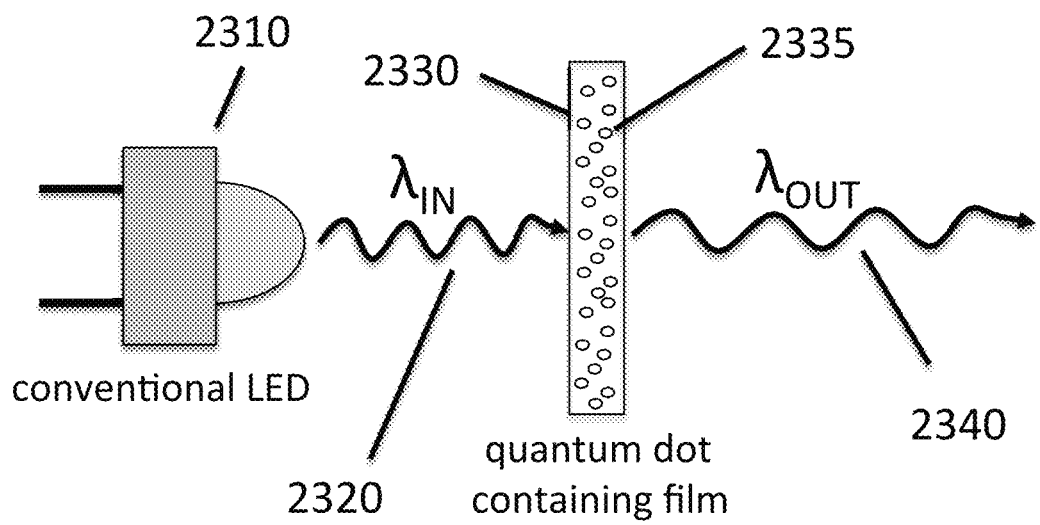
FIG. 23 shows a quantum-dot containing film wavelength shifting light from a conventional LED.

FIG. 23 shows a conventional LED 2310 and a film 2330 containing quantum dots 2335. The film includes a matrix of transparent material in which the quantum dots have been dispersed throughout. The material may include a clear or transparent polymer, plastic, glass, acrylic, silicone, adhesive, epoxy, or resin.

FIG. 23 illustrates the film intercepting photons of wavelength $\lambda_{IN}$ 2320 from the conventional light emitting diode (LED). Photons from the LED are absorbed by quantum dots that then fluoresce at a longer wavelength $\lambda_{IN}$ 2340.

In a specific embodiment, the LED includes a blue LED, but can be any light emitting element that emits a wavelength shorter than the desired output wavelength. The film or other transparent medium containing quantum dots converts between input and output wavelengths via the mechanisms shown in FIG. 20. A blue LED is desirable because a quantum dot can absorb a higher energy photon (of shorter wavelength) and convert it to a photon of lower energy (of longer wavelength). For example, a quantum dot of a particular diameter can convert blue light to red light because the blue light is of a higher energy than the red light. As another example, a quantum dot of another different diameter can convert blue light to green light because the blue light is of a higher energy than the green light. Thus, starting with a high energy light (e.g., a blue LED), increases the range of colors that can be produced using quantum dots.

Referring back to FIG. 18, it should be appreciated that the mechanical schematic shown in FIG. 18 of the quantum dots is merely an example of one particular implementation of particle monitor 105. In other implementations, other similar and equivalent elements and functions may be used or substituted in place of what is shown.

For example, FIG. 18 shows light emitting element 1840 (which may be a conventional LED) emitting light through quantum-dot film 1855 and optionally through diffuser 1850. The quantum dots, however, may be integrated with other components and give the same functionality. Specifically, rather than having a separate quantum-dot film and diffuser, the diffuser itself may contain the quantum dots and the quantum-dot film may be omitted with the result that the color of light illuminating the particle inspection zone 1140 is determined by the nature of the quantum dots in the diffuser and not by the color of light generated by light emitting element 1840.

In another specific embodiment, a polarizer (not shown) may instead or additionally be included along the illumination axis 1845 so that the particle inspection zone is illuminated with polarized light. A similar effect may be obtained with greater quantum efficiency if the diffuser 1850 contains quantum dots (or "quantum rods") in the shape of elongated ellipsoids rather than spheres, and if the major axes of the elongated ellipsoids are aligned with the electric field of the desired light polarization. A polarizer may instead or additionally be included along the optical axis 1815 in order to analyze polarization of light scattered by particles 1830. Polarized light can help to increase contrast between the background and particles that have been collected on the tape.

Figure 24:
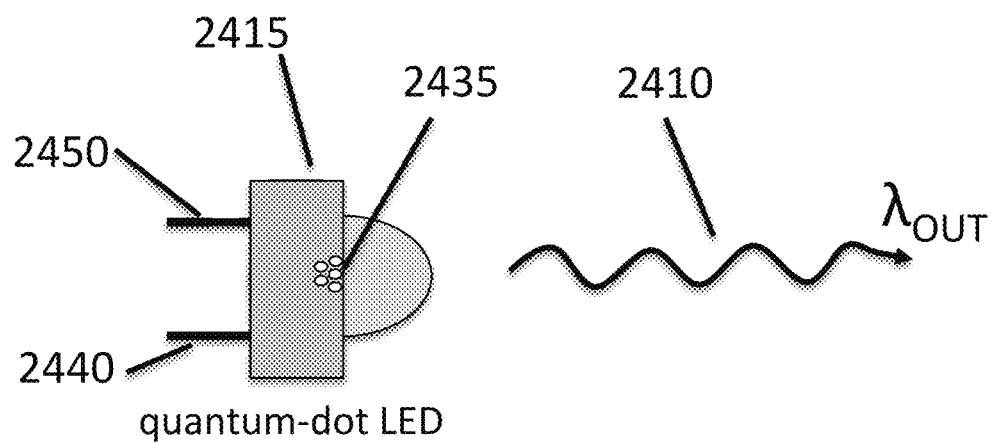
FIG. 24 shows a quantum-dot containing LED directly generating light of a desired wavelength.

As another example, quantum dots may serve to convert electrical energy to light energy within the LED itself. More particularly, FIG. 24 illustrates a direct generation of photons of wavelength $\lambda_{OUT}$ 2410 from a quantum-dot LED 2415. Within such an LED, the electron e⁻ and hole h⁺ to the right of FIG. 20 are provided by associated electronic circuitry and are not the result of photon absorption. In particular electrical current go from lead 2440 through quantum dots 2435 and to lead 2450. When an electrical current passes through quantum dots 2435, electrons combine with holes generating photons.

Figure 25:
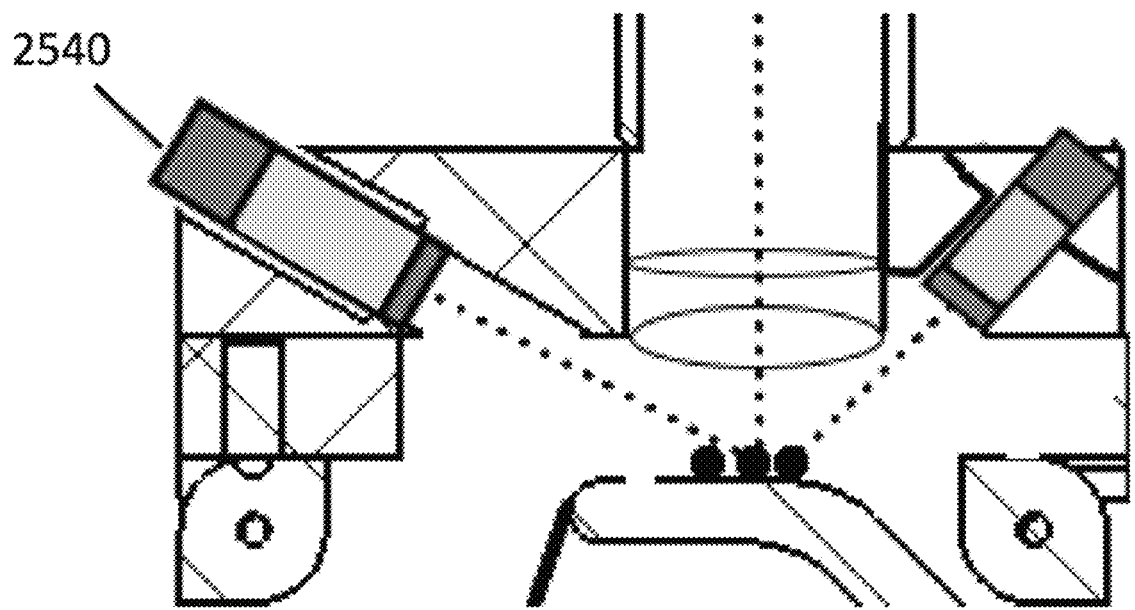
FIG. 25 shows an enlarged side-view cross-section of a particle monitor having a quantum-dot LED according to another specific embodiment.

More particularly, FIG. 25 shows particle monitor 105 with a quantum-dot LED. The view of the particle monitor shown in FIG. 25 is similar to the view of the particle monitor shown in FIG. 18. In FIG. 25, however, a light emitting element 2540 is a quantum-dot LED and the quantum-dot containing film shown in FIG. 18 has been omitted. The conventional LED shown in FIG. 18 has been replaced in FIG. 26 with a quantum-dot LED. Incorporating quantum dots within the LED itself can be more efficient that using a film having quantum dots. For example, when light strikes a film having quantum dots, the converted light may be emitted in any number of different directions (including backwards towards the light emitting element) rather than in a direction towards the particles. Thus, incorporating quantum dots within the actual light emitting element itself (e.g., an LED) can result in more light being directed towards illuminating the particles. A film having quantum dots, however, might be less expensive to produce than an LED having quantum dots.

Figure 26:
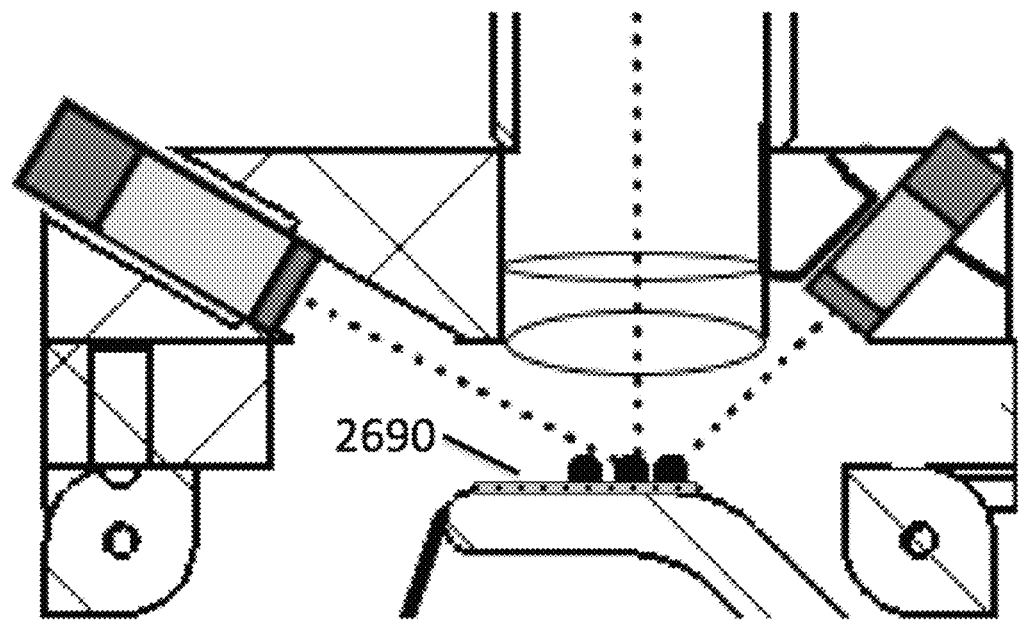
FIG. 26 shows an enlarged side-view cross-section of a particle monitor having a quantum-dot adhesive tape according to another specific embodiment.

FIG. 26 shows yet another embodiment of particle monitor 105 where the quantum dots have been dispersed within an adhesive coated tape 2690 of a collection cartridge. The view of the particle monitor shown in FIG. 26 is similar to the view of the particle monitor shown in FIG. 18. In FIG. 26, however, the quantum-dot containing film shown in FIG. 18 has been omitted and the quantum dots have been dispersed within the adhesive coated tape. The quantum dots may be dispersed within an adhesive of the tape, a backing material of the tape, or both.

Quantum-dots may be dispersed in the adhesive of the tape. In this specific embodiment, the adhesive may be clear or transparent. Alternatively, the tape may be a clear tape and the quantum dots may be placed within a fixed supporting structure (such as dispersed within the tape guide structure of the collection cartridge or, more particularly, second segment 1382B—FIG. 13) behind or below the adhesive coated tape. In this specific embodiment, the second segment of the tape guide may be manufactured as a unit separate from the other segments (first and third segments) of the tape guide. The second segment may include a clear or transparent matrix of material having a set of quantum dots dispersed within. The second segment may then be joined or connected to the third segment to form the tape guide. In other words, the quantum dots may be positioned below the collected particles. From an optics perspective, the former approach is advantageous because the quantum dots are most immediately behind the particles of interest. However, making quantum dots part of the adhesive coating recipe can be expensive. From a cost perspective, the latter approach may be more attractive. Placement of quantum dots may change as the cost of quantum dots drops with time.

Thus, as illustrated in FIGS. 18, 25, and 26 there can be multiple distinct ways to utilize quantum dots as a means of controlling the color properties of light illuminating the particle inspection zone 1140. As another example, quantum dots may be dispersed within a lens case or lamp shade of an LED.

Figure 27:
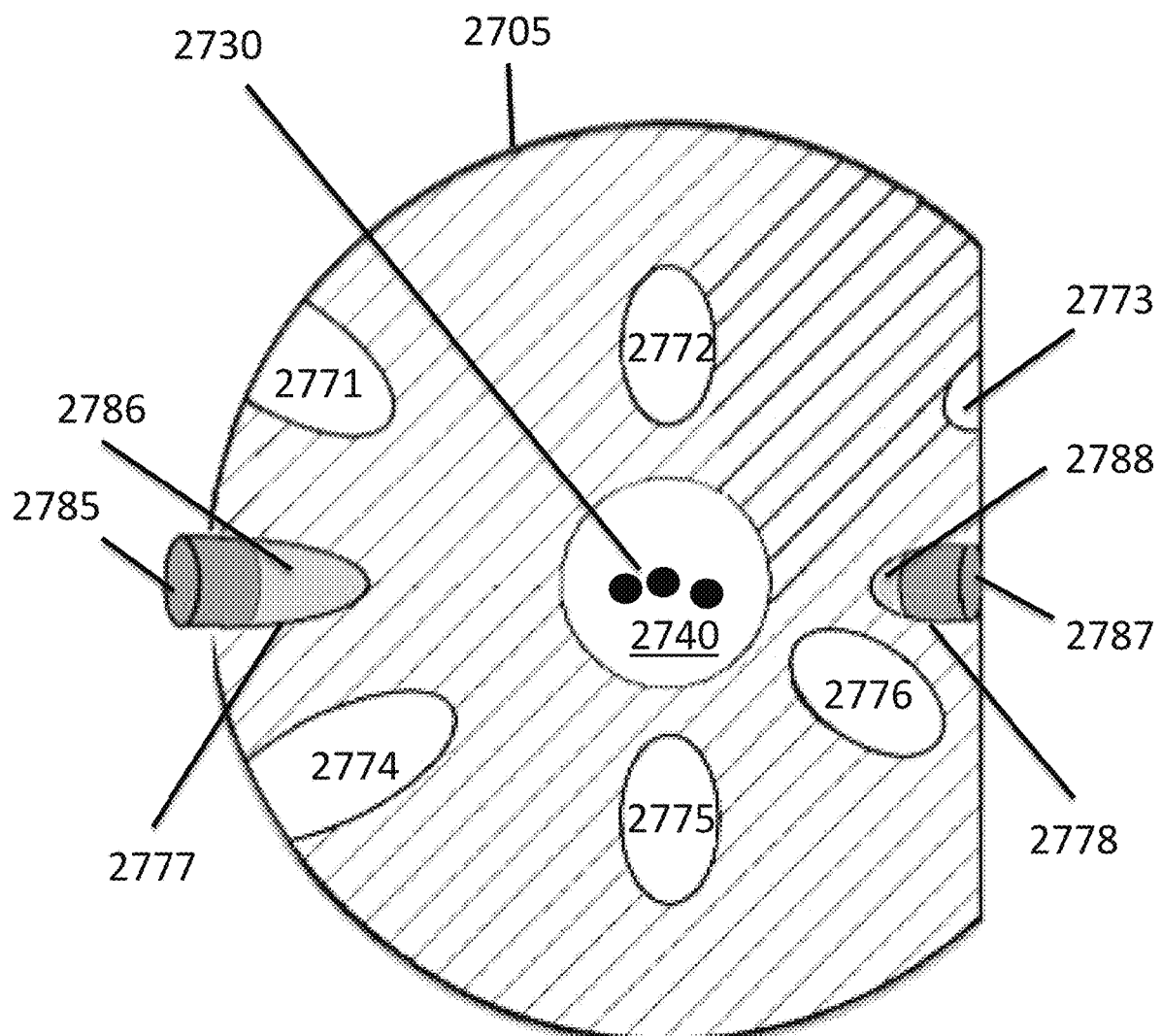
FIG. 27 shows a top view of an inspection platform of a particle monitor according to another specific embodiment.

FIG. 27 shows a top view of a platform 2705 of another specific embodiment of a particle monitor. FIG. 27 illustrates an example with eight illumination sources or channels 2771, 2772, 2773, 2774, 2775, 2776, 2777, and 2778. The illumination channels have been drawn in FIG. 27 with varying shapes to represent different azimuthal angles. Each illumination channel may include a light emitting element and an optical shaft. For example, illumination channel 2777 includes a light emitting element 2785 connected to an optical shaft 2786. Illumination channel 2778 includes a light emitting element 2787 connected to an optical shaft 2788. An illumination source may or may not be associated with a set of quantum dots. An illumination source may emit visible light (e.g., wavelengths ranging from about 390 nm to about 700 nm), UV light (e.g., wavelengths ranging from about 10 nm to about 380 nm), or infrared light (e.g., wavelengths ranging from about 700 nm to about 1 mm).

The light emitting elements and optical shafts for the remaining illumination channels have been omitted for clarity. In other words, additional light emitting elements (not shown) may be installed in additional illumination channels 2771-2776. Each illumination source has an illumination axis that intersects the particle inspection zone 2740. Illumination axes corresponding to different illumination sources may vary in azimuthal angle as well as angle with respect to an optical axis passing through a particle inspection zone 2740 having particles 2730, through a lens assembly, and to a camera sensor. Having may different illumination axes further provides for other dimensions of analysis. For example, the lengths of different shadows resulting from shining light at different angles can indicate the height of a particle.

The light emitting elements may vary in the nature of their emitted light. For example, illumination hardware 224 (FIG. 2) may provide local processor 240 many illumination options such as white-light illumination, UV illumination, infrared illumination, and visible light illuminations of various color characteristics. Local processor 240 may activate individual light sources one-at-a-time, or activate two or more light emitting elements simultaneously or concurrently.

Figure 28:
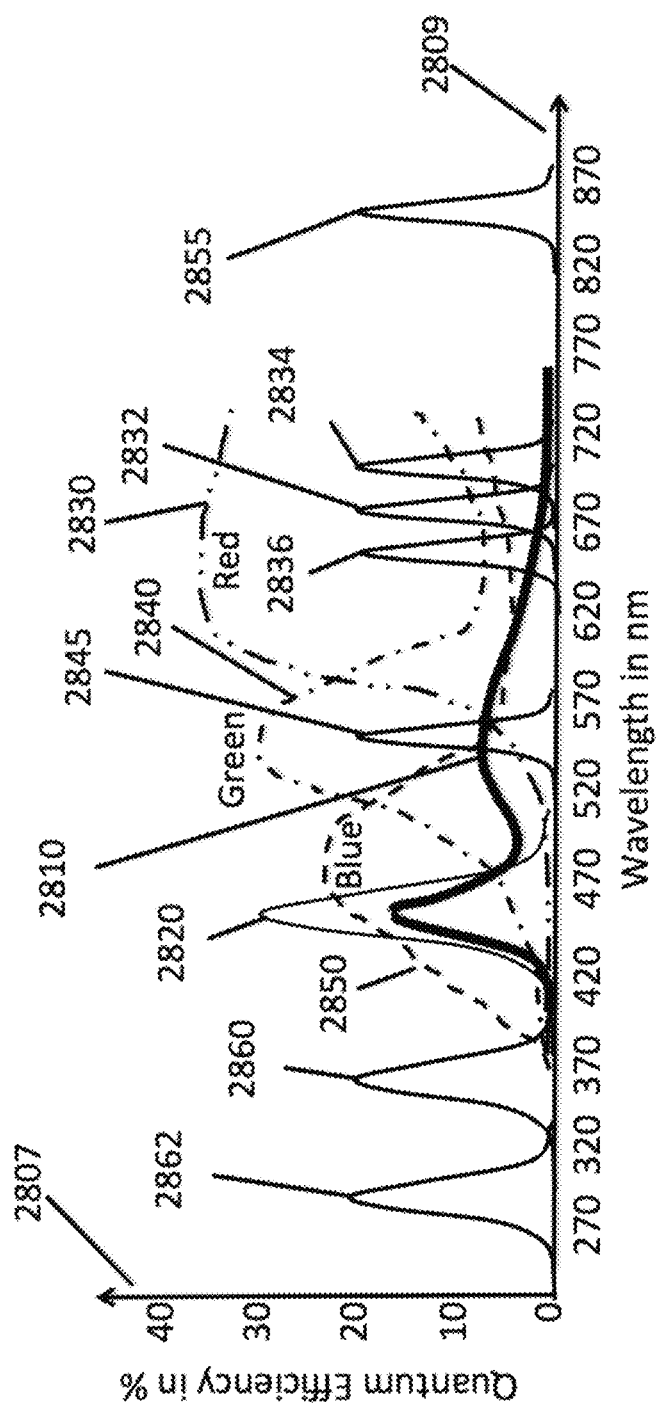
FIG. 28 shows a plot combining camera-sensor sub-pixel spectral characteristics as shown in FIG. 19 with illumination source spectral characteristics.

FIG. 28 shows a plot combining camera-sensor sub-pixel spectral characteristics as shown in FIG. 19 with illumination source spectral characteristics. Vertical axis 2807 represents the quantum efficiency (percentage of photons resulting in one electron of current) of a camera sensor sub-pixel. Horizontal axis 2809 represents optical wavelengths within the visible spectrum from violet at the left to red at the right. The dot-dot-dashed curve 2830 represents the spectral response of red or "R" sub-pixels of an RGB camera sensor. The dot-dashed curve 2840 represents the spectral response of green or "G" sub-pixels of an RGB camera sensor. The dashed curve 2850 represents the represents the spectral response of blue or "B" sub-pixels of an RGB camera sensor. FIG. 28 shows the quantum efficiency curves for red, green and blue camera sensor sub-pixels. Relative to FIG. 19, the horizontal wavelength axis has been extended in FIG. 28 to include ultraviolet (UV) light at shorter wavelength and near infrared (IR) light at longer wavelengths.

FIG. 28 adds emission spectra of value illumination sources (for which the vertical axis has arbitrary units unrelated to quantum efficiency). Heavy solid curve 2810 is representative of the emission spectra of white-light LEDs. White-light LEDs are fundamentally blue LEDS, hence the emission peak in the blue, to which phosphors have been added to convert much of the blue light into a broad spectrum of longer wavelength light, hence the broad spectral peak to the right.

In many embodiments, such a white-light LED is the primary illumination source used to produce images for particle shape (morphology) analysis as well as a basic, first pass color analysis. This first pass color analysis is largely based on color as perceived by the human eye. It is worth keeping in mind, there is much more color information that can be perceived by the human eye.

Curve 2820 represents the emission spectra of a blue LED. While a white-light LED may be used to excite fluorescence of quantum-dots, it is more efficient to do so with a blue LED.

Curve 2832 represents the emission spectrum of quantum dots tuned during manufacture to emit red light at the absorption peak of chlorophyll-a within grains of grass-pollen. This "chlorophyll-a red" emission may be fluorescently exited by, for example, light from a blue LED, or excited directly electronically. Curves 2834 and 2836 illustrate spectra of quantum-dots tuned to emit light of wavelengths just above and just below the chlorophyll-a red wavelength.

A strong signature for the presence of chlorophyll-a is strong optical absorption of red light of the spectrum of curve 2832 but not of red light of the spectrum of curves 2834 and 2836.

An approximation of full spectral analysis of objects viewed with a camera sensor is possible with a sufficient number of quantum-dot illumination sources. Consider, as an example, extending the set of spectral curves 2834, 2832 and 2836 in both directions of increasing and decreasing wavelength in order to cover the entire visible spectrum. While not providing the same fine color resolution of a scientific grade spectrometer, a device with between 10 and 100 quantum-dot illumination sources may still provide an approximation of a full spectral analysis at each camera-sensor pixel location that provides useful information at relatively low cost.

Even for analysis of shape information (morphological analysis) that does not make use of color, the narrow spectral widths of quantum-dot emission may be helpful. Consider, as an example, a lens system that is subject to chromatic aberration, either as a cost saving measure or due to the use of an electronically controlled variable lens (in combination with a stronger fixed lens). In such a scenario, illumination with the green quantum-dot spectrum of curve 2845 will largely eliminate chromatic aberration effects and produce sharper images for morphological analysis.

Useful spectral information is not limited to the visible spectrum. For example, it may be of interest to illuminate particles of interest with a near infrared LED, for example, at a wavelength of 850 nm. As illustrated by curve 2855, sufficiently "near" infrared light, that is with sufficiently short wavelengths, may still be transmitted by common lens materials and be detectable by a conventional camera-sensors. In some applications, the near infrared properties of particles may be of value.

Typically, common lens materials block ultraviolet light. This may be used to advantage when particles of interest are illuminated by UV light, resulting in fluorescent light of longer wavelengths that are detected by the camera-sensor while the illuminating UV is not. This isolates the interesting fluorescence signal from simply scattered UV light. UV fluorescence is of particular value in distinguishing between inorganic particles and particles of biological origin.

Curve 2860 is representative of common 365 nm UV LEDs. This UV wavelength is sufficiently short to fluorescently excite nicotinamide adenine dinucleotide (NADH) molecules, but too long to excite other bio-molecules, hence a 365 nm UV LED can be used to probe NADH content of biological particles of interest.

Curve 2862 represents the emission spectra of a shorter wavelength UV LED, with the ability to fluorescently exits trytophan and other aromatic amino acids within proteins.

By probing both NADH and protein content, a pair of UV LEDs provides a two-dimensional probe of particle biochemistry. In a like manner and for similar purposes, additional UV LEDs may be included where each UV LED (or cluster of UV LEDs) emits UV light of differing energies. While much less powerful then a wet-laboratory bio-assay, such optical probing of particle biochemistry has the advantage of providing immediate, if crude, biochemical information, with which to aid in real-time particle type discrimination.

In a specific embodiment, a feature of the system enables the use of low-cost lens systems within particle imaging systems by relaxing the requirements for achromatic optics. An achromatic lens is a lens that is designed to limit the effects of chromatic aberration. Quantum dots can help with chromatic aberration. Generally, however, not all colors will be in complete focus and the performance of an achromatic lens can vary in proportion to its cost.

Figure 29:
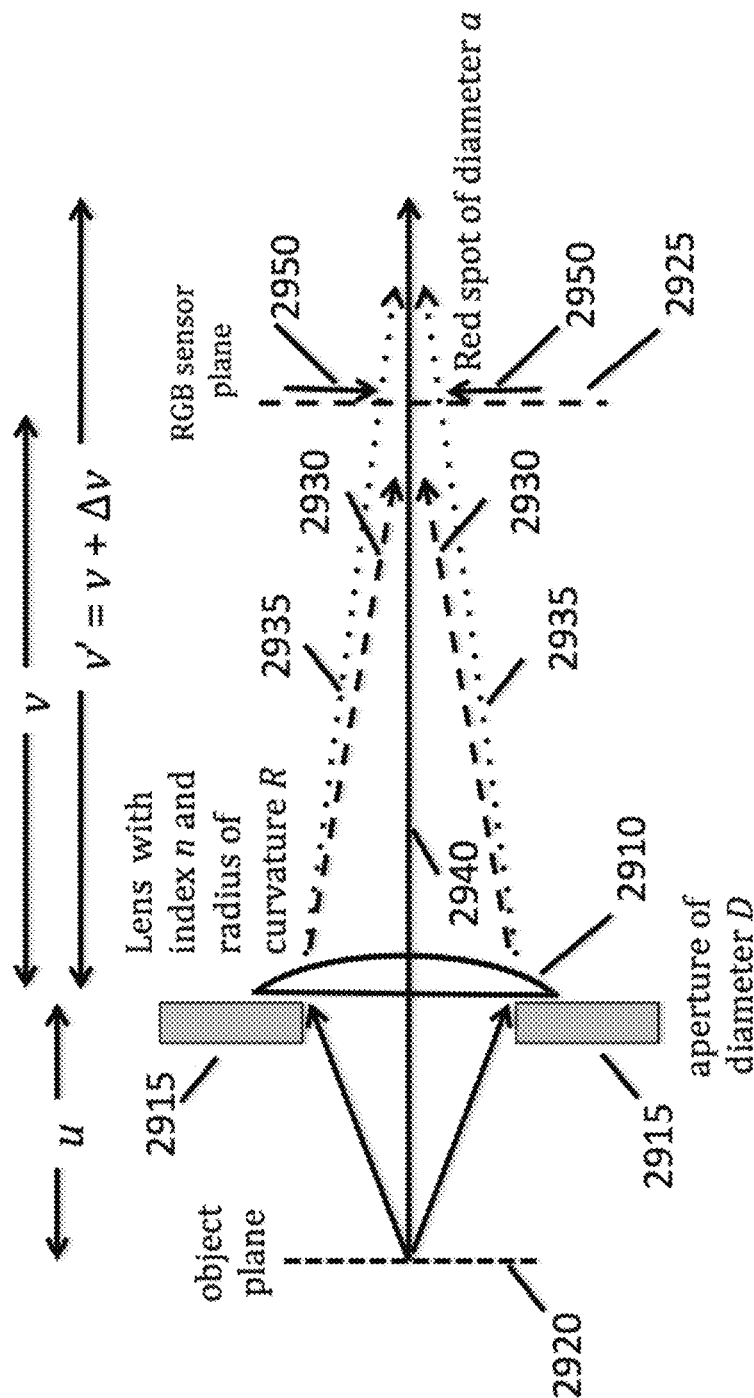
FIG. 29 shows an example of an achromatic lens and its operation.

FIG. 29 shows an example of an achromatic lens and its operation. As shown in the example of FIG. 29, there is an achromatic lens 2910 with an aperture 2915 of diameter D, objects in an object plane 2920, and an RGB sensor plane 2925. The achromatic lens imperfectly brings objects in the object plane to a focus at the RGB sensor plane. In this example, green light 2930 indicated by dashed lines is brought to a sharp focus at RGB sensor plane 2925. Red light 2935 indicated by dotted lines is not. Ray traces common to both colors are indicated by solid lines.

For example, both green and red light follow the path of a central ray 2940. For example, if achromatic lens 2910 is made of a single material with an index of refraction that decreases with increasing wavelengths (as is typical of most transparent materials), and if distances u and v are adjusted to bring green light 2930 to a focus at RGB sensor plane 2925, red light 2935 will not come to a sharp focus and its corresponding image will be blurred by a spot size of diameter "a" as indicated by arrows 2950.

Defying conventional practice with RGB camera systems, in some cases it is sufficient for particle shape analysis to enable a sharp focus image for one color only; useful color analysis may be performed with the aid of other color images, even if they are somewhat blurred.

The requirements for achromatic optics may be further relaxed via particle (e.g., pollen or mold spore) sample illumination by the selected color using a light source with a narrow spectral width. A narrow band of illumination as provided by the quantum dots facilitates generating a very sharp image for a particular color. For example, in a lens having achromatic aberrations where all colors do not come into complete focus, the camera sensor can be focused for a particular color (e.g., wavelength) in order to generate a very sharp image in that particular color. In other words, particles captured within the image will be sharply defined which, in turn, facilitates the morphological analysis.

While for many scientific optical spectrometer applications, light emitted from quantum dots would not be considered as narrow in spectral width, for the purpose of enabling low-cost lens systems with relaxed tolerances on chromatic aberrations, and relative to the native spectral widths of RGB color sensitivities of common digital camera sensors, quantum dots do provide a useful "narrow" spectral width. In another specific embodiment, systems and techniques are provided to enrich the color spectral information captured by RGB color camera sensors with the aid of quantum dots.

System and techniques are provided to reliably identify or discriminate particles based on images of the particles where the images have been created using low-cost RGB camera systems. In an embodiment, an airborne particle monitor includes a low-cost RGB camera system which generates first and second images of particles that have been collected. The images are color-images. In the first image, one color at most is in focus. In the second image the particles have been illuminated using light emitted from quantum dots. A first analysis is performed on the first image to generate a listing of candidate particles. The first analysis is based on geometric features that have been captured in the first image. The geometric features may include size, shape, surface texture, or combinations of these. A second analysis is performed on the second image to narrow the listing of candidate particles. The second analysis is based on color features that have (or have not) been captured in the second image.

In a specific embodiment, a particle or digital optical imaging system includes an image sensor, a lens assembly and an illumination source. Particles may be collected on the surface of a slide and illuminated by a set of light sources from above, below, or both. A lens or lens assembly images, through an iris defining the aperture of the lens assembly, the particles on an image sensor.

In a specific embodiment, the image sensors that can be used have been developed and are mass-produced for digital cameras including digital cameras built into smart phones. These silicon chip devices provide mega-pixel RGB images at relatively low cost. A representative pixel pitch for such sensor chips is 1.4 microns. These powerful and low-cost image sensors can be used for the purpose of enabling low-cost automated particle (e.g., pollen or mold spore) monitoring systems.

Because particles such as pollen grains are typically only tens of microns in diameter, in a specific embodiment, it is generally preferable for the imaging system to provide some magnification between the sampled pollen and its image at the imaging sensor. For example, to provide a factor of four magnification, the distance from the lens assembly to the image sensor for the image sensor may be about four times the distance from the lens assembly to the sampled pollen. As image resolution approaching the wavelength of light is desired, diffraction limited optics with relatively large apertures may be needed. This makes the problem of chromatic aberrations more difficult.

Optics based on low-cost plastic molded parts using only one type of plastic is desirable from a cost perspective. However, such low-cost lens constructions will typically suffer significant chromatic aberration, particularly if large apertures are required. Generally, such low-cost plastic molded lens systems would not be an option for airborne particle (e.g., pollen or mold spore) imaging systems. Applicants have appreciated, however, that in some cases of airborne particle imaging, it is sufficient if only one of the RGB color images is in sharp focus.

In a specific embodiment, the middle color green is desired as being the color with the sharp focus. In other specific embodiments, red or blue may be desired as being the color with the sharp focus. In a specific embodiment, a pollen imaging system includes a molded plastic lenses is optimized for green light at the expense of allowing considerable chromatic aberration for red and blue light.

As discussed, in conventional color optics systems this would be unacceptable, but for the purpose of distinguishing between types of pollen and between pollen and other particulates, applicants have appreciated that in some cases it is sufficient to use a sharp green image to provide shape or geometry information, i.e. morphological information, with which to distinguish between particle types and then use somewhat blurred red and blue images as well to determine color information with which to distinguish between particle types. In other words, applicants have appreciated that for particle (e.g., pollen or mold spore) imaging it can be acceptable in some cases for the optics to provide somewhat blurred red and blue images provided that the green image is sharp.

In some cases, applicants have found that if the optics are designed for sharpest focus for red light rather than green light, then the blue image will suffer further blurring. Similarly optimizing optics for blue rather than green will increase blurring of the red image. These considerations favor the choice of green light for the sharp focus image. Nevertheless, in some circumstances it may be appropriate to design optics to provide a sharp focus for red light or blue light.

For example, if near-infrared as well as visible pollen color information is desired, it may be desirable to minimize or reduce chromatic aberration for red so that the near-infrared images are not too blurred. On the other hand, seeking a sharp focus for blue may be appropriate if quantum dots are not used and a white LED is used with a narrow blue spectral peak. Thus, it should be appreciated that while some embodiments are shown and described in conjunction with providing a sharply focused green image, other embodiments provide for a sharply focused red image or a sharply focused blue image, or other wavelength.

The relatively broad spectral width of light received by green RGB camera sensor pixels may well lead to serious chromatic aberration problems even for the green image.

In a specific embodiment, the sampled pollen is sequentially illuminated by a laser light source and a white light source such as a conventional white LED. The lens assembly is optimized or designed to minimize or reduce aberration for light at the laser's wavelength. A sharp-focused image is captured during sample illumination by the laser. If, for example, the laser is red then red camera sensor pixels are used to capture the sharp image and if the laser is green then green camera sensor pixels are used. Particle (e.g., pollen or mold spore) color information with which to distinguish between particulate types is then collected during sample illumination by a white LED. However, in some applications it is desirable to avoid the expense of a laser light source.

In a specific embodiment, quantum dots are used to provide a low-cost alternative for providing narrow spectral width light sources. For example, quantum dots may be used to provide a narrow spectral width green light source. The combination of allowing blurred red and blue images plus the use of quantum dots to provide a narrow-spectral-width green-light illumination source enable the use of low-cost single-plastic lenses in a particle (e.g., pollen or mold spore) imaging system.

Table D below shows an illumination sequence for sharp image and color measurement. Table D below considers a specific scenario in which a particle imaging system collects a sharply focused image at one color as well as capturing particle color information at other colors. In this scenario there are two light sources that are alternately illuminating the sampled particle. A first light source in an illumination sequence includes quantum dots and produces green light with a narrow spectrum. While this quantum-dot green light source is activated the green pixels of the RGB camera sensor captures a sharply focused image of the pollen grains for shape analysis. Green can be desirable because it's wavelengths are between blue and red. After this quantum-dot green light source is turned off, a white light source is activated enabling broad-spectrum red, green and blue images to be simultaneously captured by the RGB camera sensor for pollen color analysis.

It should be appreciated that the sequence of illumination may be swapped. For example, the illumination sequence may include activing the white light, capturing a first image of the particles under the white light, de-activating the white light, activating the green light, and capturing a second image of the particles under the green light.

TABLE D

| Illumination sequence | Illumination source | RGB pixels used | Color imaged |
|---|---|---|---|
| 1 | Quantum-dot green | GREEN | Narrow-spectrum green |
| 2 | White | RED | red |
| 2 | White | GREEN | green |
| 2 | White | BLUE | blue |

An alternate to the scenario of table D is to have only one light source including green quantum dots resulting in generation of a strong narrow spectral peak of green light superposed on broad spectrum of white light. In this case, the RGB camera sensor green image will capture a superposition of a sharp quantum-dot-green image and a less strongly focused green image; in some cases this will be acceptable if not ideal for particle (e.g., pollen or mold spore) shape recognition.

In a further refinement of this alternate scenario, the white light source also contains red and blue quantum dots as well as green quantum dots so that the light output of the light source is concentrated in three narrow spectral peaks; this will reduce the contamination of the green RGB camera sensor image from light that is not from the green quantum dots.

In a specific embodiment, a particle imaging system incorporates quantum dots into the light sources. In one approach, a film containing quantum dots is placed between the particle (e.g., pollen or mold spore) sample and a light source such as an LED, thus sharpening the spectral peaks relative to the original light source. In another approach, the quantum dots are electrically excited to directly create light with desired spectral properties; for example, quantum dots may be the light emitting elements within an LED.

Figure 30:
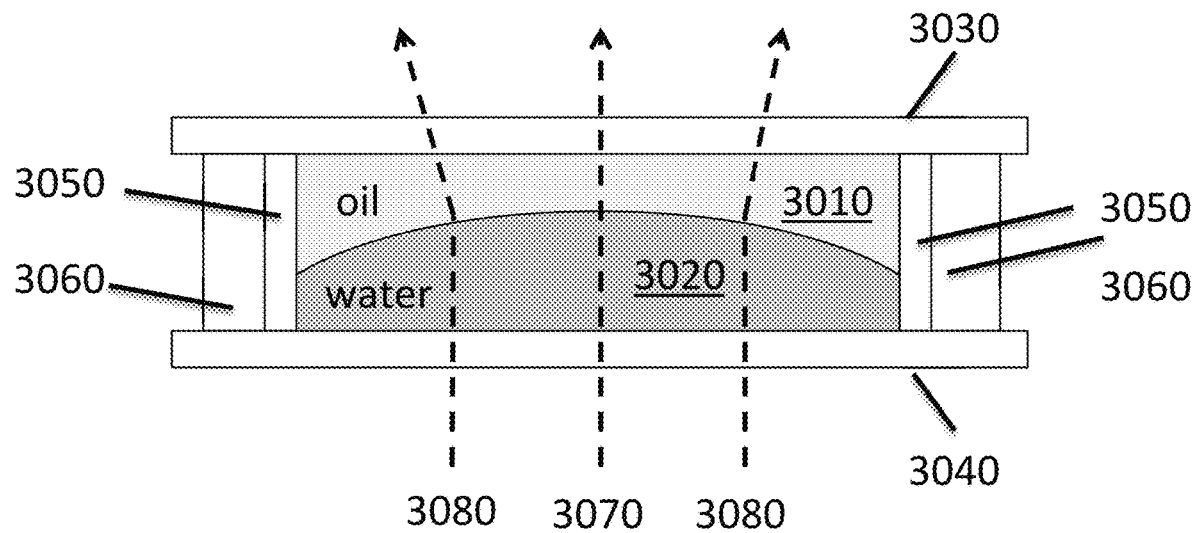
FIG. 30 shows a "liquid lens" in a first state that may be included in a particle monitor in another specific embodiment.
Figure 31:
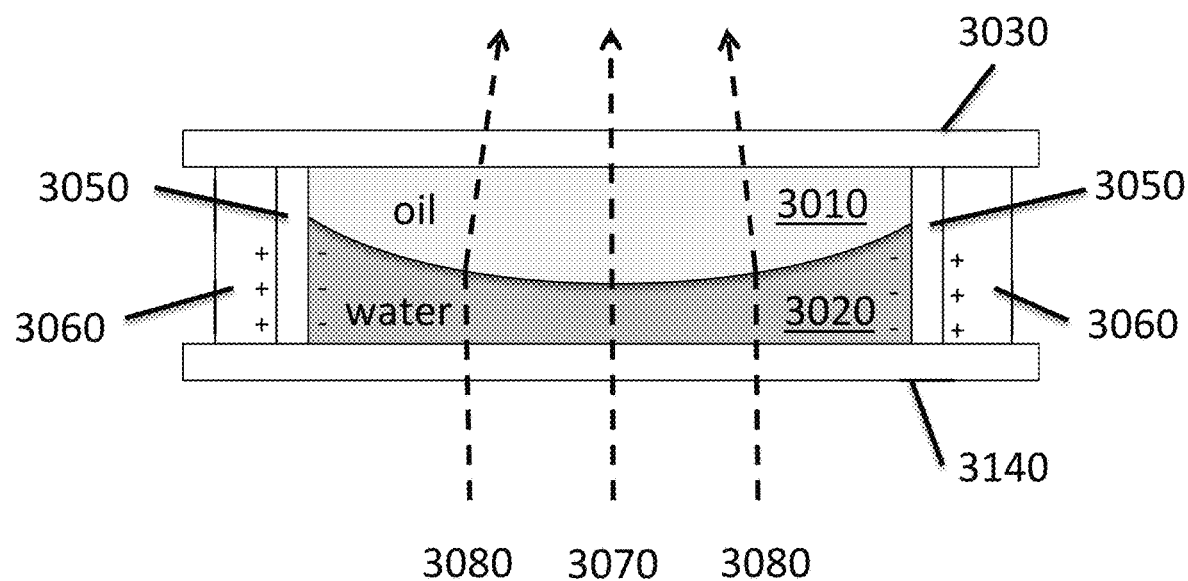
FIG. 31 shows the "liquid lens" from FIG. 30 in a second state.

In some cases, it may be desirable to include an auto-focus mechanism, or more generally an adjustable focus mechanism under software control, within particle monitoring system 105. A suitable auto-focus mechanism is a "liquid lens" as available from Varioptics of Lyon, France. FIG. 30 shows a sealed cell in an off-state. FIG. 31 shows the sealed cell in an on-state. Referring now to FIG. 30, the sealed cell includes oil 3010, water 3020, an upper transparent window 3030, a lower transparent window 3040, and electrodes 3060.

The oil is of a high refractive index and is trapped, along with the water, between the upper and lower transparent windows. There is a thin water repellent surface 3050 between the oil and water and the effects of surface tension, result in the oil/water boundary taking a shape such that the oil is shaped into a diverging lens when electrode 3060 is uncharged.

The result is that if a parallel one axis light ray 3070 and off-axis light rays 3080 enter the device, the off axis light rays 3080 will diverge from the on-axis ray 3070 upon exiting the device.

Referring now to FIG. 31, if electrode 3060 is charged, it will attract the water 3020 due to water's high dielectric constant reshaping the oil 3010 into a converging lens as illustrated by the on-axis ray 3070 and off-axis rays 3080. The device is cylindrically symmetric about the on-axis ray 3070. As one of skill in the art would recognize, the diagrams shown in FIGS. 30 and 31 are schematic for conceptual clarity and the geometry of the electrodes can be more complex.

Addition of an auto-focusing mechanism adds to the complexity of providing achromatic optics, hence the methods presented above for relaxing the tolerances for chromatic aberrations become more beneficial if the system includes an auto-focus or adjustable focus mechanism such as a liquid lens.

Having addressed the issue of providing at least one sharp color image for measuring shape features of pollen and other particulates, let us now turn our attention to techniques or means to enhance the color information available to distinguish between types of pollen and other particles.

With particle samples illuminated with a white light source, an RGB camera sensor provides three images. In principle, one could redesign the camera sensor with additional types of color pixels to become, for example, an RYGBV (red, yellow, green, blue, violet) camera sensor, but without the mass market of color digital cameras behind it, this would be a very expensive solution for particle imaging systems.

Consider, as an example, examining the yellow component of a pollen image with an RGB camera sensor. If a pollen sample is illuminated with a pure yellow light source, an image of the yellow color component of a pollen grain will be captured by both the green and red pixels of the RGB camera sensor. Quantum dots can provide at low cost such a source of pure yellow, and other pure colors. With a set of N sequentially activated quantum-dot enhanced light sources, pollen grains may be imaged at N different colors.

Note that N may be larger the 3 (the number of colors nominally supported by an RGB camera sensor). For example, Table E below shows an illumination sequence for N=9 colors to provide an example with 9 colors.

TABLE E

| Illumination sequence | Illumination source | RGB pixels used | Color imaged |
|---|---|---|---|
| 1 | Red | RED | Red |
| 2 | Red-orange | RED | Red-orange |
| 3 | Orange | RED | Orange |
| 4 | Yellow-green | GREEN | Yellow-green |
| 5 | Green | GREEN | Green |
| 6 | Blue-green | GREEN | Blue-green |
| 7 | Blue | BLUE | Blue |
| 8 | Blue-violet | BLUE | Blue-violet |
| 9 | Violet | BLUE | Violet |

In a specific embodiment, the quantum dots are spherical in shape. In another specific embodiment, the quantum dots are non-spherical in shape. In particular, quantum dots may have an elongated shape. Quantum dots of an elongated shape are often referred to as "quantum rods." Elongated quantum dot shapes may be used to improve quantum dot light generating efficiency. Furthermore, while spherical quantum dots emit unpolarized light, elongated quantum dots may be used to emit linearly polarized light.

As an example, the nine step illumination sequence of table E may be expanded to an eighteen step illumination sequence corresponding to eighteen quantum dot illumination sources where each illumination color of table E corresponds to two illumination sources of differing linear polarization orientations. Optionally, polarizers may be placed in the optical paths to a camera sensor or other type of optical sensor. A pollen monitor with polarized quantum dot (quantum rod) illumination sources may provide enhanced allergenic particle detection and discrimination via measurements of the interaction of detected particulates with polarized light. A pollen monitor may include a combination of quantum dots having a spherical shape and quantum dots having an elongated shape.

While the cleanest separation of pollen image color components is provided when each quantum-dot color source is activated one at a time, in some cases it may be advantageous to more rapidly scan the set of N illumination colors. This is possible by taking advantage of the factor that RGB cameras sensors are designed to capture three colors simultaneously.

For example, consider the scenario given in table F below. A first LED light source contains three sets of quantum dots, one set emitting at a red wavelength, another set emitting at a yellow-green wavelength and a third set emitting at a blue wavelength. When this first LED light source is activated the red pixels of the RGB camera sensor will respond most strongly to the red wavelength, the green pixels to the yellow-green wavelength and the blue pixels to the blue wavelength.

Hence images may be simultaneously captured for the three color-components of this first LED as indicated by a common illumination sequence number "1" for red, yellow-green and blue in table F. A second LED light source contains another three sets of quantum dots that emit wavelengths corresponding to the colors of red-orange, green and blue-violet. When this second LED is activated, the RGB camera sensor simultaneous captures images corresponding to the second set of quantum dot colors. Similarly for a third LED contains three sets of quantum dots corresponding the colors orange, blue-green and violet. Hence with only three LEDs that are sequentially activated, images for nine different spectral components of pollen color may be captured. Many other options exist for combining more than one quantum-dot color in one illumination step.

TABLE F

| Illumination sequence | Illumination source | RGB pixels used | Color imaged |
|---|---|---|---|
| 1 | LED #1 (red/yellow-green/blue) | RED | Red |
| 1 | LED #1 (red/yellow-green/blue) | GREEN | Yellow-green |
| 1 | LED #1 (red/yellow-green/blue) | BLUE | Blue |
| 2 | LED #2 (red-orange/green/blue-violet) | RED | Red-orange |
| 2 | LED #2 (red-orange/green/blue-violet) | GREEN | Green |
| 2 | LED #2 (red-orange/green/blue-violet) | BLUE | Blue-violet |
| 3 | LED #3 (orange/blue-green/violet) | RED | Orange |
| 3 | LED #3 (orange/blue-green/violet) | GREEN | Blue-green |
| 3 | LED #3 (orange/blue-green/violet) | BLUE | Violet |

Let us consider in more detail the effects of color crosstalk for the illumination sequence given in table F. Color crosstalk may be mathematically expressed with the following matrix equations. The column vectors to the left represent the RBG camera sensor response for the three types of pixels. For example $GREEN_2$ represents the signal amplitude response of green pixels when the pollen sample is illuminated with LED #2 of table F. To the far right are column vectors representing the strengths of the quantum-dot illumination sources within an LED of table F. To the immediate right of the equal signs are weighting matrices corresponding to each of the three LEDs. For example, $W_2(BLUE, \text{red orange})$ gives the strength of response of blue camera pixels to the color of light from the red-orange quantum dots. These equations express that fact that due to color crosstalk, red, green and blue camera images correspond to weighted mixtures of the quantum-dot colors.

$$\begin{bmatrix} RED_1 \\ GREEN_1 \\ BLUE_1 \end{bmatrix} = \begin{bmatrix} W_1(RED, red) & W_1(RED, \text{yellow green}) & W_1(RED, blue) \\ W_1(GREEN, red) & W_1(GREEN, \text{yellow green}) & W_1(GREEN, blue) \\ W_1(BLUE, red) & W_1(BLUE, \text{yellow green}) & W_1(BLUE, blue) \end{bmatrix} \times \begin{bmatrix} red \\ \text{yellow green} \\ blue \end{bmatrix}$$

$$\begin{bmatrix} RED_2 \\ GREEN_2 \\ BLUE_2 \end{bmatrix} = \begin{bmatrix} W_2(RED, \text{red orange}) & W_2(RED, green) & W_2(RED, \text{blue violet}) \\ W_2(GREEN, \text{red orange}) & W_2(GREEN, green) & W_2(GREEN, \text{blue violet}) \\ W_2(BLUE, \text{red orange}) & W_2(BLUE, green) & W_2(BLUE, \text{blue violet}) \end{bmatrix} \times \begin{bmatrix} \text{red orange} \\ green \\ \text{blue violet} \end{bmatrix}$$

$$\begin{bmatrix} RED_3 \\ GREEN_3 \\ BLUE_3 \end{bmatrix} = \begin{bmatrix} W_3(RED, orange) & W_3(RED, \text{blue green}) & W_3(RED, violet) \\ W_3(GREEN, orange) & W_3(GREEN, \text{blue green}) & W_3(GREEN, violet) \\ W_3(BLUE, orange) & W_3(BLUE, \text{blue green}) & W_3(BLUE, violet) \end{bmatrix} \times \begin{bmatrix} orange \\ \text{blue green} \\ violet \end{bmatrix}$$

The quantum-dot color components of the RGB camera images may be computed by solving the above equations. This is can be done by first multiplying the above questions by the inverses of the weighting matrices, and then applying the resulting matrix equations below. If an illumination source contains less than three color sources, the three RGB camera images will provide redundant information with which to separate the image contributions from each color source. If an illumination source contains more than three quantum-dot colors, we mathematically have only three questions to determine more than three unknowns and hence the three RGB camera color images are insufficient to fully separate out the contributions of the more than three quantum-dot colors; nevertheless there may be cases in which the use of more than three quantum-dot colors within a single LED may contribute to useful enrichment of pollen color for the purpose of distinguishing between types of pollen (or other particles).

$$\begin{bmatrix} red \\ \text{yellow green} \\ blue \end{bmatrix} = (W_1)^{-1} \times \begin{bmatrix} RED_1 \\ GREEN_1 \\ BLUE_1 \end{bmatrix}$$

$$\begin{bmatrix} \text{orange red} \\ green \\ \text{blue violet} \end{bmatrix} = (W_2)^{-1} \times \begin{bmatrix} RED_2 \\ GREEN_2 \\ BLUE_2 \end{bmatrix}$$

$$\begin{bmatrix} orange \\ \text{blue green} \\ violet \end{bmatrix} = (W_3)^{-1} \times \begin{bmatrix} RED_3 \\ GREEN_3 \\ BLUE_3 \end{bmatrix}$$

LED #1 of table F, for example, may contain three types of quantum dots as locations for electron-hole recombination resulting in emission of red, yellow-green and blue photons. Alternatively the LED might be a conventional white, blue or ultraviolet LED whose light passes through a film containing red, yellow-green and blue quantum dots before reaching the sampled pollen.

As yet another alternative for generating the nine color images of table F, light from one and only one conventional white, blue or ultraviolet LED may be intercepted by a disk that may be rotated so as to sequentially place a red/yellow-green/blue quantum-dot film, a red-orange/green/blue-violet quantum-dot film and an orange/blue-green/violet quantum-dot film in the light path from the LED to the sampled particles (e.g., pollen or mold spores).

Figure 32A:
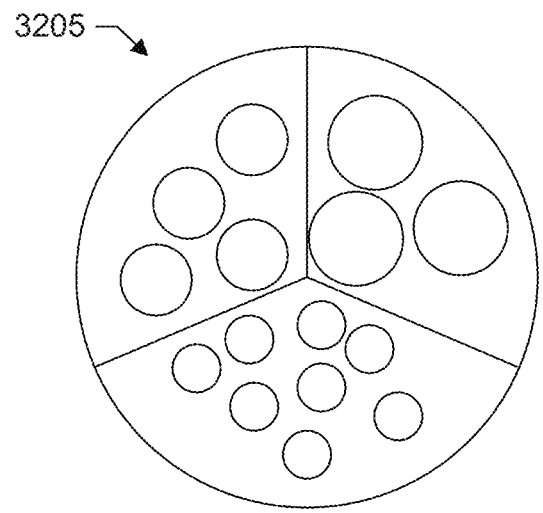
FIG. 32A shows a top view of a disk having various separate regions of differently sized quantum dots.

FIG. 32A shows an example of a disk having regions of differently sized quantum dots that may be included in one embodiment of particle monitor 105. FIG. 32A shows a plan view of a disk 3205 having a set of regions or sections 3215A-C. A first region 3215A includes a first set of quantum dots 3220A of a first size (e.g., diameter) dispersed within. A second region 3215B includes a second set of quantum dots 3220B of a second size dispersed within. A third region 3215C includes a third set of quantum dots 3220C of a third size dispersed within. There can be a spindle connected to a center 3225 of the disk. The spindle rotates or turns the disk so that a particular region can face the light emitting element in order to convert the light emitted from the light emitting element into the particular colored light desired for illuminating the collected particles.

The first size is different from the second, and third size. The second size is different from the third size. In the example shown in FIG. 32A, the size of the first set of quantum dots is greater than the size of the second and third sets of quantum dots. The size of the second set of quantum dots is less than the size of the first and third sets of quantum dots. The size of the third set of quantum dots is less than a size of the first set of quantum dots and greater than the size of the second set of quantum dots.

To make or manufacture the disk, the different regions may be produced as separate individual sub-units and then joined together as a single unit. The joining may include, for example, gluing each of the first, second, and third individual regions together.

The disk shown in the example of FIG. 32A has been partitioned into three regions of differently sized quantum dots. It should be appreciated, however, that the disk may be partitioned into any number of regions of differently sized quantum dots (e.g., two, three, four, five, six, seven, or more than seven regions) Increasing the number of regions of differently sized quantum dots helps to increase the accuracy of particle identifications, but can also increase the overall size of the disk and, in turn, the overall form factor of the particle monitor. Factors to consider in determining the number of regions of differently sized quantum dots for a disk include the desired form factor of the particle monitor, the desired accuracy or sensitivity of the particle monitor in identifying or discriminating particles, the variety of particle types desired to be identified, and other factors.

In an embodiment, particle monitor 105 includes a motor, disk, and light emitting element. The disk is divided into a set of regions. A region can include a set of quantum dots where a size (e.g., diameter) of the quantum dots dispersed one region is different from a size of quantum dots dispersed in another region. The disk is connected to the motor and is positioned to receive light from the light emitting element. The motor rotates (or moves) the disk while the light emitting element remains stationary or fixed. The disk may be rotated by the motor into a first position such that a first region of the disk having a first set of quantum dots of a first size faces the light emitting element. When light from the light emitting element hits or is received by a first side of the disk facing the light emitting element, the light is converted by the first set of quantum dots and emitted out a second side of the disk, opposite the first side of the disk, as first converted light.

The disk may be rotated by the motor into a second position such that a second region of the disk having a second set of quantum does of a second size, different from the first size, faces the light emitting element. When the light from the light emitting element is received by the first side of the disk facing the light emitting element, the light is converted by the second set of quantum dots and emitted out the second side of the disk as second converted light, different from the first converted light. For example, a wavelength of the first converted light may be different from a wavelength of the second converted light. A wavelength of the first converted light may be greater than a wavelength of the second converted light. A wavelength of the first converted light may be less than a wavelength of the second converted light.

A method for particle identification may include rotating the disk to the first position, capturing a first image of collected particles when the collected particles are illuminated by the first converted light, analyzing the first image to identify one or more particles, determining that features captured in the first image are insufficient to identify the particles, in response to the determination, rotating the disk to the second position, capturing a second image of the collected particles when the collected particles are illuminated by the second converted light, and analyzing the second image to identify the one or more particles. The features may include colors or color information that has been captured (or not captured) by the images.

In another specific embodiment, a light emitting element rotates (or moves) and a disk having regions of quantum dots of different sizes remains stationary. In this specific embodiment, particle monitor 105 includes a motor, disk, and light emitting element. The disk is divided into a set of regions, each region having a set of quantum dots of a size different from quantum dots of another region. The light emitting element is connected to the motor and is positioned to shine light towards the disk. The light emitting element may be rotated by the motor into a first position. In the first position, light from the light emitting element is received by a first region having a first set of quantum dots of a first size dispersed within. The first set of quantum dots convert the light and emit first converted light. The light emitting element may be rotated into a second position, different from the first position. In the second position, light from the light emitting element is received by a second region having a second set of quantum dots of a second size, different from the first size, dispersed within. The second set of quantum dots convert the light and emit second converted light, different from the first converted light. In another specific embodiment, the motor may be omitted and the disk, light emitting element, or both may be rotated or moved manually such as by a user.

It should be appreciated that the disk having regions of different quantum dot sizes may instead be replaced by a film having regions of different quantum dot sizes. The film can be of any shape and not necessarily disk- or circular-shaped. For example, the film can be shaped as a rectangle, square, triangle, or any other shape as appropriate. In an embodiment, both the disk (or film) having regions of different quantum dot sizes and the light emitting element may move. The movement may be a rotation, translation, or both.

In another specific embodiment, particle monitor 105 includes removable quantum dot containing films. For example, there can be first and second films. The first film includes a first set of quantum dots having a first size. The second film includes a second set of quantum dots having a second size, different from the first size. The user can swap between the first and second films in order to illuminate the particles under different lighting using the same light emitting element. That is, the user can remove the first film from the particle monitor and insert the second film into the particle monitor (and vice-versa).

For example, the particle monitor may capture a first image of the collected particles when the particles are illuminated by light emitted from the first film. If the particle monitor determines that the particles cannot be identified based on features captured in the first image, the particle monitor may prompt the user to remove the first film and insert the second film. For example, the particle monitor may display the message, "Particle identification not successful. Please replace quantum-dot containing film A with quantum-dot containing film B." Once the user has replaced the first film with the second film, the particle monitor may capture a second image of the collected particles when the particles are illuminated by light emitted from the second film.

In an embodiment, removable films containing quantum dots may be removed and replaced by the user without use of tools. For example, a removable film containing quantum dots may be snap-fitted into place within the particle monitor, or may slide along a track within the particle monitor. In another embodiment, a removable film containing quantum dots may be attached within the particle monitor using fasteners such as screws, bolts, and nuts. In this embodiment, tools (e.g., screw driver) may be used by the user to swap-in different films. For example, the particle monitor housing may be designed to be removable so that the user can access internal components of the monitor (e.g., access a removable film having quantum dots).

Figure 32B:
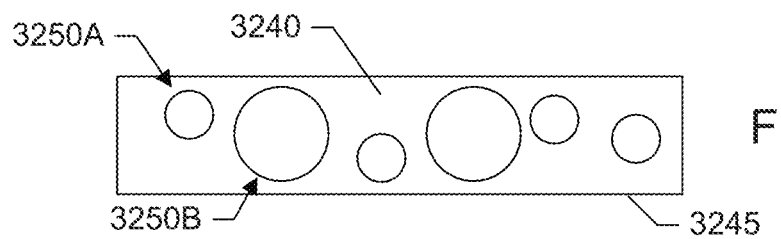
FIG. 32B shows a cross section of a film having a mixture of differently sized quantum dots.

FIG. 32B shows a cross section of a film 3240 having two sets of quantum dots of different sizes. In the example shown in FIG. 32B, there is a matrix material (e.g., a clear polymer) 3245 in which first and second sets of quantum dots 3250A-B have been dispersed or mixed in. The first set includes quantum dots having a first size (e.g., first diameter). The second set includes quantum dots having a second size (e.g., second diameter), different from the first diameter. For example, the first size may be greater or less than the second size. A quantum dot film such as shown in FIG. 32B can be used to emit two different colors (e.g., green and red) simultaneously. In other words, there can be a single film having both large and small quantum dots. A single film may contain any number of sets of quantum dots where quantum dots in one set are of a different size (e.g., diameter) than quantum dots in another set.

Figure 32C:
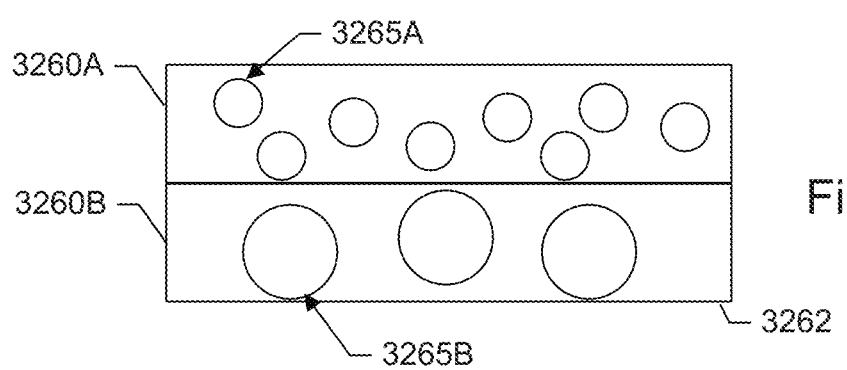
FIG. 32C shows a cross section of a stack of films, each film having a set of quantum dots of a size that differ in size from another film of the stack.

FIG. 32C shows a cross section of two films 3260A-B that have been stacked together to form a stack 3262. The quantum dots shown in FIG. 32C are similar to the quantum dots shown in FIG. 32B. In the example shown in FIG. 32C, however, the different sets of quantum dots have been placed in separate films. In particular, first film 3260A includes quantum dots 3265A having a first size (e.g., first diameter). Second film 3260B includes quantum dots 3265B having a second size (e.g., second diameter), different from the first size. A stack of quantum dot films as shown in the example of FIG. 32C may likewise be used to emit two different colors simultaneously. A stack may include any number of quantum dot films. A stack may include two or more films. A film in the stack may include at most one set of quantum dots of a particular size. A film in the stack may include two or more sets of quantum dots, each set having a quantum dot size that is different from a quantum dot size in another set.

Since, for example, the green subpixels in the camera sensor are the ones that respond most strongly to green light, and the red subpixels in the camera sensor are the ones that respond most strongly to red light, the green and red lights may be illuminated sequentially (e.g., one at a time) or simultaneously. Cross-talk may be compensated through mathematical equations.

Auto-focus mechanisms (such as shown in FIGS. 30-31) may be used not only to assure the best focus possible for the color selected for the most sharply focused image, but also to improve the focus for other color images. The out-of-focus problem for the non-optimized colors can be addressed by applying the auto-focus function at these non-optimized colors.

For example, for the illumination sequence given in tables E and F, an auto-focusing mechanism may be used to improve the resolution of each of the nine color images captured; in this case the narrow spectral width of each of the quantum dot light sources enhance the sharpness of each auto-focused color image.

For the illumination sequence given in table F, where each illumination source contains multiple quantum-dot colors, auto-focusing may be used, for example, to optimize the sharpness of the green RGB sensor pixel images individually for each of the yellow-green, green and blue-green illumination source components. Again referring to the illumination sequence given in table F, during illumination by LED #1, the red RGB sensor pixel image may be captured after auto-focusing the red pixel image and similarly for the green and blue RGB pixel images, and then auto-focusing three times again during the illumination by LED #2 and three more time for LED #3. The narrow spectral width of quantum-dot light sources enhances the benefits of scenarios in which auto-focusing mechanism is used for more than one color image.

In some cases of pollen imaging system design, it is desirable to collect enriched pollen color information for use in distinguishing between types of pollen and of secondary importance to minimize or reduce the cost of the lenses. In such cases it may be appropriate to accept the expense of achromatic lens systems in order to obtain the benefit of sharp pollen images at all wavelengths of light.

A discussion of chromatic aberration from a more quantitative perspective is provided below. Referring back to FIG. 29 a schematic of an optical system is shown. As discussed, there is a "pollen" object plane 2920 and an "RGB sensor" image plane 2925 with a thin lens 2910 with an aperture 2915 of diameter D in between. Furthermore, let the thin lens have one flat surface and one surface with a radius of curvature R. Let u be the distance from the pollen object plane to the lens and v be the distance from the lens to the RGB sensor image plane.

If the thin lens has a focal length f, then the following focal length equation applies.

$$\frac{1}{f} = \frac{1}{u} + \frac{1}{v}$$

If we let M be the magnification, e.g., the ratio of the size of a pollen image at the RGB sensor to the actual size of the pollen grain at the object plane, then M is related to u and v as follows.

$$M = \frac{v}{u}$$

Eliminating u in the above two equations gives us the following equation.

$$\frac{v}{f} = (1 + M)$$

The Lens Maker's Equation for focal length of a lens as a function of its shape and index of refraction is as follows where d is the thickness of the lens and $R_1$ and $R_2$ are the radii of curvature of the lens surfaces.

$$\frac{1}{f} = (n-1)\left[\frac{1}{R_1} - \frac{1}{R_2} + \frac{(n-1)d}{nR_1R_2}\right]$$

In the thin lens approximation where $d \ll R_1$ and $d \ll R_2$, the last term in the square brackets can be neglected so that we have the following equation. Note that the focal length is inversely proportional to (n−1).

$$\frac{1}{f} = (n-1)\left[\frac{1}{R_1} - \frac{1}{R_2}\right]$$

For the above sketch where one radius of curvature is infinite and the other radius of curvature is R, this reduces to the following.

$$\frac{1}{f} = \frac{(n-1)}{R}$$

Combined with the first equation above, we have the following.

$$\frac{(n-1)}{R} = \frac{1}{u} + \frac{1}{v}$$

As suggested in the above sketch, let us assume that things have been arranged so that a green wavelength of light from the pollen object plane is sharply focused on the RGB sensor image plane. The index of refraction n in the above equations corresponds to this selected green wavelength. Now also consider a red wavelength with a different index of refraction $n' = n + \Delta n$ which would come to a focus at a distance $v' = v + \Delta v$ from the lens (if the RGB sensor was not in the way). Assuming the pollen object plane to lens distance u to be fixed, differentiating the above equation gives the following.

$$\frac{\Delta n}{R} = -\frac{\Delta v}{v^2}$$

This in turn implies the following.

$$-\frac{\Delta v}{v} = v\frac{\Delta n}{R} = \frac{v}{f}\frac{\Delta n}{(n-1)} = (1+M)\frac{\Delta n}{(n-1)}$$

At the RGB sensor image plane, the red light forms a spot of diameter "a" which by similar triangles is related to the aperture D by the ratio of $\Delta v$ to v'. Approximating v' by v, we have the following relation.

$$\frac{a}{D} = \frac{\Delta v}{v'} \approx \frac{\Delta v}{v}$$

This red spot diameter "a" at the image plane is a measure of chromatic aberration. Demagnifying by a factor 1/M so as to refer to more usefully to dimensions in the pollen object plane, it corresponds to a blurring diameter of a/M.

The blurring diameter a/M represents the extreme disagreement possible between to rays contributing to the red spot. On average the effects of chromatic aberration will be less. A more appropriate measure of blurriness due to chromatic aberration may be obtained by including an appropriate constant factor less than one. Estimating the blurring effect of chromatic aberration may be as follows.

$$\text{Chromatic aberration} = (\text{constant})\frac{a}{M} \approx (\text{constant})\frac{D}{M}\frac{\Delta v}{v}$$

$$\text{Chromatic aberration} \approx (\text{constant})\, D + \frac{(1+M)}{M}\frac{\Delta n}{(n-1)}$$

This blurring of particle (e.g., pollen grain) images due to chromatic aberration in the lens may be one of several factors that blur the image. Depending on whether the above chromatic aberration is large or small compared to other sources of image blurring determines whether chromatic aberration may be considered significant or negligible.

For example, if the optics in FIG. 29 is designed to produce a sharp image for a selected green wavelength, then the corresponding image for an alternative wavelength, such as red in the above sketch, may be considered to suffer from significant chromatic aberration if the alternative wavelength image is blurred by a factor of two or more compared to the wavelength selected for the sharpest image. It should be appreciated that such a definition of significant chromatic aberration is not limited to the thin lens optics shown in FIG. 29.

Another approach to defining significant chromatic aberration may include the aid of the diffraction limit to optical system resolution. Even in the absence of chromatic aberration, basic principles of wave mechanics limit resolution of microscope systems as follows where λ is the wavelength of the light.

$$(\text{diffraction limit}) = (\text{constant}')\frac{\lambda u}{D} = (\text{constant}')\frac{(1+M)}{M}f\frac{\lambda}{D}$$

If the constant is set to a value of one-half, then the above expression approximates the Abbe diffraction limit.

The ratio of the above expressions for chromatic aberration and diffraction limit is as follows.

$$\text{Ratio} = \frac{\text{(constant)}}{\text{(constant')}} \frac{D^2}{f\lambda} \frac{\Delta n}{(n-1)}$$

If this ratio is much less than one, it may be said that chromatic aberration is negligible. On the other hand, if this ratio is two or larger, then chromatic aberration would significantly interfere with any attempt to optimize optics so as to reach the diffraction limit. While the above ratio was derived from a simple thin lens system, modern optics simulation tools would allow one skilled in the art to estimate the above ratio in more complex systems.

Below let us assume that ratio of the constants above is one-half. Straight-forward simulations with a simulation tool such as Zemax may lead to a more precise value.

For a focal length of 20 mm, and aperture diameter of 5 mm and a wavelength of ~500 nm, the above ratio becomes the following.

$$\text{Ratio} \approx 1250 \frac{\Delta n}{(n-1)}$$

Table G below snows data for an 480R lens as provided by Zeon Corporation of Tokyo, Japan. Such a lens may be used in some embodiments of particle monitor 105.

TABLE G

| Temp (deg C.) | Wavelength (nm) | | | | | | Abbe number Vd |
|---|---|---|---|---|---|---|---|
| | 435.835 (g) | 486.133 (F) | 546.075 (e) | 587.562 (d) | 656.273 (C) | 785.1 (L.D780) | |
| 0 | 1.5396 | 1.5343 | 1.5300 | 1.5277 | 1.5250 | | 56 |
| 25 | 1.5369 | 1.5317 | 1.5273 | 1.5251 | 1.5224 | | 56 |
| 40 | 1.5352 | 1.5299 | 1.5257 | 1.5234 | 1.5207 | 1.5174 | 57 |
| 60 | 1.5329 | 1.5276 | 1.5234 | 1.5211 | 1.5184 | 1.5152 | 57 |
| 80 | 1.5308 | 1.5253 | 1.5214 | 1.5189 | 1.5164 | 1.5132 | 58 |

The wavelengths in the columns correspond to the following colors: violet, blue, green, yellow, orange, infrared. If we compare green at 546.075 and blue at 486.133 at 25° C., the difference in index of refraction is $\Delta n=1.5317-1.5273=0.0044$. The index of refraction for green minus one is 0.5273 so $\Delta n/(n-1)=0.0044/0.5273=0.008344$. Multiplying this by 1,250 gives a ratio of 10, i.e. serious chromatic aberration.

This example is for a difference in wavelength of $(546.075-486.133)=60$ nm. If instead we had a wavelength difference of 15 nm (half of a quantum dot spectral width of 30 nm), the chromatic aberration would be reduced by a factor of 4, for a ratio of 2.5. Still serious chromatic aberration, but significantly improved.

Figure 33:
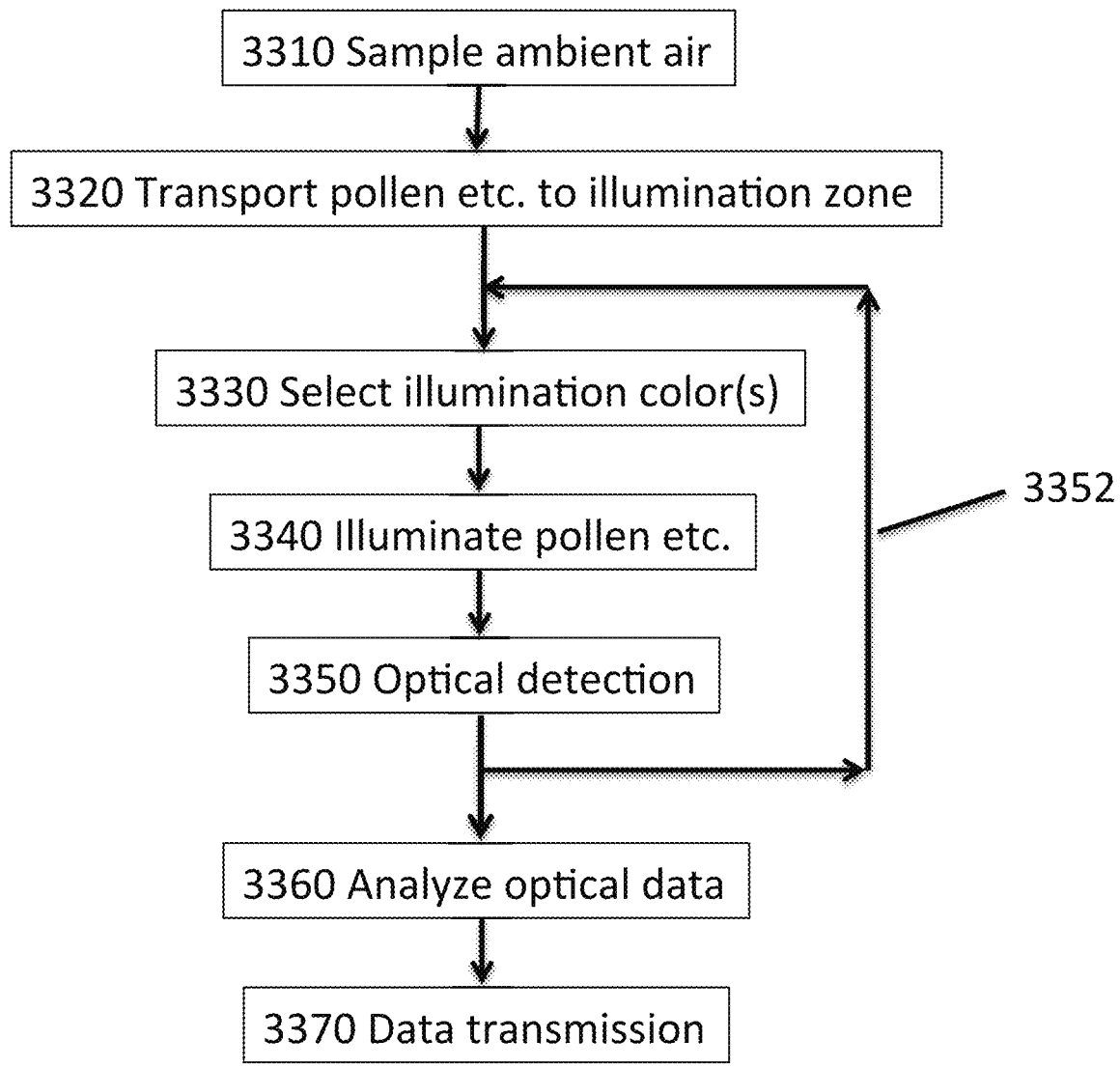
FIG. 33 shows an overall flow illustrating some basic ingredients of automated particle (e.g., pollen) monitoring according to a specific embodiment.

FIG. 33 shows a flow illustrating some basic ingredients of automated particle (e.g., pollen) monitoring according to a specific embodiment. This flow chart illustrates a method of pollen detection. In brief, in a step 3310, a pollen monitor samples ambient air such as via a blower that sucks in the ambient air. In a step 3320, pollen captured from the ambient air is transported to an illumination zone. For example, there can be a supply reel and a take-up reel to transport a sticky tape with adhesive side up past the air-inlet/blower. Pollen and other particles that stick to the adhesive are transported to the illumination zone which is provided by one or more illumination sources, some or all of which may incorporate quantum dots.

In a step 3330, one or more illumination colors are selected. In a step 3340, the pollen is illuminated. The selection of the illumination colors may be based on a pre-determined illumination sequence that is stored by the monitor. The particle (e.g., pollen) monitor access the pre-determined illumination sequence in order to identify the color (e.g., wavelength) of light that should be emitted. The selection can be controlled by a computer. The computer selects an illumination source(s) with desired spectral properties. This may in effect select a particular set or sets of quantum dots and corresponding wavelengths. The selected illumination sources are then activated.

In an embodiment, the illumination sequence may be determined dynamically. A method may include illuminating the captured particles under white light, while the particles are being illuminated by the white light, capturing a first image of the particles, identifying, from the first image, colors of the particles, based on the colors of the particles as revealed by the first image, and selecting another color, different from white, with which to illuminate the particles for a second image of the particles. For example, RGB images collected under white light illumination may contain yellow particles of a shape possibly indicative of grass pollen grains. As discussed previously, the interpretation of the imaged pollen grains being grass pollen may then be tested by using quantum-dot illumination sources corresponding to spectral curves 2832, 2834 and 2836 of FIG. 28.

In a step 3350, the monitor performs an optical detection. The optical detection may include capturing an image of the particles under the illumination. In other words, while the sampled pollen is illuminated, a lens array and an RGB camera sensor capture images of the sampled pollen.

Steps 3330-3350 may be repeated 3352 any number of times in order to capture further color information about the sampled particles (e.g., pollen) and other detected particulates. In a step 3360, the optical data (e.g., images of particles) is analyzed. In a step 3370, the optical data (e.g., images) may be transmitted to a remote server.

In an embodiment, as discussed above, the particle monitor can be connected to a network. The connection to a network allows the particle monitor to receive updates. An update may include, for example, updates to the illumination sequence, updates to image capture settings, or both. An illumination sequence stored at the particle monitor may specify the order for activing the different illumination sources. The image capture settings may specify focal depths or depths of focus. For example, three-dimensional morphology information may be obtained through a sequence of depths of focus corresponding to different horizontal layers of a translucent particle such as a pollen grain. The ability to update the particle monitor remotely or over a network helps to ensure use of the latest algorithms for quickly and accurately identifying or discriminating particles.

Figure 34:
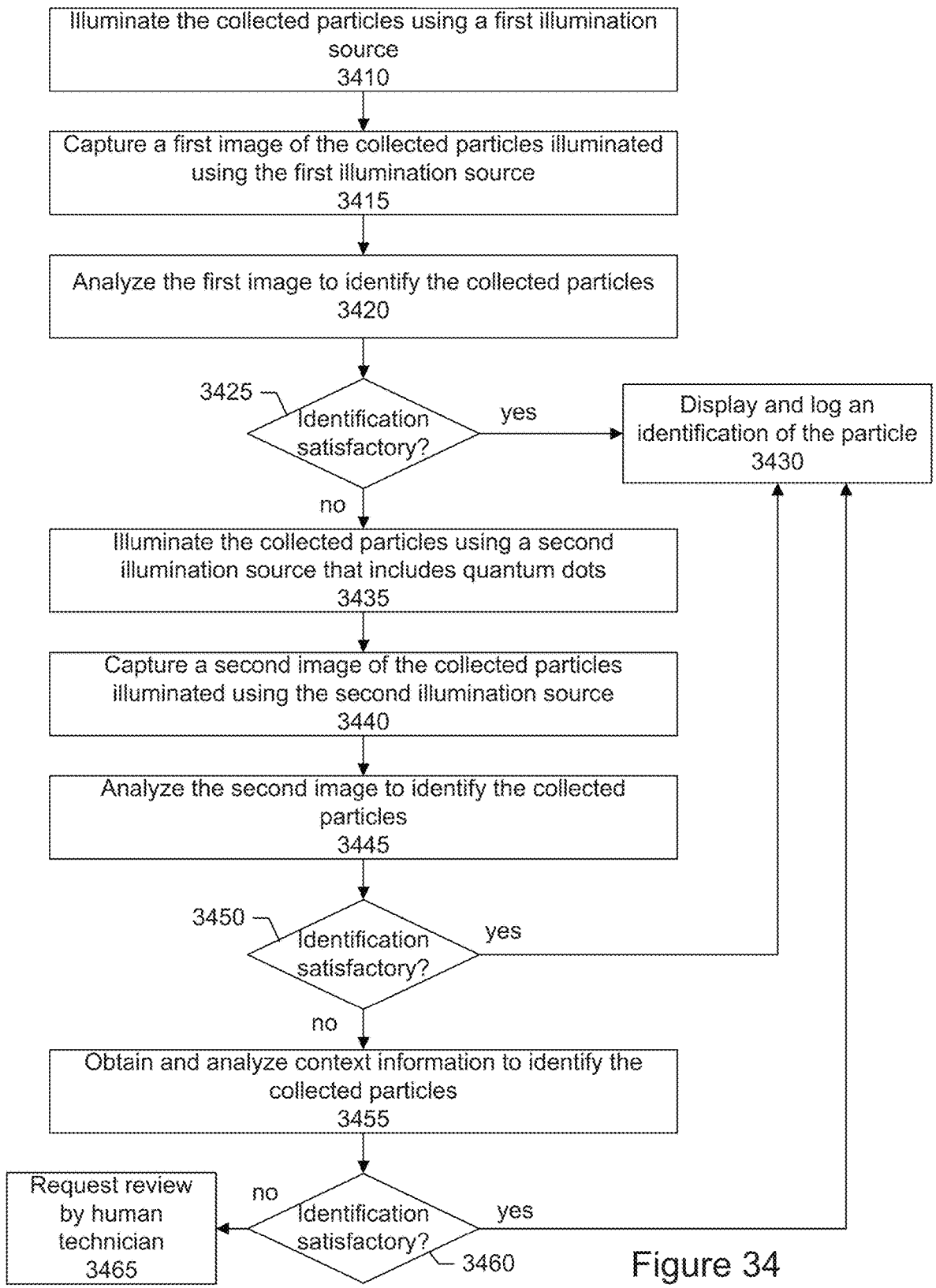
FIG. 34 shows an overall flow of a process for identifying or discriminating particles according to another specific embodiment.

FIG. 34 shows further detail of a flow for analyzing and identifying or discriminating particles that have been collected by the particle monitor. In a step 3410, the collected particles are illuminated using a first illumination source. In a step 3415, a camera sensor of a microscope in the particle monitor captures a first image of the particles while the particles are being illuminated using the first illumination source. That is, a processor of the particle monitor records on storage image data representative of the particles being illuminated using the first illumination source. In a step 3420, the particle monitor analyzes the first image to identify the collected particles.

Figure 35:
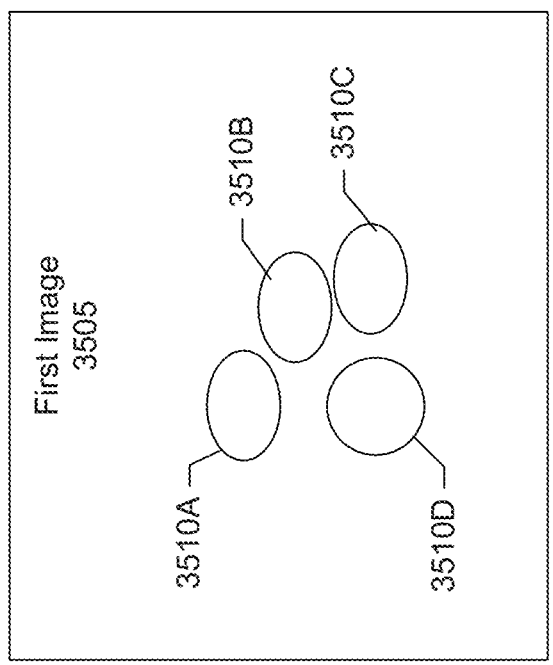
FIG. 35 shows a first image of particles captured under first lighting conditions.

FIG. 35 shows an example of a first image 3505 that may be captured. The first image includes particles 3510A-D that have been captured. Any competent image recognition technique may be applied. In a specific embodiment, an analysis includes a morphology analysis in which geometric features of the particles are examined. The geometric features may be extracted and compared to a reference library of geometric features of known particle types. Examples of geometric features include size, shape, surface texture (e.g., smooth surface versus spikey surface), and so forth.

In a step 3425 (FIG. 34) a determination is made as to whether an identification of particles from the first image is satisfactory as there can be many different particles that share the same or similar morphology. The analysis may include the application statistical algorithms to calculate a degree of confidence in the identification or discrimination. The calculated degree of confidence may be compared to a threshold confidence level. The degree of confidence can be a percentage or other value. The threshold confidence may be configurable such as by a user or administrator.

If the degree of confidence exceeds the acceptable threshold, an identification of the particle may be displayed, the results logged, or both (step 3430).

Alternatively, if the degree of confidence does not exceed or is below the threshold, the particle monitor illuminates the collected particles using a second illumination source that includes quantum dots (step 3435). For example, the first illumination source may be deactivated and the second illumination source may be activated. The illumination or lighting conditions created by the second illumination source are different than the illumination or lighting conditions created by the first illumination source.

In a step 3440, the camera sensor captures a second image of the particles while the particles are being illuminated using the second illumination source including quantum dots. In a step 3445, the particle monitor analyzes the second image to identify the collected particles. In a specific embodiment, the analysis includes analyzing color information recorded in the second image. The analysis may include comparing the first and second images, comparing the second image to a library of reference images, or both.

Figure 36:
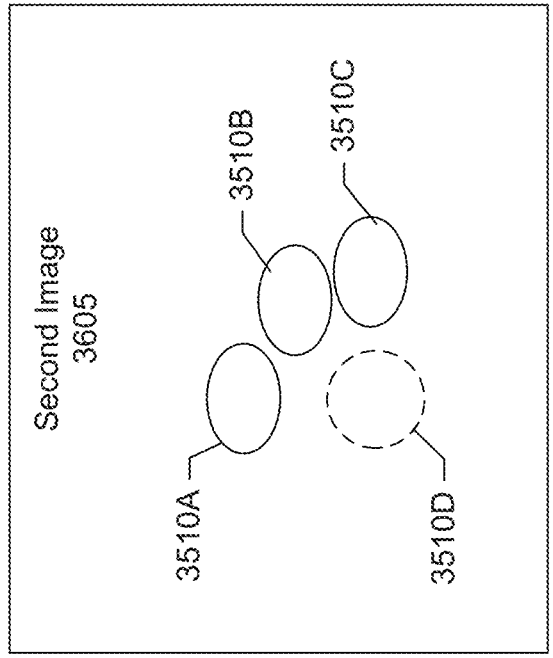
FIG. 36 shows a second image of particles captured under second lighting conditions.

FIG. 36 shows an example of a second image 3605 that may be captured of the particles under illumination provided by the second illumination source including quantum dots. In the example shown in FIG. 36, particles 3510A-C remain visible in the second image. Particle 3510D, however, is drawn in broken lines to indicate that its appearance in the second image as compared to the first image is faint, missing, or less perceptible.

Consider, as an example, that the illumination for the second image included red light or, more specifically, that the emitted quantum dot spectrum includes a narrow spectrum centered on a chlorophyll-a absorption peak such as approximately at 665 nanometers. The spectrum may include a full width half maximum less than 50 nanometers, or less than 25 nanometers. In other words, the emitted quantum dot spectrum is substantially within a chlorophyll-a absorption peak. In the example shown in FIG. 36, the appearance of particle 3510D in the second image as being faint or even missing, absent, less perceptible, or less visible is the result of the particle having absorbed the light rather than scattering the light. In this example, the analysis of the second image can suggest that the particle includes grass pollen because grass pollens typically include chlorophyll-a.

In an embodiment, a method includes identifying an absorption peak of a particular type of particle, collecting particles floating in an environment, illuminating the particles with first light, capturing a first image of the particles while the particles are illuminated with the first light, illuminating the particles with second light, different from the first light, the second light being light corresponding to the absorption peak of the particular type of particle, capturing a second image while the particles are illuminated with the second light, comparing the first and second images, based on the comparison, determining that a particle captured in the first image is less perceptible in the second image than the first image, and identifying the particle as being of the particular type of particle.

In a step 3450 (FIG. 34), a determination is made as to whether the identification is satisfactory. The determination may likewise include calculating a degree of confidence in the identification, applying statistical analyses, comparing the degree of confidence to a threshold confidence level, and so forth. The determination may include factoring in or weighing the results from the analysis of the first image. For example, if a first result from analyzing the first image strongly indicates grass pollen, and if a second result from analyzing the second image strongly indicates grass pollen, an identification of the particles as being grass pollen may be satisfactory.

Thus, if the degree of confidence exceeds the acceptable threshold, an identification of the particle may be displayed, the results logged, or both (step 3430).

Alternatively, if the degree of confidence does not exceed or is below the threshold, the particle monitor obtains and analyzes context information (step 3455). Consider, as another example, that the first result from analyzing the first image strongly indicates that the particles are grass pollen grains but cannot discriminate between two different species of grass. In this case, the particle monitor may issue a request to cloud server 110 for context information such as which types of grass are blooming in the area at the time. Grass types that are not blooming may be eliminated from consideration. The request may include a geographical location of the particle monitor, a time and date of particle capture, or both.

The cloud server receives the request and obtains the relevant context information for the requesting particle monitor. The relevant context information may include, for example, weather conditions and wind patterns corresponding to the location and time of particle capture, pollen types known to be presently blooming at the location of the requesting particle monitor, a listing of pollen types identified by other particle monitors that are near the requesting particle monitor, and so forth, or combinations of these.

In a step 3460, a determination is made as to whether the identification is satisfactory. The determination may likewise include calculating a degree of confidence in the identification, applying statistical analyses, comparing the degree of confidence to a threshold confidence level, and so forth. The determination may include factoring in or weighing the results from the analysis of the first image, second image, or both.

Consider, as an example, that a first result from analyzing the first image indicates grass pollen, a second result from analyzing the second image indicates grass pollen, and that the received context information indicates that grass pollen is currently blooming at the location of the particle monitor and that grass pollen has recently been detected by other particle monitors near the requesting particle monitor.

In this case, the degree of confidence in the particle as being grass pollen may exceed the acceptable threshold, and an identification of the particle as being grass pollen may be displayed, the results logged, or both (step 3430).

Nearby particle monitors may be defined as particle monitors within a specified radius of the requesting particle monitor. In an embodiment, the cloud server calculates a distance between the requesting particle monitor and another particle monitor. If the distance is less than the specified radius, the other particle monitor is considered nearby. If the distance is greater than the specified radius, the other particle monitor is considered not nearby. The specified radius can be any value. The radius may be configurable such as a user, administrator, or both.

Recent particle detections by other particle monitors may be defined as detections occurring within a specified time window or duration from a time of the particle capture. The duration may be, for example, 12, 24, 48, or more than 48 hours. The duration may be less than 12 hours. The duration can be any value. The duration may be configurable such as by a user, administrator, or both. In an embodiment, the cloud server calculates a duration between a time of particle capture by the requesting particle monitor and a time of particle capture by another particle monitor. If the duration is less than the specified duration, the particle detections made by the other particle monitor may be considered relevant. If the duration is greater than the specified duration, the particle detections made by the other particle monitor may be considered irrelevant.

If the degree of confidence does not exceed or is below the threshold, the particle monitor requests a review by a human technician (step 3465). For example, the particle monitor issue the request to the cloud server. Upon receiving the request, the cloud server may generate an alert that is transmitted to the human technician. The alert may include, for example, an email, text message, or other notification. The request from the particle monitor may include or be accompanied by images of the captured particles that the particle monitor was unable to identify with satisfaction.

It should be appreciated that the steps shown in FIG. 34 may occur in an order different from what is shown. For example, in FIG. 34, obtaining context information (step 3455) is after capturing and analyzing the second image (steps 3440 and 3445). This is not necessarily, however, always the case. In another embodiment, context information be may be obtained before capturing and analyzing the second image.

For example, context information may be obtained and stored by the particle monitor periodically such as at a specified time. The specified time can be during off-peak hours such as nightly (e.g., 2:00 AM) when the network is less likely to be loaded. In this specific embodiment, at the specified time, a particle monitor issues to a server a request for context information. The request is time-stamped and includes a geographical location of the particle monitor. The server receives the request. Based on the time and geographical location of the particle monitor, the server responds to the requesting particle monitor with relevant context information. The particle monitor receives and stores the relevant context information. The previous context information stored at the particle monitor may be deleted, removed, or replaced with the newly received context information.

The relevant context information may include current weather conditions, forecasted weather conditions (e.g., predicted weather conditions for the next 12 hours, the next 24 hours, and so forth), pollen types currently in bloom based on the time and location of the requesting particle monitor, pollen types expected or forecasted to be in bloom based on the time and location of the requesting particle monitor, a listing of particle types that have recently been identified by other nearby particle monitors, or combinations of these. Weather conditions may include wind speed, wind patterns, wind direction, humidity levels, temperature, chances of precipitation, precipitation activity, precipitation amounts, type of precipitation (e.g., drizzle, rain, sleet, hail, or snow), barometric pressure, and so forth.

Pre-fetching or caching the context information locally on a periodic basis helps to ensure that the context information is up-to-date and available at the particle monitor when needed. Pre-fetching the context information can help to increase the speed of particle analysis because the context information will be available from storage local to the particle monitor. In other words, the context information is cached locally at the particle monitor.

Context information may be obtained according to a pre-determined schedule. The pre-determined schedule can be hourly, twice-daily, daily, or any other frequency as desired. The schedule can be configurable such as by a user, administrator, or both. Increasing the frequency at which the context information is pre-fetched and cached helps to ensure that the context information is up-to-date. However, frequent caching increases the number of connection requests that the server must service and consumes other resources such as network bandwidth. Factors to consider in determining the frequency at which context information is pre-fetched include the rate at which the weather is expected to change, length of pollen blooming cycles, and other factors. In another embodiment, the context information is obtained on-demand.

In an embodiment, the particle monitor may capture any number of images of the particles to make an identification. This includes, for example, one, two, three, four, five, six, seven, eight, nine, ten, or more than ten images. In an embodiment, if a particle cannot be satisfactorily identified from a first image, the monitor may capture a second image of the particle. The conditions under which the second image was captured may be different from conditions under which the first image was captured.

The conditions may include differences in lighting or illumination conditions (e.g., white light, infrared light, ultraviolet light, or quantum dot illumination), different focal lengths, different tape positions, or combinations of these.

An analysis may be performed using three or more images compared together or analyzed separately. An analysis may include comparing one illumination source image to two different quantum dot wavelength images. Images may be captured in any order. For example, a first image of a particle may be captured when the particle is illuminated with an illumination source not including quantum dots. A second image of the particle may be captured when the particle is illuminated with a quantum-dot illumination source. The first image may be captured before the second image. The second image may be captured after the first image. The first image may be captured after the second image. The second image may be captured before the first image.

In an embodiment, a method may include illuminating a particle with first light having a first emission spectra, capturing a first image of the particle illuminated with the first light, illuminating the particle with second light having a second emission spectra; capturing a second image of the particle illuminated with the second light; illuminating the particle with third light having a third emission spectra; capturing a third image of the particle illuminated with the third light; and analyzing the first, second, and third images to identify the particle, where the first emission spectra is different from the second and third emission spectra, and the second emission spectra is different from the first emission spectra. The second emission spectra may be from a first set of quantum dots comprising size- or composition-tuned quantum dots tuned to emit the second emission spectra. The third emission spectra may be from a second set of quantum dots comprising size- or composition-tuned quantum dots tuned to emit the third emission spectra. The method may include analyzing at least one of the first, second, or third images separately from another of the first, second, or third images. The method may include comparing at least one of the first, second, or third images with another of the first, second, or third images.

In an embodiment, a method includes imaging a particle, advancing a collection media (e.g., tape) having the particle slightly, and imaging the same particle again. Optical image processing could then take advantage of this in several ways. Even if the tape only moves very slightly, it is likely to randomize how camera pixels line up with features of the particle, thus allowing the system to at least partially average out effects of discrete pixels on the image. Looking at the same particle from two sufficiently different directions enables the system to apply the principles of binocular vision to obtain at least crude depth or 3-D information. As discussed, particle height information may be derived from the length of observed shadows with oblique lighting, and observing shadows from different directions will enrich the shadow information. All these techniques not only apply to pairs of images at two tape advance locations, but also three or more images from three or more tape advance locations.

In an embodiment, a method includes collecting particles onto a collection media; while the collection media is in a first position, capturing, via a camera sensor, a first image of a particle; moving the collection media from the first position to a second position, different from the first position; while the collection cartridge is in the second position, capturing, via the camera sensor, a second image of the particle. In an embodiment, the illumination conditions under which the first image is generated are the same as the illumination conditions under which the second image is generated. In another embodiment, the illumination conditions under which the first image is generated is different from the illumination conditions under which the second image is generated. The moving of the collection media may be in a forward or reverse direction.

It should be appreciated that aspects and principles of the system may be applied to analyzing a video of the particles that have been collected. For example, in a specific embodiment, a particle monitor includes a video recorder. The video recorder can record a single video recording of the particles that have been collected. During the recording of the single video, the collection media upon which the particles have been trapped may remain stationary and the particles may be illuminated with a series of different lighting conditions (e.g., white light, one or more different quantum-dot illumination sources, infrared light, or ultraviolet light). The system can then analyze the single video (e.g., single video file) to identify or discriminate the particles. For example, one or more frames of the video may be analyzed. Alternatively, the collection media upon which the particles have been trapped may move continuously during the entire recording or during at least a portion of the recording. While the collection media is moving, the conditions under which the particles are illuminated may remain the same or may change. An analysis may include analyzing both a still image of a particle and a video recording of the particle.

Figure 38:
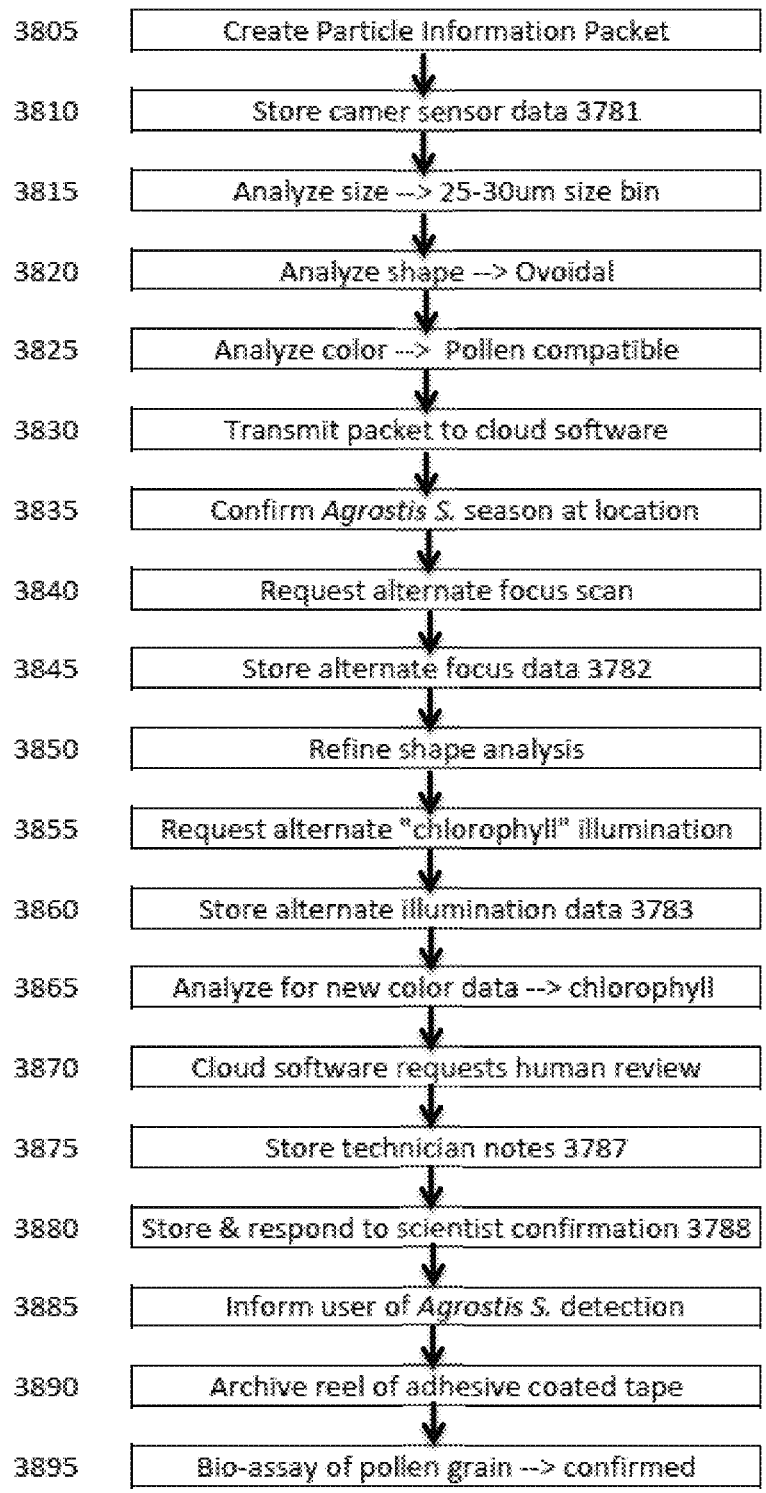
FIG. 38 shows a block diagram of history for the particle information packet according to an embodiment.

FIG. 37 illustrates the contents of an exemplary particle information packet 3700 that may be generated by particle monitor 105 in an embodiment, in connection with analyzing particles captured by the particle monitor. FIG. 38 shows a particle information packet history.

Referring now to FIG. 37, shown are parameters of a data structure storing characteristics of a particle and metadata associated with the particle. The data structure may be stored in the memory or storage of a physical computing device. The data structure may be implemented, for example, as a table of a database. While FIG. 37 shows some specific examples of particle characteristics and metadata that may be collected, derived, and stored for a particle, it should be appreciated that there can be instead or additionally other particle characteristics, associated metadata, or both that may be stored.

Consider, as an example, a particle monitor owned by a consumer with a severe allergic reaction to the pollen of spreading bent grass *Agrostis* Stolonfera. In this context, FIG. 38 illustrates an example hypothetical history of one particle information packet.

When a particle is observed in the field of view of the camera sensor of the consumer's particle monitor, a particle information packet 3700 (FIG. 37) is created (step 3805—FIG. 38). At creation, it includes a particle ID number 3712 (FIG. 37), a particle ID block 3720 containing items 3721 through 3726, as well as an objectives block 3730 with an application type 3732 of "personal health" and a definition of particles of interest 3734 of "*Agrostis* Stolonfera pollen."

In the example shown in FIG. 37, the particle ID block includes a timestamp 3721, particle collection device serial number 3722, device GPS coordinates 3723, adhesive-coated tape reel number 3724, x-coordinate of particle along length of tape 3725, and y-coordinate of the particle (perpendicular to the length of tape) 3726.

In a specific embodiment, the particle identification subsystem includes a pixel-to-tape mapping unit that maps a location of a particular particle that has been captured within an image to the particle's physical location on the tape. The mapping unit determines a first location of a particle within an image. The first location may be a set of pixel coordinates. For example, a pixel coordinate X may represent the particle's location as measured along an x-axis from a reference point in the image. A pixel coordinate Y may represent the particle's location as measured along a y-axis from the reference point in the image. The pixel coordinates can be mapped into real space or into real x-y coordinates as measured from a reference point on the tape.

The particle collection cartridges may be assigned unique serial numbers so that images of the particles can be associated with corresponding collection cartridge having the physical particles. As discussed, in an embodiment, the particle monitor includes a counter that tracks a position of the tape. For example, the counter may track an amount or length of tape taken up by the uptake reel, an amount or length of tape unspooled from the supply reel, or both. Tracking the position of the tape allows for cross-referencing the images with the corresponding physical particles on the tape.

In another specific embodiment, the tape may include a set of markers that can be captured in the particle images. The markers may be individually or sequentially numbered and distributed at various intervals along a length of the tape. An interval may correspond to a width of a field of view of the camera sensor so that a marker associated with the interval will be captured in an image. The marker allows for cross-referencing the image with the portion of tape where the corresponding physical particles have been trapped. The markings may be made using any technique for making a visible impression on the tape including, for example, printing, silkscreen printing, stamping, or chemical processing. Alternatively, the tape may include a magnitizable layer for magnetic marking and readout of tape locations.

At this point, status block 3740 contains a measurement status flag 3742 and an analysis status flag 3744 with no bits set, and null work-in-progress and definitive particle classifications 3746 and 3748. This is the state of particle information packet 3700 at step 3805 of FIG. 38.

At step 3810 (FIG. 38), the particle monitor embedded software stores into data block 3780 (FIG. 37) sensor data 3781 for those RBG camera pixels including and surrounding the detected particle. At this step, a bit in measurement status flag 3742 is set to indicate the capture of camera sensor data 3781. At this point, no decision has been made whether the detected particle is even a pollen grain rather than, for example, a dust particle.

The first analysis step is step 3815 (FIG. 38). This first analysis step involves estimating the diameter or longest major axis of the detected particle. From this measurement there results a work-in-progress or preliminary particle classification 3746 (FIG. 37) such as "<5 microns" (less than 5 microns), "10-15 microns" (between 10 and 15 microns), "35-40 microns" (between 35 and 40 microns) or ">200 microns" (greater than 200 microns). A corresponding bit in the analysis status flag is set. If the result had been "<5 microns" (less than 5 microns) or ">200 microns" (greater than 200 microns), a quick definitive particle classification 3748 of "not *Agrostis* Stolonfera" would have been made on the basis that the particle size is not compatible with the particles of interest 3734.

However, in this case we imagine a work-in-progress classification 3746 of "25-30 microns" which is compatible with the particles of interest. However, this size range is also compatible with many particles that are not of interest, such as dust particles that happen to be in this size range.

Given that the possibility remains that the packet might correspond to a particle of interest, the software of the pollen monitor makes a decision to analyze particle shape. This is step 3820 of FIG. 38. If the outcome had been "narrow rod," or "spikey ellipsoid," a definitive or final particle classification 3748 (FIG. 37) of "not *Agrostis* Stolonfera" would have been made.

However, we imagine a resulting work-in-progress classification 3746 of "smooth ovoidal particle of 25-30 micron size." In engineering practice, the work-in-progress classification 3748 can be a numerical code that can be configured, by for example, scientists and software engineers or other users. As with all analysis steps, another bit in the analysis status flag 3744 is set after completion of this analysis step.

The work-in-progress classification of "smooth ovoidal particle of 25-30 micron size" does not exclude the possibility that the particle is a pollen grain of *Agrostis* Stolonfera. As a result, in step 3825 (FIG. 38), the pollen monitor's software makes a decision to analyze color information in camera sensor data 3781 (FIG. 37). If the result had been "color of soot" or "color of dust," the processing of the particle information packet 3700 would have ended with a "not *Agrostis* Stolonfera" definitive classification 3748. However, to provide a more instructive example, imagine step 3825 (FIG. 38) results in a work-in-progress classification 3746 (FIG. 37) of "smooth ovoidal particle of 25-30 micron size with pollen compatible color."

Note that in steps 3820 (FIG. 38) and 3825, no new data is collected, only new analyses of previously measured data stored in data block 3780 (FIG. 37).

At the completion of step 3825 (FIG. 38), the embedded software of the particle detector has not yet reached a definitive classification, and may not have the best information to decide what comes next. At such a point, the particle detector looks for guidance from software on the cloud. In step 3830, the embedded software transmits the particle information packet 3700 (FIG. 37) to the cloud.

The cloud software has access to great deal more information than does the embedded software of the particle monitor. For example, the cloud software may have access to databases where the system collects and stores relevant information such weather patterns, elevations at various GPS coordinates, historical records of past pollen seasons, as well as which plants are currently producing pollen in which geographical areas. The pollination season for *Agrostis* Stolonfera is sometime in the spring through fall depending on the elevation and latitude corresponding to the device GPS coordinates 3723 (FIG. 37) of particle identification block 3720. For example, if time stamp 3721 corresponds to the middle of winter, the presence of *Agrostis* Stolonfera can be excluded. However, in FIG. 38 we consider the case that the contextual information available on the cloud does not exclude detection of particles of interest 3734 (FIG. 37).

To provide better discrimination between types of pollen, the cloud software may decide that better morphology information is desirable and in step 3840 (FIG. 38) sends a request to the particle monitor to collect further camera images of the pollen with one or more alternate focal depths. Focal depth may be varied by mechanical movement of lens and/or camera sensor, by electronic control of a variable lens, by software control of processing of image data from a light-field camera system, or combinations of these.

The request received by the particle monitor triggers step 3845 and the requested measurement are made and added to the alternate focus data 3782 (FIG. 37) of data block 3780. With this additional data, in step 3850, a more refined shape or morphology analysis is performed. The analysis of step 3850 may be performed by embedded software of the particle monitor (e.g., analyzed locally at the particle monitor), by cloud software (e.g., analyzed remotely by a cloud server), or both.

By capturing images of a pollen grain (or other particle) at multiple focal depths, all parts of a pollen grain can be brought into focus, thus providing more complete morphological information. For translucent pollen grains, a scan of focal depth may be used to capture three-dimensional pollen structure information.

In step 3855, the cloud software also sends a request to the particle monitor to collect further camera images with an alternate illumination source. In step 3860 the alternate illumination data is stored as item 3783 (FIG. 37) in data block 3780.

Here we assume that the pollen monitor is equipped with a quantum-dot LED illumination source tuned to the red absorption line of chlorophyll-a. As discussed above, a distinguishing characteristic of grass pollen is the presence of a chlorophyll color signature. The quantum-dot LED illumination source may be optional hardware that was included in the particle monitor configuration due to the consumer's sensitivity to grass pollen; in this sense the definition of particles of interest 3734 may not only influence processing of a particle information packet 3700, but also influence the hardware configuration of the particle monitor. Let us assume that such a chlorophyll sensitive alternate illumination is used and in step 3865 (FIG. 38), analysis (local, on the cloud, or both) of all the color data in block 3780 (FIG. 37) confirms the presence of chlorophyll.

At this point, the evidence is strong that the detected particle is a grain of *Agrostis* Stolonfera pollen. However, before disturbing the consumer with an alert, it may be prudent to obtain a second opinion from a human technician. In the scenario of FIG. 38, the cloud software sends a request for a second opinion from a trained technician. In step 3875, resulting technician notes are stored in data block item 3787 (FIG. 37). The request may include particle data collected by the system and the system's determination of the type of pollen based on the particle data. This information may be displayed, for example, on an electronic screen such as via a web page provided by the system. The web page is accessible by the trained technician. The web page may further include an input box that the technician can use to enter notes regarding the accuracy of the identification and other information.

The technician may in turn request a third opinion by a scientific specialist whose notes are captured in step 3880. In this scenario, we imagine that the scientific specialist is fully convinced and "*Agrostis* Stolonfera" becomes the definitive particle classification 3748 (FIG. 37). It is now time to inform the consumer that allergenic pollen has been detected (step 3885).

In the interests of cost and a fast response, it may well be more exceptional than routine to involve humans, as in steps 3875 and 3880, in which it is otherwise an automated particle (e.g., pollen or mold spore) detection and classification system. This exceptional scenario is considered here to more fully describe a deeply multi-tiered pollen discrimination scenario. A deeply multi-tiered scenario may also be one where the user of a particle monitoring device has required human review of the particle data every so often (e.g., periodically). An example of this is an institutional, commercial, or single user with multiple systems deployed across a region and operating 24 hours a day 7 days a week. In such a scenario, human involvement as described in steps 3875 and 3880 may take place as part of a quality assurance procedure.

For example, a human review of particle data may be required after one hundred, one thousand, ten thousand, a million, or another number of particle detections have occurred. A human review of particle data may be required every hour, once a day, once a week, once a month or at some other interval of time. The criteria or frequency for when human review of particle data is required can be configurable such as by a user or administrator of the system. The system (e.g., pollen monitor, pollen cloud server, or both) can track this criteria to determine when a human review of particle data is required. When a human review of particle data is required, the system can send out a notification to the human reviewer to request a review of the particle data. The request may include the particle data and a pollen identification made based on the particle data. The human reviewer can review the particle data to see whether or not the pollen or other particle identification was correct. Further leveraging of the talents of the human reviewer may be provided by using results of human reviews as input to automated machine learning algorithms so that reliance on human review decreases with time.

In a specific embodiment, a feature of the system includes providing consumers or customers of the system with human interaction or a human touch. Rather than just an automated text message alert, in some cases a phone call with follow-up questions such as "How are you feeling?" from a customer service specialist of the system or perhaps the consumer's doctor may be well appreciated, add value and create loyalty.

Even after the consumer has been alerted, the particle information packet may continue to be processed for quality control and algorithm development purposes. In step 3890, the used reel of adhesive-coated tape containing the detected particle is collected and stored in an archive. Later, in step 3895, a bioassay using anti-bodies specific to the troublesome antigens of *Agrostis* Stolonfera is performed to verify beyond a shadow of a doubt that the particle was correctly classified—or to learn that a mistake was made and that the particle information packet should be closely studied to determine what changes need to be made to the algorithms of the various tiers of the pollen discrimination system. Depending on a particle information packet's history, the data block 3780 may also contain information from the cloud on local weather conditions 3785, information from the cloud on known seasonal allergens and pathogens 3786, laboratory microscope images 3789 of archived particles, bio-assay data 3790, expert-technician notes 3791 and/or expert scientist notes 3792.

Figures 39A, 39B:
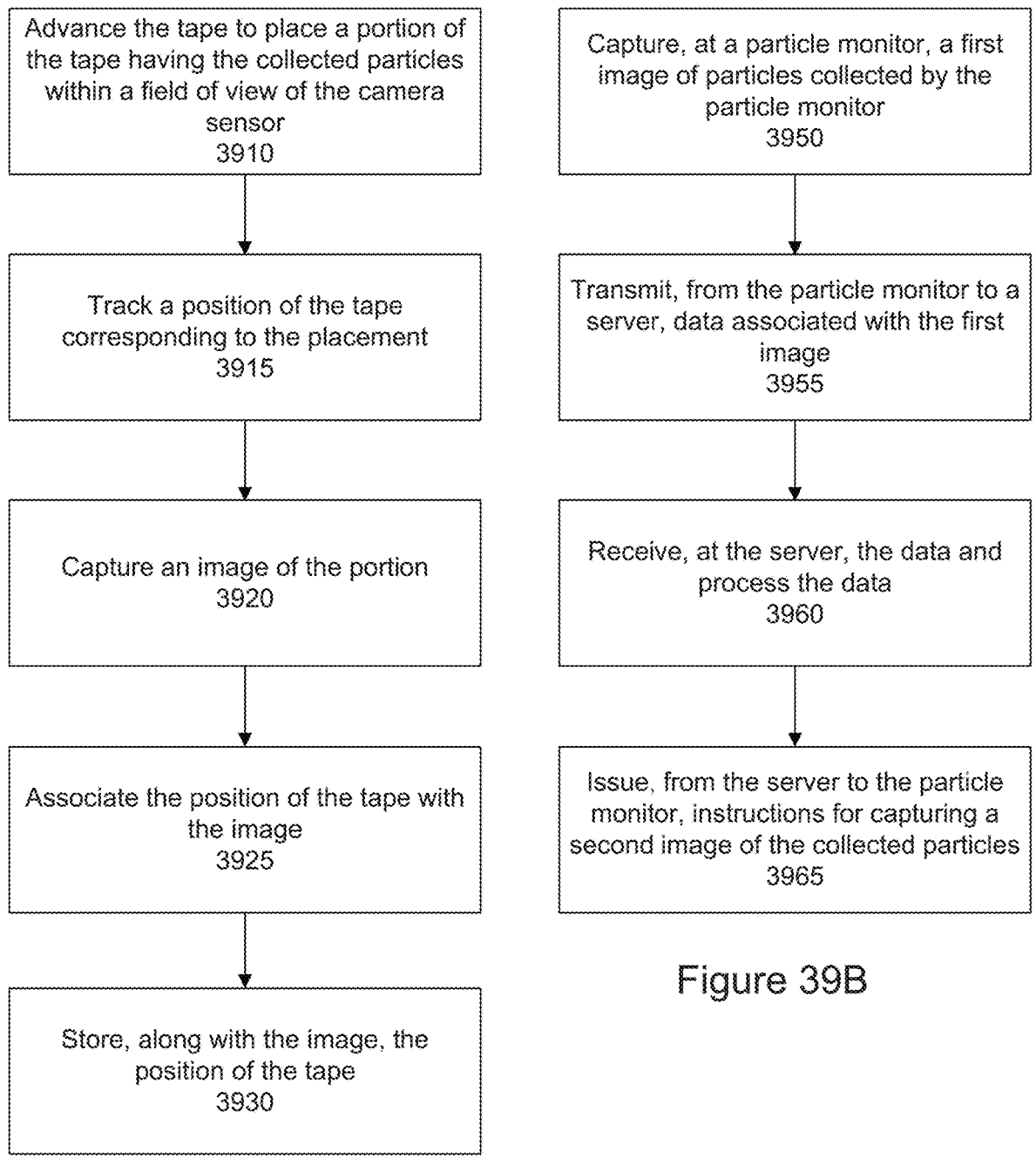
FIG. 39A shows a flow of a process for associating an image of the collected particles with their corresponding location on the adhesive coated tape according to an embodiment.
FIG. 39B shows a flow of a process for server-aided particle identification or discrimination.

FIG. 39A shows a flow of a process for associating an image of the collected particles with their corresponding location on the adhesive coated tape. In a step 3910, particle monitor 105, in an embodiment, advances the tape to place a portion of the tape having the collected particles within a field of view of the camera sensor. In a step 3915, the particle monitor tracks a position of the tape corresponding to the placement. For example, the position of the tape may be measured along a length of the tape between a reference point and the position. The reference point may be, for example, a beginning of the tape, an ending of the tape, or any arbitrary reference point along the tape.

In a step 3920, an image of the portion is captured. In a step 3925, the position of the tape at which the image was taken is associated with the image. In a step 3930, the image and tape position is stored. For example, the image may be tagged with the position of the tape. The position of the tape may be stored as metadata associated with the image.

Storing the position of the tape at which the image was taken allows that particular portion of the tape having the actual physical particles to be later accessed. For example, the tape may be mailed to a laboratory for further analysis. The tape position information may be referred to as an address. Table H below shows an example of metadata information that may be stored, such as within an image index, that cross references an image of particles with a portion of the adhesive coated tape at which the physical particles are located.

TABLE H

| Image ID | Cartridge ID | Location (mm) |
|---|---|---|
| image001 | cartidge001 | 500 |
| image002 | cartidge001 | 800 |
| ... | ... | ... |

In the example in table H above, a first column stores an identifier that uniquely identifies the image. A second column stores an identifier that uniquely identifies the cartridge. A third column stores a location on the tape of the cartridge that maps to a position of the tape at which the image was taken. In a specific embodiment, location may be a distance measurement. The distance may be measured along a length of the tape from a beginning (or ending) of the tape. For example, a first row of the table includes the location value "500 mm" for "image001." This can indicate, for example, that an edge of the image corresponds to a location on the tape that is 500 mm from a beginning end of the tape. The location on the tape can correspond to an edge of a field of view within which the image was taken.

FIG. 39B shows a flow of a process for server-aided particle identification or discrimination. In a step 3950, the particle monitor captures a first image of particles collected by the particle monitor.

In a step 3955, the particle monitor transmits to the server data associated with the first image. The data may be from a preliminary analysis performed by the particle monitor on the first image. The preliminary analysis may include, for example, a morphology analysis. In a specific embodiment, rather than sending the actual first image to the server, the particle monitor sends a smaller packet of information to the server as image files can be quite large (e.g., several megabytes in size). Reducing the amount of data that is sent over the network helps to conserve network bandwidth.

In another specific embodiment, the particle monitor may send a portion of the first image, rather than the entire first image. For example, the particle monitor may perform a preliminary analysis in which the particle monitor identifies a portion of the image as containing a particle. Other portions of the image may not include particles or may include particles that the particle monitor quickly concludes are not of interest. The portion of the first image having the particle may be cropped, thus reducing the file size. In another specific embodiment, the particle monitor may transmit the entire first image to the server.

Determining the amount of data to send can be based on a degree of confidence in a preliminary assessment of the captured particles. The amount of data that is transmitted by the particle monitor to the server can vary inversely with the degree of confidence in the preliminary assessment. In other words, when the particle monitor calculates a high degree of confidence in the preliminary assessment (e.g., degree of confidence is above a threshold), less data may be transmitted to the server (e.g., portion of first image). When the particle monitor calculates a low degree of confidence in the preliminary assessment (e.g., degree of confidence is below the threshold), more data may be transmitted to the server (e.g., the entire first image).

In a step 3960, the server receives the data from the particle monitor and processes the data. The server generally has access to more computing resources than the particle monitor. Such resources may include more powerful processors, more storage capacity, and the like. The additional computing resources allow the server to execute identification algorithms that might otherwise crash the particle monitor when executed on the particle monitor. The server may execute, for example, a more complex image recognition algorithm in order to identify the particles. Performing at least some of the analysis on the server also helps to conserve the limited battery supply of the particle monitor.

In a step 3965, based on the server-side processing of the received data, the server issues to the particle monitor instructions for capturing a second image of the collected particles. The instructions may include, for example, a specification of the conditions under which the particles are to be illuminated (e.g., illuminate under UV light, illuminate under IR light, illuminate under red light, illuminate under blue light, and so forth), a specification of the focal length, tape positioning information, or combinations of these.

The tape positioning information may instruct the particle monitor to advance the tape forward by a certain amount or rewind the tape backwards by a certain amount. For example, the first image may have captured a portion of particle whereas a remaining portion of the particle may have been outside the field of view of the camera sensor. In this case, the tape may be advanced forward or backward so that the remaining portion of the particle may be brought into the field of view for the second image.

FIGS. 40-43 show various views of particle monitor device 4005 according to another specific embodiment. The particle monitoring device samples ambient air, captures particles (e.g., pollen or mold spores) on an adhesive-coated tape, images captured particles with a camera lens and camera sensor, and archives adhesive coated tape with captured particles on a take-up reel.

Figure 40:
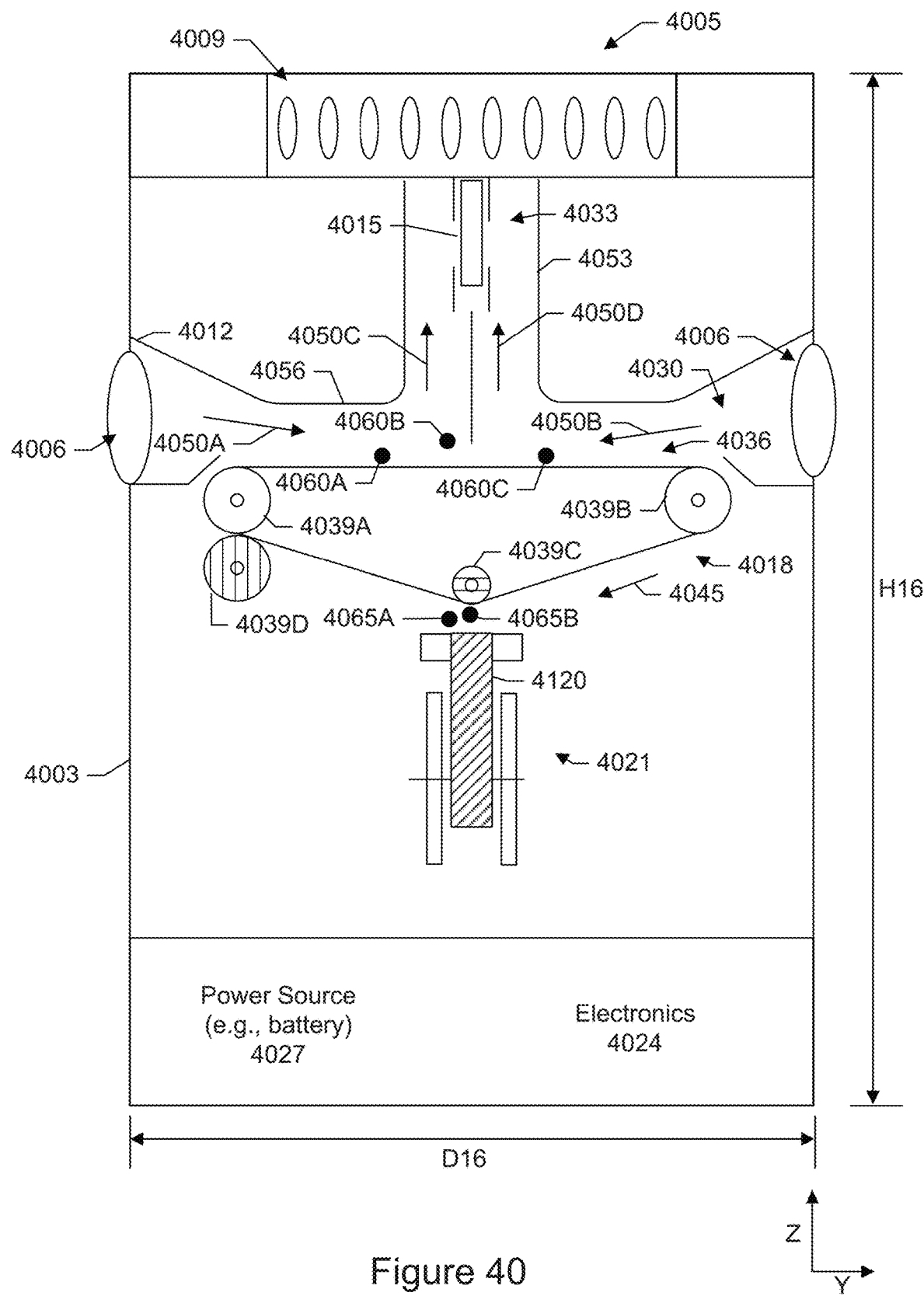
FIG. 40 shows a side view of a particle monitor according to another specific embodiment.
Figure 41:
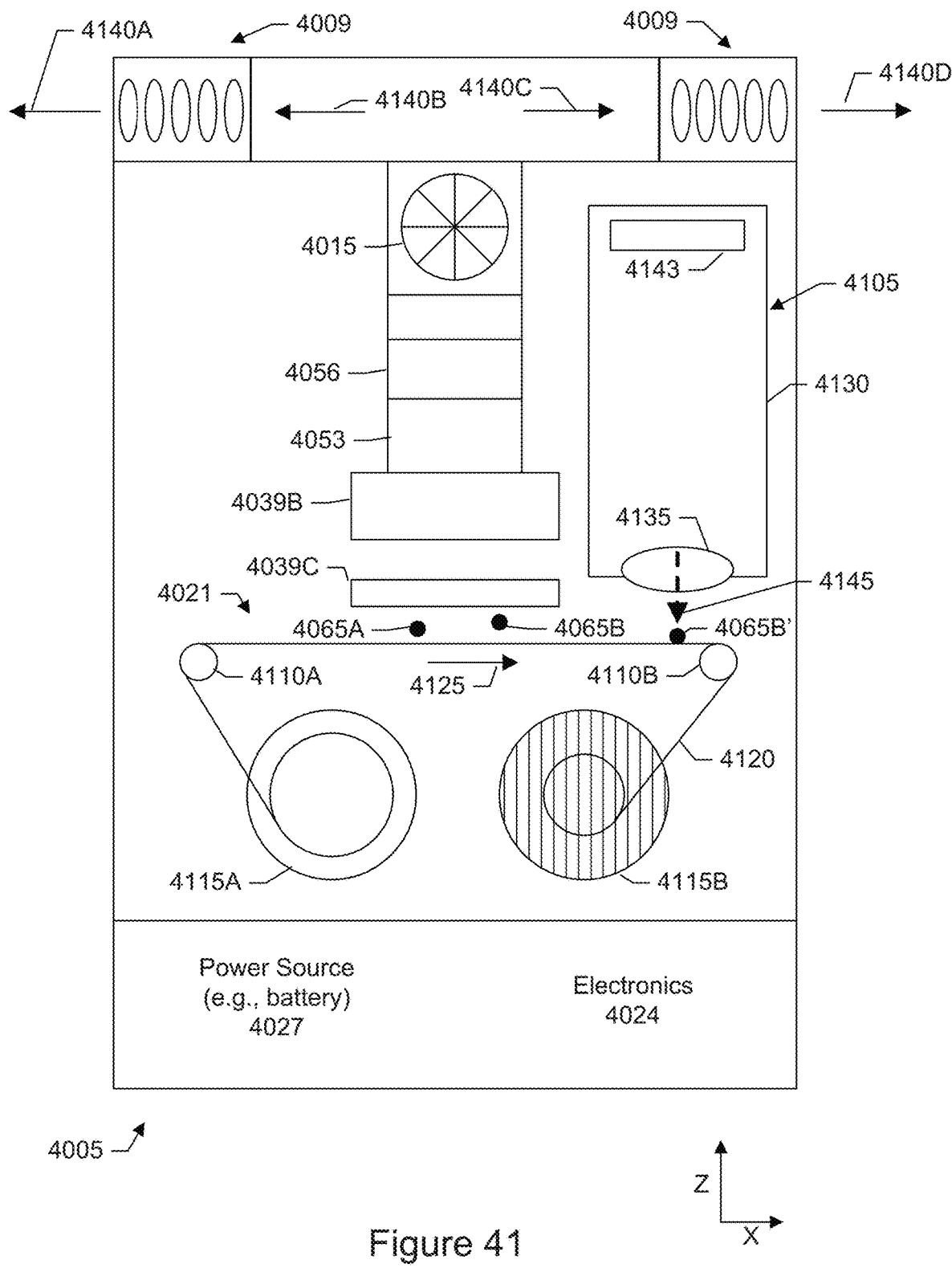
FIG. 41 shows another side view of the particle monitor shown in FIG. 40.
Figure 42:
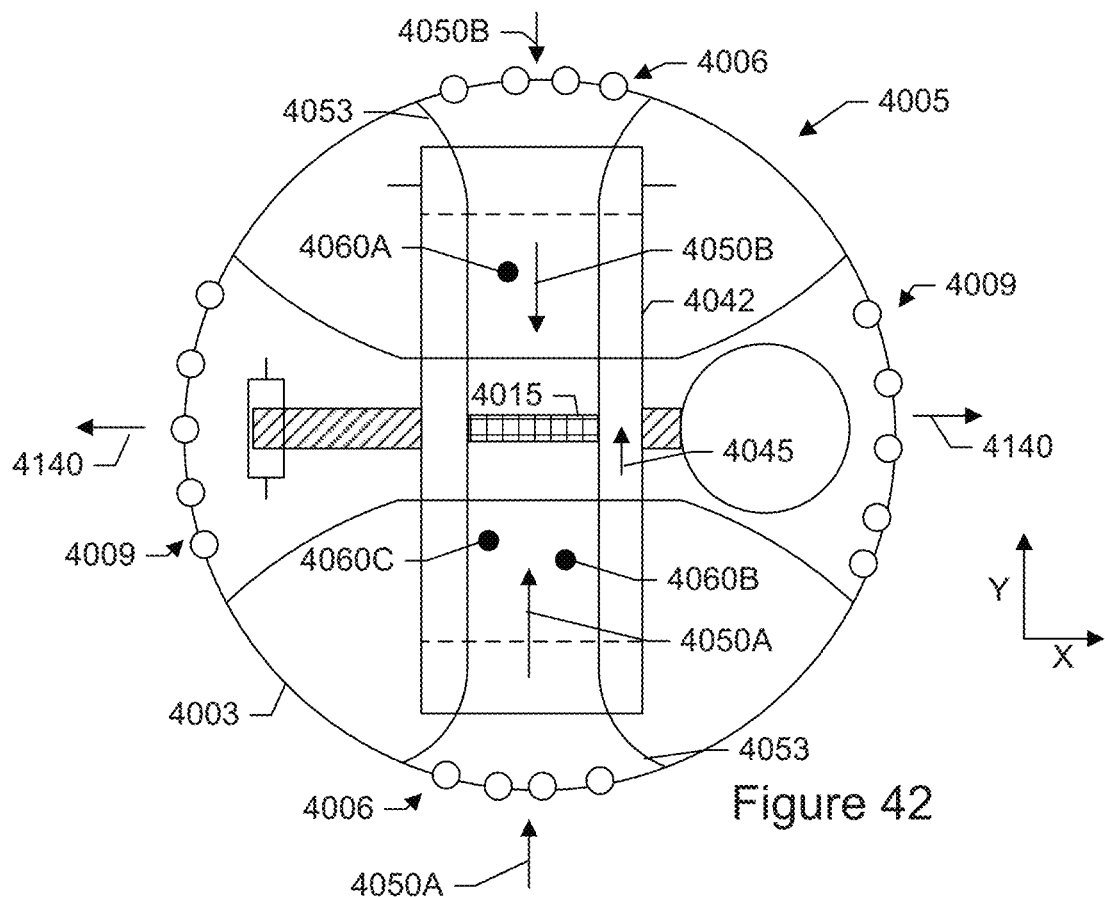
FIG. 42 shows a top cross-section view of the particle monitor shown in FIG. 40.
Figure 43:
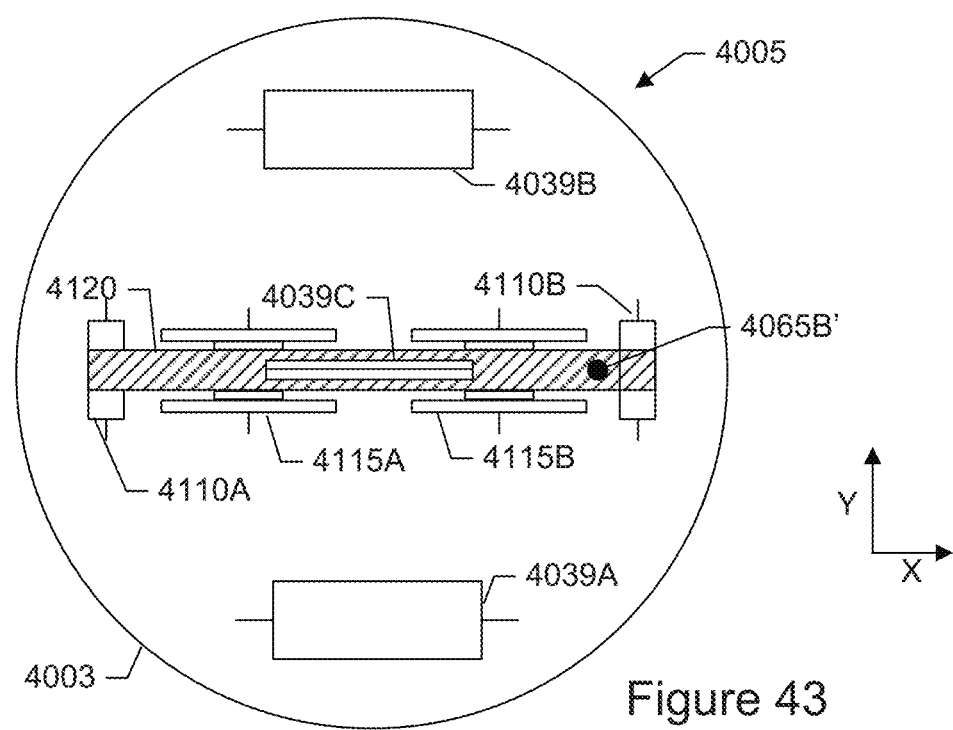
FIG. 43 shows another top cross-section view of the particle monitor shown in FIG. 40.

Camera-image data and the results of its analysis may be stored or logged for later use. Likewise, physical samples of pollen and other particles may be stored or archived for possible later retrieval. FIG. 40 shows a side view of the collection device in a Y-Z plane. FIG. 41 shows a side view of the collection device in an X-Z plane. FIG. 42 shows a plan view of the collection device. FIG. 43 shows another plan view of the collection device.

Referring now to FIG. 40, this particle collection device includes a cylindrical enclosure, cabinet, or housing 4003 having a set of intake vent holes 4006 and a set of outtake or exhaust vent holes 4009. The intake vents are located on a side surface of the enclosure between a top end of the enclosure and a bottom end of the enclosure, opposite the top end. The intake vents are positioned closer to the top of the enclosure than the bottom. The outtake vents are at the top of the enclosure.

Internal components include a duct 4012 connected between the intake and outtake vents, a blower 4015 positioned inside the duct, a first conveyor assembly 4018 below the duct, a second conveyor assembly 4021 below the first conveyor assembly, an optical microscope 4105 (FIG. 41), electronics 4024 (e.g., processor or network interface card), and a power source (e.g., battery) 4027. The power source and electronics are housed at the bottom of the enclosure. The power source supplies power to the blower, conveyor assemblies, optical microscope, and other electrical components of the collection device.

The duct includes a horizontal segment 4030 and a vertical segment 4033. In the example shown in FIG. 40, a bottom end of the vertical segment is connected to a middle portion of the horizontal segment. The vertical segment extends along a central or longitudinal axis of the enclosure. The horizontal segment is orthogonal to the vertical segment. The intake vents open into the horizontal segment of the duct. The outtake vents are at a top of the vertical segment of the duct. A bottom portion of the horizontal segment includes an opening 4036 between opposite intake vents.

First conveyor assembly 4018 includes rollers 4039A, B, C, and D, and a non-stick tape 4042 (see FIG. 42). A roller may be referred to as a pulley or drum. The non-stick tape passes around rollers 4039A, B, and C and above roller 4039D. Roller 4039D is controlled by a stepper motor (indicated the figure by a pattern of vertical lines) and is coated with a sticky adhesive. Via roller 4039D, the stepper motor controls the motion of the non-stick tape so that it moves in a direction as indicated by an arrow 4045. A portion of the non-stick tape is exposed through opening 4036. Roller 4039C is provided with a vibrator or mechanism to vibrate at acoustic or ultrasonic frequencies (indicated in the figure by a pattern of horizontal lines).

Second conveyor assembly 4021 is below the first conveyor assembly and is oriented orthogonally to the first conveyor assembly. Second conveyor assembly 4021 (as shown in FIG. 41) includes rollers 4110A and B, reels 4115A and B, and an adhesive coated tape 4120. The adhesive coated tape is supplied by reel 4115A, passes around or is guided by rollers 4110A and B, and is collected by reel 4115B. A motion 4125 of the adhesive coated tape is driven via take-up reel 4115B by a second stepper motor as indicated in the figure by a pattern of vertical lines.

The optical microscope includes an optical column 4130 with objective lens array 4135 and a camera-image sensor 4143.

Referring now to FIG. 40, blower 4015 drives a flow of air into the intake vents and out the outtake vents. More specifically, arrows 4050A-D indicate the flow of sampled ambient air, perhaps containing pollen and other allergenic substances, into the device via the intake vent holes. Vertical walls 4053 (see FIG. 42) and horizontal ceiling 4056 of the duct help channel the incoming air in desired directions. The airflow is driven by the blower. The blower also drives downstream airflow indicated by arrows 4140A-D (FIG. 41). Air exits the device via the outtake vent holes.

The non-stick tape may include a loop of Teflon™ or other material generally regarded as a non-stick material and completes the boundaries for the incoming air flow. The tape forms a loop and may be referred to as a non-stick tape loop. The tape may be, for example, a polymer tape or include a polymer material. Other appropriate materials may instead or additionally be used. Despite use of a tape material generally regarded as non-stick, very small particles such as pollen grains will stick to the surface of the non-stick tape loop as a result of Van der Waals forces. In alternate embodiments, the non-stick tape need not be a loop, but rather can be tape supplied reel to reel for one-time use. In other specific embodiments, the non-stick tape may be cleaned after use so that it can be reused one or more times.

As shown in the example of FIG. 40, at least a portion of the non-stick tape loop is positioned so that it is near airflow 4050A-D. For example, the at least a portion of the non-stick tape may be below the airflow or may be within or at least partially obstruct the airflow. In a specific embodiment, at least a portion of the airflow path passes over opening 4036 of the duct through which at least a portion of the non-stick tape loop is exposed. Due to the force of gravity, particles such as pollen grains (e.g., pollen grains 4060A-C) will settle out of the sampled ambient air in the airflow and stick to the surface of the non-stick tape loop that is exposed through the duct opening. When desired, the non-stick tape loop is moved in the direction indicated by arrow 4045. This illustrates the use of gravity to separate particles such as pollen grains from ambient air.

As discussed above, the loop is supported by rollers 4039A and 4039B. Roller 4039D is controlled by a stepper motor (not shown) and is coated with a sticky adhesive. Via roller 4039D, the stepper motor controls motion 4045 of the non-stick tape loop. Roller 4039C is provided with a mechanism to vibrate at acoustic or ultrasonic frequencies. This results in at least some of the captured particles such as pollen grains (e.g., pollen grains 4065A-B) being released under the influence of gravity. Due to its sticky adhesive, roller 4039D will remove any pollen and other particles on the surface of the non-stick tape loop that were not removed by vibration of roller 4039C.

Referring now to FIG. 41, vibration released pollen grains 4065A and 4065B fall and land upon adhesive coated tape 4120. As discussed, the adhesive coated tape is supplied by reel 4115A, is guided by rollers 4110A-B and is collected by reel 4115B. The motion of the adhesive-coated tape is driven via take-up reel 4115B by a second stepper motor (not shown). Motion 4125 of the adhesive-coated tape moves captured particles such as pollen grain 4065B', within a field of view 4145 of the optical microscope.

The optimal or desired field of view will depend on the application. In a specific embodiment, a field of view of width is about 1 millimeter (mm). In a specific embodiment, a width of the field of view is substantially narrower or less than the width of the pollen (or particle) collection region of non-stick tape 4042, advantageously greatly increasing the concentration of particles in the field of view. For example, a ratio between the field of view of width and the width of the pollen collection region of the non-stick tape may be about 1:2. In other specific embodiments, the ratio may be about 1:1.2, 1:1.4, 1:1.6, 1:1.8, 1:2.2, 1:2.4, 1:2.6, 1:2.8, 1:3, 1:4, 1:5, 1:6, 1:7, 1:8, 1:9, or 1:10.

In a specific embodiment, the exposed horizontal surface area of the non-stick tape loop is about 7 centimeters (cm)×2 cm=14 cm^2. For smaller particles (e.g., pollen or mold spores) of diameters of about 20 microns, the particle settling rate is roughly 1 cm/second, resulting in an air sampling rate of about 14 cm^2×1 cm/sec=14 cm^3/sec=840 cm^3/minute=0.84 liter/minute. This is the case if the blower establishes sufficient airflow so that air reaching the most interior portions of the non-stick tape loop are depositing particles, e.g., pollen grains. This is about one order of magnitude less than a typical breathing rate of a resting human. In some applications this may be sufficient. In other applications, it will be desirable to increase the ambient-air sampling rate. Particularly for indoor applications, the relatively fast settling of particles such as pollen out of air and the relatively low "wind velocity" indoors may well vary by orders of magnitude from one location to another within a home. Intelligent placement of one or more particle monitors within a home may well provide a desired order of magnitude increase in effective pollen monitor sensitivity.

In many cases, the two stepper motors may be at rest most of the time. For example, the non-stick tape loop may be at rest for one minute while particles such as pollen grains (e.g., pollen grains 4060A-C) accumulate on its surface. After a sufficient such period, the stepper motor driving roller 4039D may be activated and ultrasonic release roller 4039C may be excited for sufficient time to transfer all or at least some of the collected pollen grains onto the adhesive-coated tape (see, e.g., falling grains 4065A-B). Roller 4039D cleans the non-stick polymer loop material in preparation for a subsequent sampling period. For example, the roller may include a brush to clean the non-stick tape of particles. The operation of the stepper motors may be triggered based upon a pre-determined schedule or frequency. Instead or additionally, the operation of the stepper motors may be triggered based on some other event.

As a result, particles such as pollen sampled from 840 cm^3 of ambient air is deposited in a narrow strip below ultrasonic release roller 4039C and onto the adhesive-coated tape. Ideally the width of these deposited particles (e.g., pollen grains) is no wider than the field of view of camera image sensor 4143 (FIG. 41) so that all particles (e.g., pollen) collected may be imaged. After the transfer of particles from the non-stick tape loop to the adhesive-coated tape is complete, then via reel 4115B the second stepper motor may move the collected pollen through the field of view of the microscope system.

In a specific embodiment, an operation of the collection device is triggered upon a determination that the user has suffered an allergic reaction. In this specific embodiment, the collection device receives a request (such as from the analysis server or allergic reaction monitoring device with sensor) to sample the ambient air. Upon receiving the request, the blower is activated. Particles within the airflow suction or vacuum caused by the blower are deposited via gravity through the bottom opening of the duct and onto the waiting non-stick tape of the first conveyor assembly.

Once the period of collection is complete, the non-stick tape may be advanced. When the portion of the non-stick tape having the collected particles reaches roller 4039C, the advancement of the non-stick tape may be paused or slowed while roller 4039C is vibrated to shake the collected particles off and onto the adhesive-coated tape of the second conveyor assembly. Once the shaking is complete, the adhesive-coated tape may be advanced.

When the portion of the adhesive-coated tape having the collected particles reaches or is within the field of view of the camera sensor, the advancement may be paused or slowed so that the camera sensor can capture an image of the particles stuck to the adhesive-coated tape. The captured images are then analyzed to identify the captured particles (e.g., pollen).

A combination of factors including pollen optical properties (e.g., blue to red ratio) and pollen grain size may be evaluated using an algorithm of the system to identify pollen. Pollen grain size can be determined according to scattered light intensity. For example, pollen such as ragweed, Japanese cedar, walnut, and kamogaya may be identified based on their respective blue/red fluorescent light ratios and pollen grain sizes. Any competent technique or combinations of techniques may be used to automatically recognize or identify the collected pollen. Some examples of identification techniques include image processing, non-image optical properties such scattering and fluorescence, and others.

The operations of the system, such as the collection operations, can be logged and time-stamped. The time-stamping allows for a cross-referencing of the collected particles (and particle identifications) with the time of the allergic reaction. As one of skill in the art will recognize, the rate at which the conveyor assemblies advance their respective tapes can be synchronized or sequenced with the camera sensor so that the tape portion having the collected particles is properly positioned with respect to the camera sensor for imaging.

In a specific embodiment, the adhesive coated tape having the collected physical particles is archived and retained for possible future retrieval. The reel of tape can be removed from the particle collection device and sent to a laboratory for archiving and further analysis.

In a specific embodiment, a number of the intake vents or orifices and the incoming air can be as little as a single orifice or there can be multiple intake vents (e.g., two or more). In an embodiment having a single intake vent, it can be desirable (but not required) for the device to have a mechanism for aligning itself in the direction of incoming wind in order to sample as many particles flying through the air as possible or desired. For example, the mechanism may include wind vane to identify a direction of the wind. Once the direction of the wind is identified, the collection device may then automatically rotate or orient itself so that the intake orifice is aligned with the incoming wind.

In another specific embodiment, there are many or multiple intake orifices to cover the entire circumference (or a portion of the circumference) of the cylindrical device. In this specific embodiment, aligning the device in the direction of oncoming wind may not be necessary.

FIG. 40 shows a dimension D16 that indicates a diameter of the collection device and a dimension H16 that indicates a height of the collection device. In a specific embodiment, the diameter is about 100 mm and the height is about 150 mm. It should be appreciated, however, that these dimensions may vary greatly depending upon factors such as desired performance criteria, manufacturing cost targets, expected service life, expected operating environment, and many others. A cylindrical shape is preferred but not required. For example, in addition to providing an aesthetic appearance, a cylindrical monitor with a vertical axis of rotation can rotate to sample pollen from different orientations without risk of mechanical interference. Any shape or form factor may be suitable as long as there is an intake orifice in any orientation where the particles can be separated and analyzed as described by the mechanisms and techniques herein.

The air intake orifices or duct can be made to vibrate and oscillate to various frequencies such that particles that may have attached to the orifice or duct surface can separate from the surface and the air intake pull force will pull these in towards the surface of the non-stick tape.

In a specific embodiment, the adhesive-coated tape is transparent. This allows the optical imaging elements to be placed on a backside of the tape (i.e., a side of the tape opposite a side having the collected particles) and still be able to capture an image of the particles for analysis. There can be many different configurations of the particle collection device to meet desired form factors, performance, and so forth. Thus, it should be appreciated that the mechanical schematics shown in FIGS. 40-43 are merely an example of one particular implementation of the collection device.

In other implementations, other similar and equivalent elements and functions may be used or substituted in place of what is shown. For example, roller 4039C of the first conveyor assembly is shown as being aligned along a centerline or longitudinal axis of the collection device. The roller, however, may be offset from the centerline or closer one side of the collection device than an opposite side of the collection device so long as the adhesive-coated tape of the second conveyor assembly is suitably located to collect the particles which fall from the non-stick tape of the first conveyor assembly.

As another example, a vibration mechanism has been described as a technique to transfer particles from the non-stick tape of the first conveyor assembly to the adhesive-coated tape of the second conveyor assembly. In another specific embodiment, however, a vacuum, brush, or both may instead or additionally be used to transfer the particles. As another example, the optical imaging elements (e.g., camera sensor) may be configured to capture images of the particles while the particles remain on the non-stick tape.

In another specific embodiment, there is a particle monitoring device that creates an electromagnetic field to push and pull particles as desired by having a roller made of an electrically conductive material serving as one electrode and a second electrode (not shown) placed directly underneath adhesive coated tape, and voltage applied across the two electrodes. This provides an electric field where particles proximate to roller move on to adhesive coated tape. It can also function in an alternating field where the roller and adhesive coated tape change polarity allowing the use of non-conductive materials for non-stick tape loop and adhesive coated tape as well as forcing particles that are negative or positive be expelled from the roller onto the adhesive coated tape.

Figure 44:
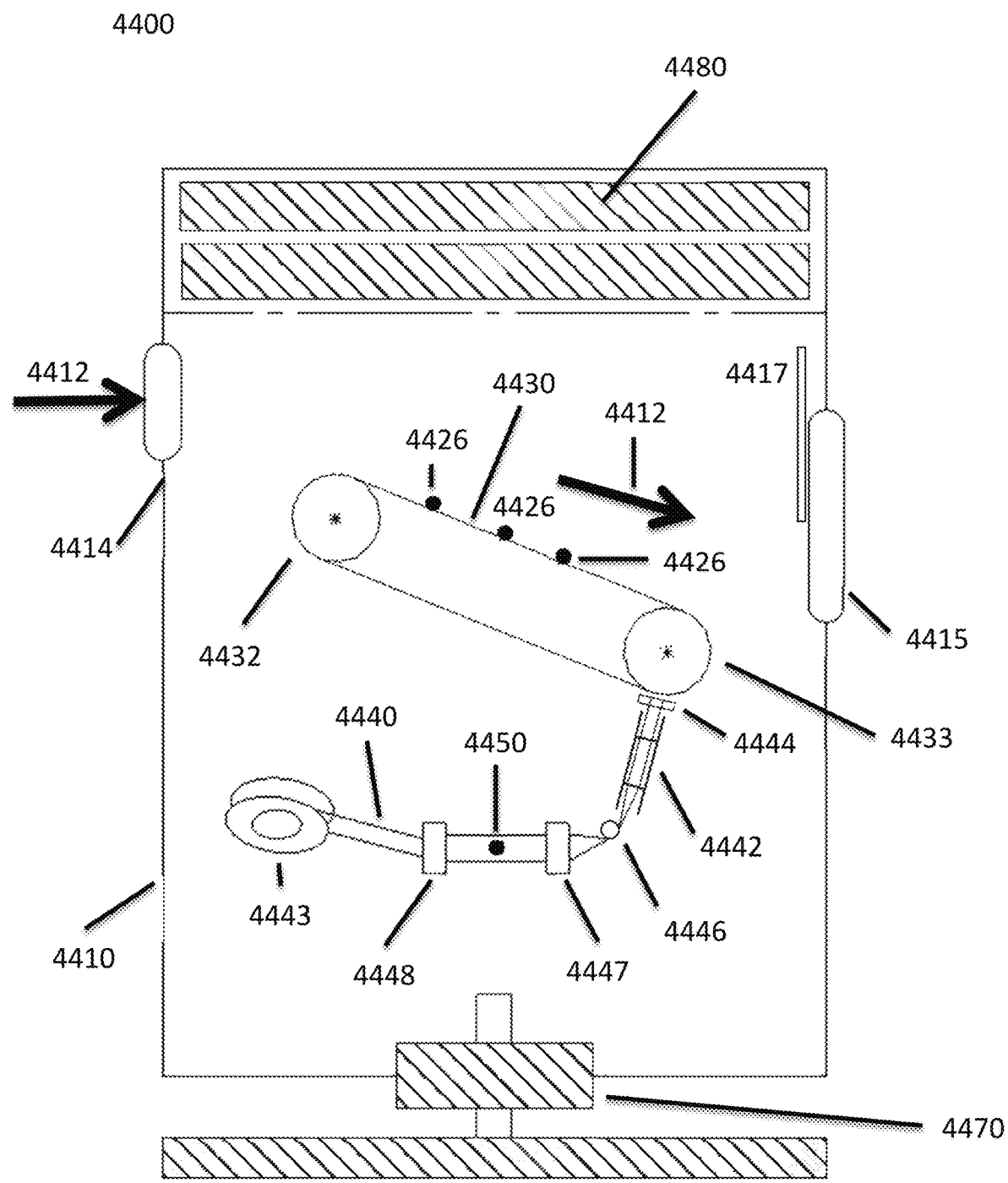
FIG. 44 shows a side view of a particle monitor according to another specific embodiment.
Figure 45:
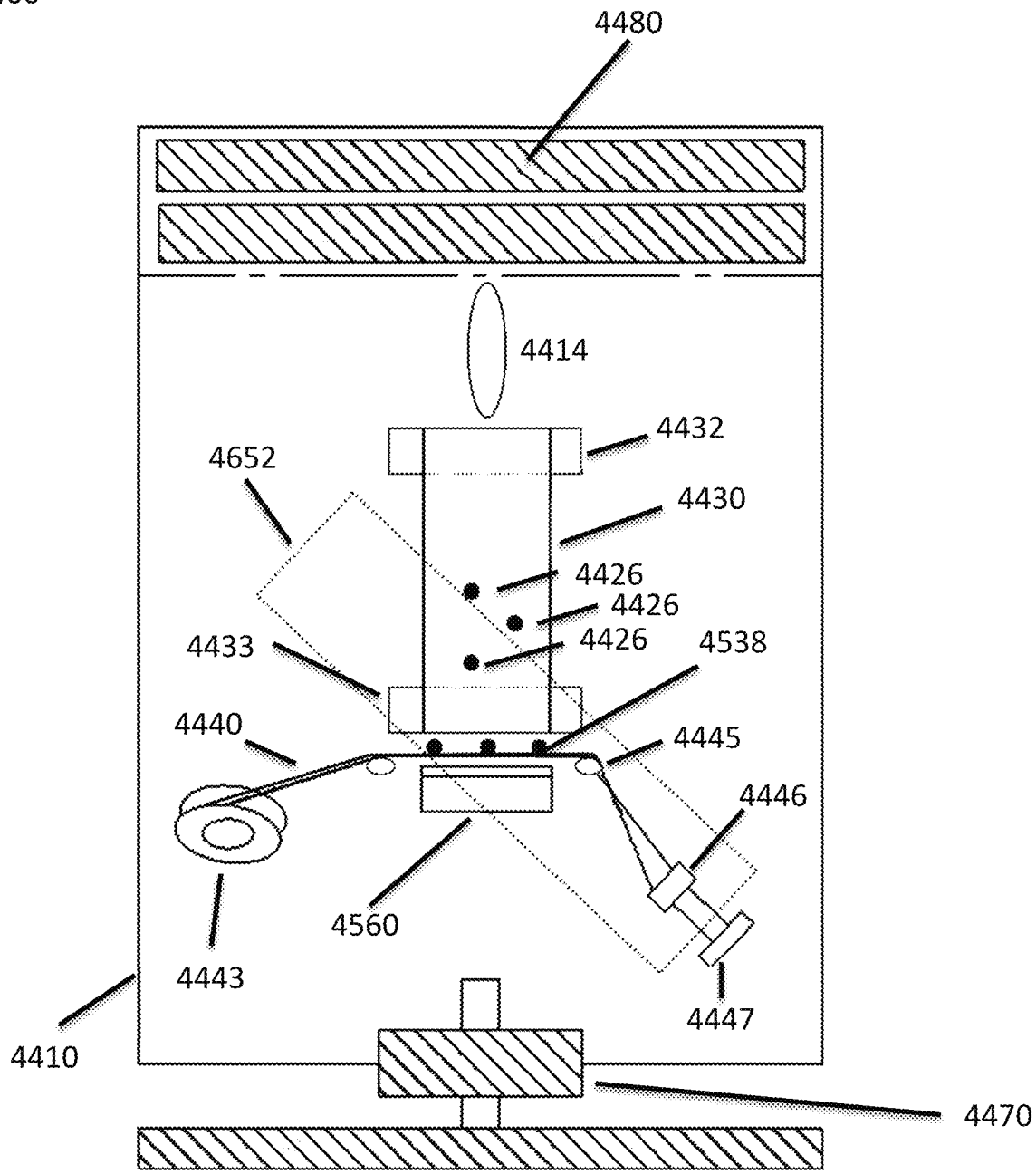
FIG. 45 shows another side view of the particle monitor shown in FIG. 44.
Figure 46:
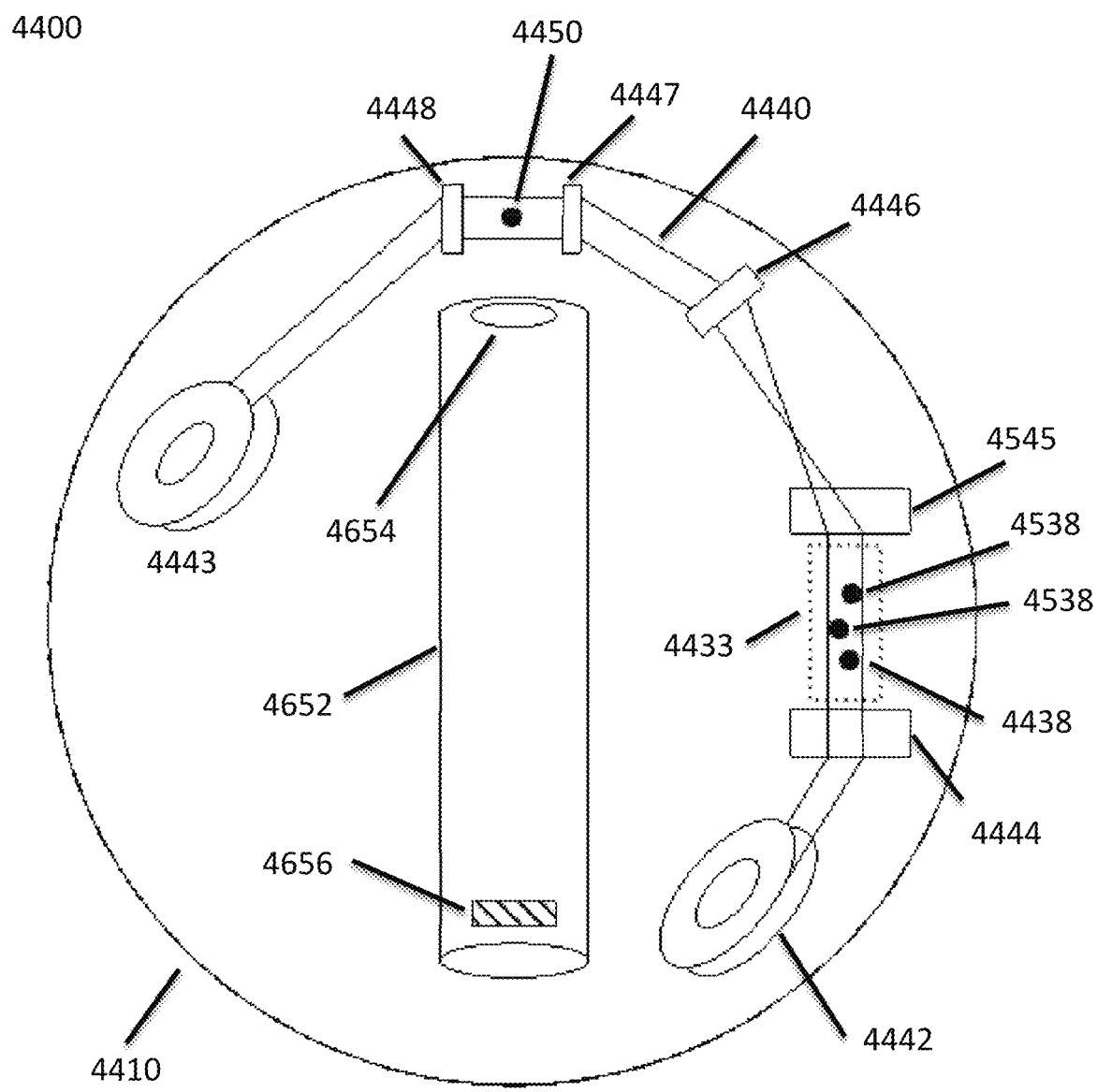
FIG. 46 shows a top cross-section view of the particle monitor shown in FIG. 44.
Figure 47:
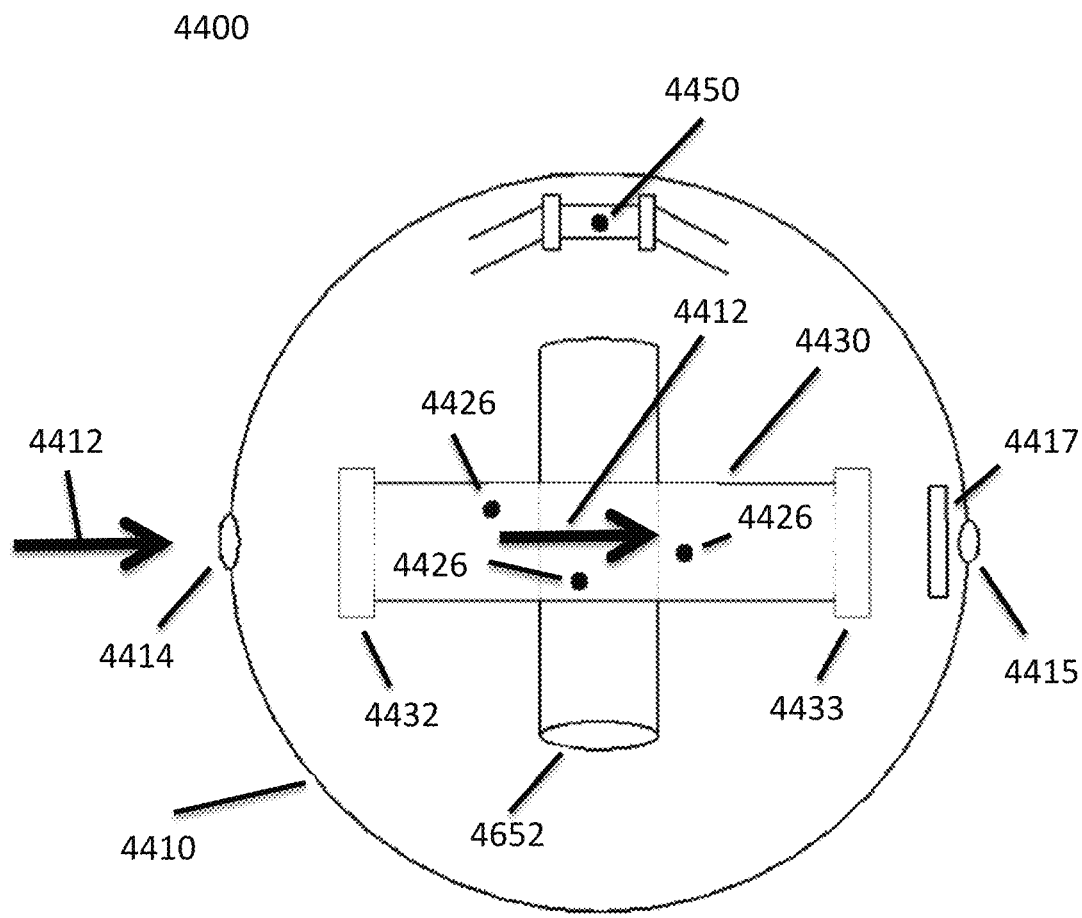
FIG. 47 shows another top cross-section view of the particle monitor shown in FIG. 44.

Some of the above variations of the particle monitoring system are illustrated by device 4400 of FIGS. 44-47. While device 4005 of FIGS. 40-43 is well-suited for environments with gentle airflow such as indoors, device 4400 of FIGS. 44-47 is well-suited for outdoor use where it may be desirable to collect particles such as pollen when there is ambient airflow due to the wind. FIG. 44 illustrates the case that input vent hole 4414 is a single hole. A swivel mount 4470 is schematically illustrated which allows device 4400 to rotate so that the input vent hole 4414 faces the wind. The orientation mechanism may be passive such as due to vanes (not shown) on the exterior of enclosure 4410 or active such as a stepper motor incorporated into swivel mount 4470 that is controlled by battery powered electronics 4480 that is provided with wind direction data.

While device 4400 may include a fan or blower to control airflow, FIG. 44 illustrates the case that airflow is wind powered. Wind pressure will naturally drive airflow 4412 from input vent hole 4414 to output vent hole 4415. An electronically controlled shutter 4417 in front of output vent hole 4415 may partially cover or extend over the output vent hole 4415 and thus control the rate of airflow 4412. Input vent hole 4414 may likewise be provided with a similar shutter (not shown). A horizontal ceiling and vertical walls (not shown) similar to items 4056 and 4053 of device 4005 of FIG. 40 confine airflow 4412 as desired. Due to the influence of gravity, particles 4426, such as pollen grains, will settle out of the sampled ambient air and stick to non-stick tape loop 4430 that wraps around rollers 4432 and 4433. Up to this point the particle collection mechanism of device 4400 is very similar to that of device 4005.

Device 4400 also makes use of an adhesive coated tape 4440 similar to adhesive coated tape 4120 of device 4005. However, device 4400 illustrates a very different mechanism for transferring collected particles from non-stick tape to adhesive coated tape. When plunger 4560 (FIG. 45) is activated (by a mechanism that is not shown), it presses the adhesive surface of adhesive coated tape 4440 (FIG. 44) against non-stick tape loop 4430 so that particles on non-stick tape loop 4430 make contact with the adhesive of adhesive coated tape 4440. When plunger 4560 (FIG. 45) is retracted, the adhesive coated tape 4440 (FIG. 44) moves away from the non-stick tape loop 4430 bringing particles 4538 (FIG. 45) with it. During this particle transfer cycle, the non-stick tape loop 4430 (FIG. 44) is supported by roller 4433 in a way that provides for a contact area between the two tapes whose width is matched with the width of the field of view of an optical microscope system comprised of an optical column 4652 (FIG. 46), an objective lens array 4654 and a camera-image sensor 4656.

As illustrated in FIG. 44, the non-stick tape loop 4430 is guided by rollers 4432 and 4433, one of which is controlled by a first stepper motor. Additional rollers may be added if desired. Optionally roller 4433 may be provided with a vibration mechanism that is not strong enough to overcome Van der Waals forces for particles of interest such as pollen, but still sufficient to shake off larger particles, objects that are not of interest, or both. A further mechanism (not shown) for removing larger particles that are not of interest is to include a snow-plow like blade above the non-stick tape loop as it passes around roller 4433 and before it reaches the transfer region.

FIG. 44 also illustrates the option for the particle collection surface of non-stick tape loop 4430 to deviate from a perfectly horizontal orientation. This enables the region of transfer between the two tapes to be tilted as shown and as necessary to fit all components of the device 4400 within enclosure 4410. The needs of mechanically packing all components within enclosure 4410 also motivates a more involved path for adhesive coated tape 4440 relative to the path in device 4005 for adhesive coated tape 4120. Other than being tilted, supply reel 4442 and roller 4444 is similar to reel 4115A and roller 4115B of device 4005. After collecting particles 4538 (FIG. 45), adhesive coated tape 4440 passes over roller 4445 and twists to roller 4446 so that the adhesive faces outward and downward by the time it reaches roller 4447. Between roller 4447 and 4448, the adhesive coated tape 4440 moves through the field of view of the optical system so that particles such as particle 4450 (FIG. 47) may be imaged. After leaving roller 4448, the adhesive coated tape is collected by reel 4443. Reel 4443 is driven by a second stepper motor when desired so that the adhesive coated tape 4440 moves in the direction indicated by the arrow 241.

The optical microscope system comprised of optical column 4652, objective lens array 4654, and camera-image sensor 4656 is similar to the optical system of device 4005 of FIGS. 40-43 with two exceptions. First, the axis of the optical column is now tilted rather than being vertical as illustrated in FIG. 41 for optical column 4130. Secondly, imaged particle 4450, and the adhesive that holds it, is on the backside of the adhesive coated tape 4440 from the perspective of the optical system. This requires adhesive coated tape 4440 to be transparent.

Figure 48:
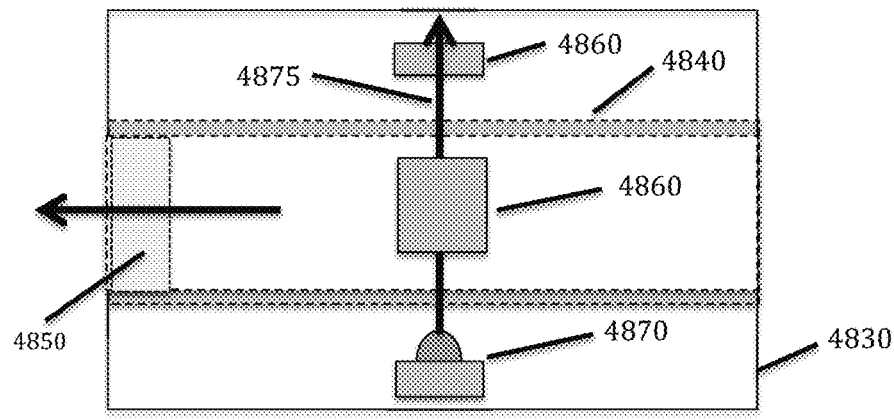
FIG. 48 shows a top view of a particle monitor that does not include a camera sensor according to another specific embodiment.
Figure 49:
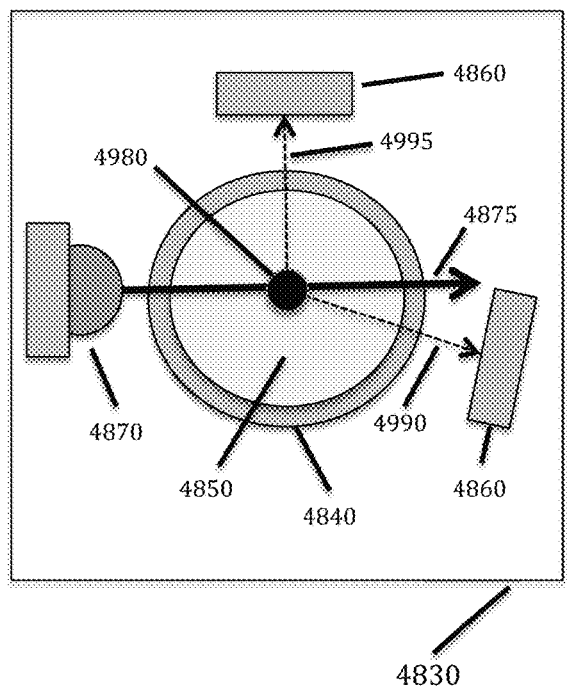
FIG. 49 shows a front view of the particle monitor shown in FIG. 48.

Many variations of hardware designs may support the steps of the flow chart of FIG. 33. FIGS. 48 and 49 correspond to a contrasting example. FIGS. 48 and 49 are two perspectives on the same example device. As we will see in the next example, the steps of the above flow chart are not limited to automated pollen detection systems based on RGB camera sensors.

FIGS. 48 and 49 illustrate a pollen monitoring system without an RGB camera sensor. FIG. 48 shows a top view of the pollen monitoring system. FIG. 49 shows a front view of the pollen monitoring system. In a specific embodiment, the pollen monitoring system may be referred to as a tree pollen monitor or simplified pollen monitor.

The pollen monitoring system of FIGS. 48-49 may be installed in the branches of a tree that is known to produce allergenic pollen and is known to do so with a seasonal timing representative of similar trees in the neighborhood. When such a monitoring system of FIGS. 48-49 detects a high concentration of particulates, it may be sufficient to simply distinguish between pollen and other particulates and assume that when pollen is detected in high concentration in the appropriate season, the detected pollen is from the tree the monitoring system is mounted in.

As discussed above, tree leaves are green because their chlorophyll strongly absorbs red and blue light; see the chlorophyll-a absorption spectrum shown in FIG. 22. In particular, see the strong red absorption peak 2210 around 665 nm wavelength. The width of this absorption peak is rather similar to the width of quantum dot emission spectra. This implies that the tree leaves will be particularly effective in shading sunshine and ambient light within the spectrum of a 665 nm red quantum-dot light source. The pollen monitor of FIGS. 48-49 takes advantage of this observation.

FIGS. 48-49 illustrate a pollen monitoring system within an opaque enclosure 4830 through which passes a tube 4840 that is transparent for red around 665 nm and largely opaque at other wavelengths. Such a system is only susceptible to ambient light for a narrow range of wavelengths around 665 nm. When installed within the shade of green tree leaves, ambient light in that spectral range is greatly reduced due to chlorophyll light absorption. Furthermore, standard ambient light subtraction techniques based on capturing optical signals with both the illumination source 4870 on and off may further suppress ambient light backgrounds. All of this allows for a relatively open airflow system (driven by fan 4850 at downstream end of tube) that beneficially minimizes or reduces surfaces for pollen to stick to before reaching the optical detection zone.

The sensors 4860 shown in FIG. 48-49 may simply be phototransistors. With sensors 4860, scattering is observed at both small angle and large angle (90 degree) scattering. Light beam 4875 (FIG. 49) from LED 4870 (e.g., quantum dot LED) may pass through a pollen grain 4980 resulting in light scattered at a small angle and detected by a sensor 4860, as in light beam 4990, as well as light scattered at a large angle and detected by a sensor 4860 as in light beam 4995. Smaller particles tend to have a larger ratio of large angle scattering light to small angle scattered light. Larger and more dense particles tend to scatter more light. This provides means to estimate particle size and density; in some applications this may be enough to discriminate between tree pollen and other particulates.

The pollen monitoring system of FIGS. 48-49 may be modified to take advantage of the second chlorophyll-a absorption peak 2220 (FIG. 22) for blue light around 465 nm. As with 665 nm red peak 2210, tree leaves are very black for such light around 465 nm thus suppressing sunshine and other ambient light in this spectral range. Instead of just one illumination source 4870 to provide narrow spectrum 665 nm red light via quantum dots, a second quantum-dot LED illumination source (not shown) at 465 nm may also be provided. In this case the tube 4840 that is generally opaque would be designed to be transparent around both 465 nm and 665 nm. Optionally, the scattered red and blue light is detected by separate sets of sensors. Alternatively the same sensors detect both light colors. A further design option is to allow tube 4840 to be transparent at all wavelengths (e.g. a simple plastic or glass tube) while locally providing each sensor with an optical filter that passes only the desired narrow range of wavelengths around 665 nm and/or 465 nm. With both red and blue light scattering information, color characteristics of pollen is obtained and discriminating power is increased.

The flow chart of FIG. 33 also applies to the simplified pollen monitoring system of FIGS. 48-49. Ambient air is sampled and transported down the tube 4840 to an illumination zone associated with sensors 4860 and illumination source 4870; this illustrates steps 3310 and 3320 in FIG. 33. The 665 nm red LED 4870 may be selected by a local microprocessor program, the LED then excited and signals from the sensors collected per steps 3330, 3340 and 3350. Optionally, if the hardware is designed to also support 465 nm blue illumination and signal capture, steps 3330, 3340 and 3350 may be repeated for the blue illumination. While not shown, a local microprocessor may analyze the collected optical data (step 3360) and transmit it wirelessly to the cloud (step 3370). Devices such as that illustrated in FIGS. 48-49 may be employed to provide the cloud with up-to-date information on blooming trees dispersing allergenic pollen, so that such information is available to the cloud at step 3455 of the flow of FIG. 34.

In some pollen monitoring system designs, it may be possible to well isolate the optical detection zone from ambient light. In other particular monitoring systems it may be desirable to minimize or reduce the obstacles in the path of airflow carrying pollen or other particulates to the optical detection zone. While this may improve pollen and particular transport and sampling efficiency, such a design approach makes it more difficult to eliminate ambient light backgrounds at the optical detection zone. As a general observation for such situations, the narrow spectrum feature of quantum-dot illumination sources provides an ambient-light suppression benefit in allowing narrow-spectrum filters to be placed between sources of ambient light and optical sensors of a pollen monitoring system. The system of FIGS. 48-49 is just one specific example of this general principle.

In alternate embodiments, different approaches are taken for air intake hardware 220 (FIG. 2) and particle capture hardware 222. While in some of the embodiments described above, turbulent airflow was preferred in the particle capture zone, in alternate embodiments, gravitational settling of particles out of air are may be used to separate samples particles from the ambient air that contained them. Optionally, the air intake system may be designed to provide laminar flow in the particle capture region. Furthermore, in alternate embodiments, the adhesive-coated tape may be replaced with tape not having an adhesive coating, as Van der Waals forces become proportionally larger as particle sizes become smaller, may be sufficient to fix particles of interest to the tape during transport from the particle capture region to the particle inspection region. In yet further embodiments, particles may first be captured on tape without adhesive, then transferred to adhesive coated tape, in a way that concentrates the density per unit area of captures particles. Furthermore, in alternate embodiments, particle-capture tape is not used and instead particles are captures on slides or disks that are optionally coated with adhesive.

Figure 50:
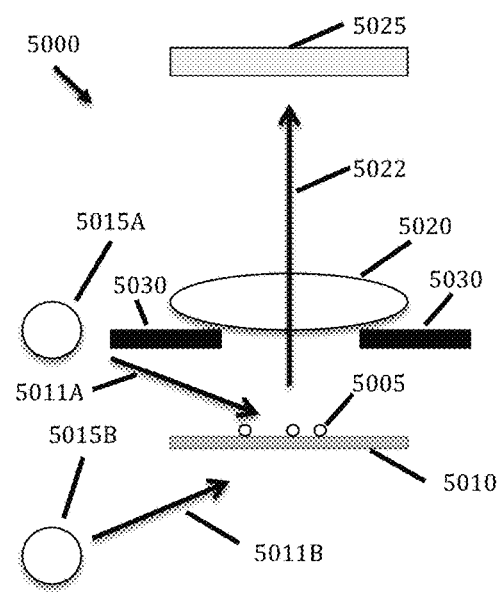
FIG. 50 shows a side view of a particle monitor according to another specific embodiment.

In a specific embodiment, a pollen or digital optical imaging system includes an image sensor, a lens assembly and an illumination source. FIG. 50 shows an example of a pollen imaging system 5000. Pollen grains 5005 may be on the surface of a slide 5010 and illuminated 5011A-B by a light sources 5015A-B from above the slide, below the slide, or both. A lens or lens assembly 5020 images 5022 the pollen grains on an image sensor 5025. The thick black horizontal line segments 5030 represent an iris defining the aperture of the lens assembly.

In a specific embodiment, the image sensors that can be used have been developed and are mass-produced for digital cameras including digital cameras built into smart phones. These silicon chip devices provide mega-pixel RGB images at relatively low cost. A representative pixel pitch for such sensor chips is 1.4 microns. These powerful and low-cost image sensors can be used for the purpose of enabling low-cost automated pollen monitoring systems.

Because pollen grains are typically only tens of microns in diameter, in a specific embodiment, it is generally preferable for the imaging system to provide some magnification between the sampled pollen and its image at the imaging sensor. For example, to provide a factor of four magnification, the distance from the lens assembly to the image sensor for the image sensor may be about four times the distance from the lens assembly to the sampled pollen. As image resolution approaching the wavelength of light is desired, diffraction limited optics with relatively large apertures may be needed. This makes the problem of chromatic aberrations more difficult.

Referring to FIG. 50, in a specific embodiment, a pollen imaging system incorporates quantum dots into the light sources schematically represented by circles 5015A-B. In one approach, a film containing quantum dots is placed between the pollen sample and a light source such as an LED, thus sharpening the spectral peaks relative to the original light source. In another approach, the quantum dots are electrically excited to directly create light with desired spectral properties; for example, quantum dots may be the light emitting elements within an LED.

FIG. 51 shows a block diagram of mobile device 135 according to another specific embodiment. In this specific embodiment, the mobile device includes a wearable computer 5105. In the example shown in FIG. 51, the wearable computer includes a strap 5110 having a fastening mechanism such as a buckle or Velcro. The wearable computer can be strapped to the user's wrist or chest. The wearable computer can include hardware and software similar to that shown in FIG. 7 and described in the discussion accompanying FIG. 7. For example, the wearable computer may include a display 5110, apps including a particle identification app 5115 with an allergic reaction detection subsystem, processor, memory, and one or more sensors (e.g., microphone, accelerometer, or gyroscope). The wearable computer may be implemented as a smartwatch. The wearable computer may be implemented as a wearable tracking or monitoring device that may or may not include a display. One of ordinary skill in the art would recognize other variations, modifications, and alternatives.

FIG. 52 shows an example of a kit 5252 including a set of replaceable particle collection cartridges 5253. In the example shown in FIG. 52, the kit includes a box and a tray inside the box. The tray holds particle collection cartridge A, particle collection cartridge B, an instruction manual 5256, and a mailing envelope 2757.

The kit may or may not include the particle collection device. The instruction manual provides instructions for inserting a cartridge into particle monitor device 150 according to one embodiment, removing the cartridge from the particle monitor device, and (if desired) mailing a used cartridge to a laboratory for further analysis of the particles that may have been trapped. The mailing envelope can be a pre-paid and pre-addressed mailing envelop that the user can use to mail the cartridge. In an embodiment, the user purchases a particle monitor device and can separately purchase additional blank or empty collection cartridges as desired. In the example shown in FIG. 52, two collection cartridges are shown. It should be appreciated, however, that a kit may include any number of cartridges such as one, two, three, four, five, or more than five cartridges.

Figure 53:
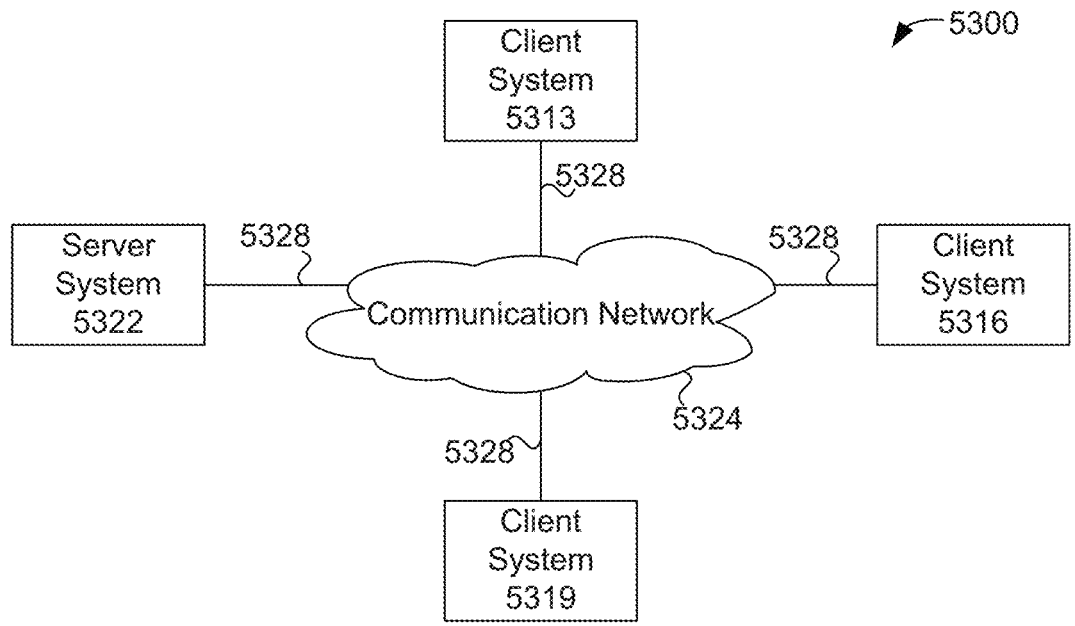
FIG. 53 shows a block diagram of a client-server system and network in which an embodiment of the system may be implemented.

FIG. 53 is a simplified block diagram of a distributed computer network 5300 that may be used in a specific embodiment of a system for airborne particle collection, detection and recognition. Computer network 5300 includes a number of client systems 5313, 5316, and 5319, and a server system 5322 coupled to a communication network 5324 via a plurality of communication links 5328. There may be any number of clients and servers in a system. Communication network 5324 provides a mechanism for allowing the various components of distributed network 5300 to communicate and exchange information with each other.

Communication network 5324 may itself be comprised of many interconnected computer systems and communication links. Communication links 5328 may be hardwire links, optical links, satellite or other wireless communications links, wave propagation links, or any other mechanisms for communication of information. Various communication protocols may be used to facilitate communication between the various systems shown in FIG. 53. These communication protocols may include TCP/IP, HTTP protocols, wireless application protocol (WAP), vendor-specific protocols, customized protocols, and others. While in one embodiment, communication network 5324 is the Internet, in other embodiments, communication network 5324 may be any suitable communication network including a local area network (LAN), a wide area network (WAN), a wireless network, an intranet, a private network, a public network, a switched network, and combinations of these, and the like.

Distributed computer network 5300 in FIG. 53 is merely illustrative of an embodiment and is not intended to limit the scope of the embodiment as recited in the claims. One of ordinary skill in the art would recognize other variations, modifications, and alternatives. For example, more than one server system 5322 may be connected to communication network 5324. As another example, a number of client systems 5313, 5316, and 5319 may be coupled to communication network 5324 via an access provider (not shown) or via some other server system.

Client systems 5313, 5316, and 5319 enable users to access and query information stored by server system 5322. In a specific embodiment, a "Web browser" application executing on a client system enables users to select, access, retrieve, or query information stored by server system 5322. Examples of web browsers include the Internet Explorer® and Edge® browser programs provided by Microsoft® Corporation, Chrome® browser provided by Google®, and the Firefox® browser provided by Mozilla® Foundation, and others. In another specific embodiment, an iOS App or an Android® App on a client tablet enables users to select, access, retrieve, or query information stored by server system 5322. Access to the system can be through a mobile application program or app that is separate from a browser.

A computer-implemented or computer-executable version of the system may be embodied using, stored on, or associated with computer-readable medium or non-transitory computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present system may be stored or reside in RAM or cache memory, or on a mass storage device. The source, executable code, or both of the software may also be stored or reside on a mass storage device (e.g., hard disk, magnetic disk, tape, or CD-ROM). As a further example, code may be transmitted via wires, radio waves, or through a network such as the Internet.

A client computer can be a smartphone, smartwatch, tablet computer, laptop, wearable device or computer (e.g., Google Glass), body-borne computer, or desktop.

Figure 54:
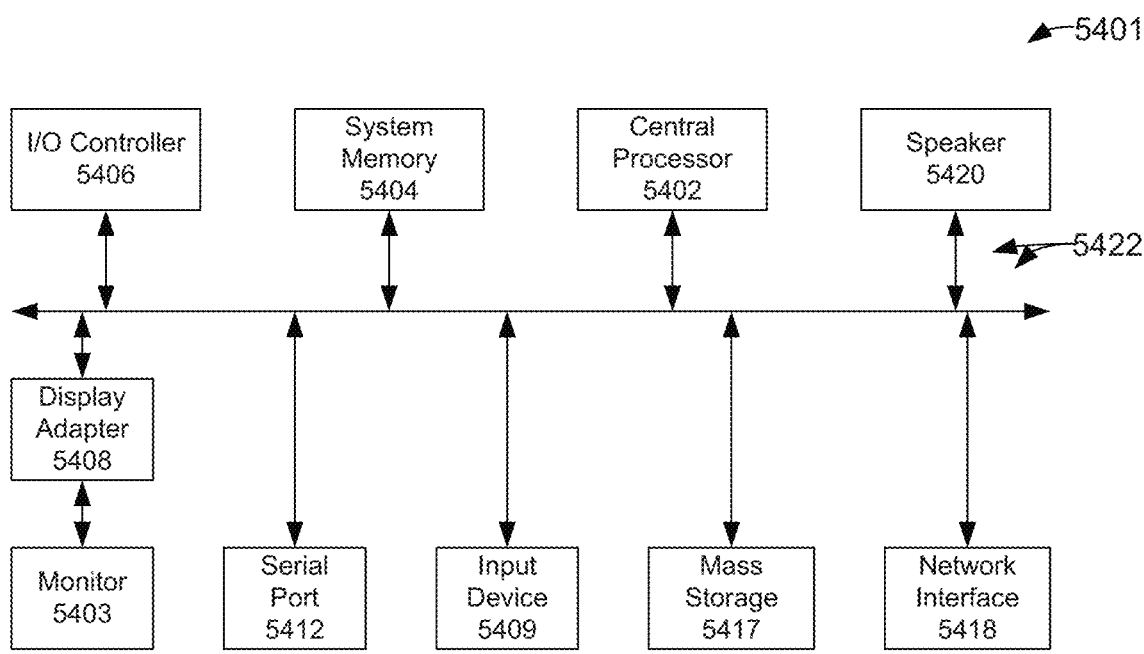
FIG. 54 shows a system block diagram of a client or server computer system shown in FIG. 53.

FIG. 54 shows a system block diagram of computer system 5401. Computer system 5401 includes monitor 5403, input device (e.g., keyboard, microphone, or camera) 5409, and mass storage devices 5417. Computer system 5401 further includes subsystems such as central processor 5402, system memory 5404, input/output (I/O) controller 5406, display adapter 5408, serial or universal serial bus (USB) port 5412, network interface 5418, and speaker 5420. In an embodiment, a computer system includes additional or fewer subsystems. For example, a computer system could include more than one processor 5402 (i.e., a multiprocessor system) or a system may include a cache memory.

Arrows such as 5422 represent the system bus architecture of computer system 5401. However, these arrows are illustrative of any interconnection scheme serving to link the subsystems. For example, speaker 5420 could be connected to the other subsystems through a port or have an internal direct connection to central processor 5402. The processor may include multiple processors or a multicore processor, which may permit parallel processing of information. Computer system 5401 shown in FIG. 54 is but an example of a suitable computer system. Other configurations of subsystems suitable for use will be readily apparent to one of ordinary skill in the art.

Computer software products may be written in any of various suitable programming languages, such as C, C++, C#, Pascal, Fortran, Perl, Matlab® (from MathWorks), SAS, SPSS, JavaScript®, AJAX, Java®, SQL, and XQuery (a query language that is designed to process data from XML files or any data source that can be viewed as XML, HTML, or both). The computer software product may be an independent application with data input and data display modules. Alternatively, the computer software products may be classes that may be instantiated as distributed objects. The computer software products may also be component software such as Java Beans® (from Oracle Corporation) or Enterprise Java Beans® (EJB from Oracle Corporation). In a specific embodiment, a computer program product is provided that stores instructions such as computer code to program a computer to perform any of the processes or techniques described.

An operating system for the system may be iOS by Apple®, Inc., Android by Google®, one of the Microsoft Windows® family of operating systems (e.g., Windows NT®, Windows 2000®, Windows XP®, Windows XP® x64 Edition, Windows Vista®, Windows 7®, Windows CE®, Windows Mobile®, Windows 8, Windows 10), Linux, HP-UX, UNIX, Sun OS®, Solaris®, Mac OS X®, Alpha OS®, AIX, IRIX32, or IRIX64. Other operating systems may be used. Microsoft Windows® is a trademark of Microsoft® Corporation.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of the system using a wireless network using a protocol such as Wi-Fi (IEEE standards 802.11, 802.11a, 802.11b, 802.11e, 802.11g, 802.11i, and 802.11n, just to name a few examples). For example, signals from a computer may be transferred, at least in part, wirelessly to components or other computers.

In an embodiment, with a Web browser executing on a computer workstation system, a user accesses a system on the World Wide Web (WWW) through a network such as the Internet. The Web browser is used to download web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

In the discussion above, for simplicity of presentation, the allergen or particulate is often referred to as "pollen." It should be appreciated, however, that the above-described methods are not limited to the detection and characterization of pollen. Aspects and principles of the system can be applied to detecting and identifying any type of particulate including allergenic particulates, non-allergenic particulates, or both. Aspects and principles of the system can be applied to a microscopic particle imaging system. Aspects and principles of the system can be applied to an allergen detection system that may or may not rely on a camera-sensor based imaging system.

A specific application of the system is the monitoring of allergens. Aspects and principles of the system, however, may be applied to other fields including the study of pollen, i.e., palynology. The collection and analysis of pollen plays an important role in a number of scientific and applied fields including agriculture and ecology including climate change effects on seasonal timing and geographical distribution of airborne pollens. Previous approaches to capturing and analyzing airborne pollen often involved a great deal of manual work and expensive and bulky equipment. The system including the pollen collection devices described herein, however, provides an automated, compact, and cost-effective approach to collecting and analyzing pollen.

It should be appreciated that while some embodiments described above discuss allergic reactions to pollen, one of skill in the art will recognize that aspects and principles of the system may be applied to other airborne allergens as well as airborne pathogens of interest to agricultural applications. A specific application of the system is for the identification or discrimination of airborne particles. It should be appreciated, however, that aspects and principles of the system may be applied to non-airborne particles.

It should also be appreciated that for embodiments using illumination sources based on quantum dots, there are corresponding embodiments with alternate illumination sources not based on quantum dots. In many cases quantum-dot based embodiments will be most or very cost-effective, but this is not necessarily the case for all scenarios. For example, the fluorescent quantum dots of the embodiments illustrated by FIGS. 18, 23 and 26 may substituted by other fluorescent materials that are not quantum dots. The LEDs with electronically excited quantum dots of FIGS. 24 and 25 may in alternate embodiments be replaced with LEDs using light-emitting semi-conductor materials with band gaps tune via other means such as composition, or be replaced with tunable laser sources, or broad spectrum light sources followed by color filters. The airborne biological particle monitor engineer may utilize quantum dots to the extent that their use reduces the cost or enhances the performance of the device.

In a specific embodiment, aspects and principles of the system may be applied to monitoring a vineyard for agriculture diseases or agricultural pathogens. In this specific embodiment, the collection cartridge can be hand-held by a user for a manual collection of particles that may have collected on a surface of a leaf or grape of a grape vine. In this specific embodiment, a method may include holding a collection cartridge, the collection cartridge comprising an adhesive coated tape and a slot through which a portion of the tape is exposed; positioning the slot to face an object; pressing the cartridge against the object to bring the portion of the tape into contact with a surface of the object, thereby transferring particles on the surface to the tape; and inserting the cartridge into a particle monitor for an analysis of the particles. The object may include a leaf, such as a grape leaf, or a grape such as from a grape vine. The types of particles of interest to identify may include small pests, insects, bacterium, mildew, mold spores, or combinations of these.

Examples of airborne mildews of interest to vineyards may include *Eutypa lata, Botrytis,* and *Cladospora* mold among others. Detection of such mold may be transmitted to a mobile app on the vineyard owner's mobile device. The system can provide counts, trends, and predictive data and analytics displayed via a web application or mobile application. The application allows for customizing alerts for efficient vineyard management operation. The system can provide up-to-the minute information on invasive, disease causing molds, pollens, and weeds. Winds, for example, can carry disease spores for miles. It is desirable to distinguish between harmful and benign molds for successful fungicide operations. The system allows for 24/7 monitoring and is much more cost-effective than microscopic inspection and visual spot checks. Early disease detection and control can increase yield and product quality.

In an embodiment, systems and techniques are provided for the detection and classification of airborne particles (e.g., pollens, molds, dander, heavy smoke (ash) particles, sand/silica, asbestos, and many others). Systems and techniques are provided for detecting and counting particles having a size (e.g., a longest dimension) from about 1 um to about 1500 um. In an embodiment, a minimum particle resolution is about 0.3 um. In another embodiment, a minimum particle resolution is about 0.1 um). In an embodiment, a light-based methodology includes five different measurement techniques including deep neural network machine learning and advanced algorithms to extract unique particle signatures leading to classification. A media cartridge is provided that captures particles for physical record archiving, future studies, advanced studies in a laboratory, or combinations of these. An analysis may include particle feature extraction, vector extraction, executing a classifier algorithm, particle classifications, and aggregating the information into a results file, or combinations of these. The results file may be transmitted to a user's mobile device for display. Particle detection techniques may include morphology (e.g., shape and size), UV fluorescence (e.g., NADH & NAD excitation), colorimetry (e.g., color parameters), topography (e.g., height and texture), internal structure, or combinations of these.

In a specific embodiment, a method for a tiered-analysis of a particle detected at a pollen monitor includes analyzing the particle at the airborne biological particle monitor to obtain a work-in-progress classification of the particle, after the analyzing to obtain the work-in-progress classification, transmitting information about the particle across a network to a server, remote from the pollen monitor, for further analysis, receiving a request from the server for additional information about the particle, and transmitting the additional information from the pollen monitor to the server to allow a final classification of the particle.

In another specific embodiment, a method includes receiving at a server from a pollen monitor a request to classify a particle detected at the pollen monitor, requesting additional information from the pollen monitor, receiving the additional information, determining that the additional information is insufficient to make a final classification of the particle, based on the determination, requesting a manual review of information associated with the particle, receiving the final classification of the particle, and upon the receiving the final classification of the particle, generating an alert.

In another specific embodiment, a particle monitor does not include quantum dots. In this specific embodiment, an airborne biological particle monitoring device that collects particles floating in air includes a processor, a camera sensor configured to be controlled by the processor, an illumination source configured to be controlled by the processor, and logic, where the camera sensor captures an image of the particles when the collected particles are illuminated by the illumination source, and where the processor processes the logic to analyze the image to identify the collected particles.

In another specific embodiment, there is an apparatus for monitoring airborne particulates such as allergens, molds, etc. said apparatus comprising: a means for drawing in ambient air to be monitored; a medium onto which particulate matter from the air is deposited and held; a computer or other processing system; one or more illumination systems for illumination the medium onto which the particles are deposited; one or more optical systems for relaying an image of the particles on the medium to an image sensor; software or firmware in the processor to capture images from the image sensor and analyze the particle images; a means for exposing areas of the medium for a controlled period of time and for putting known areas of the medium in the field(s)-of-view of the optical system(s); and a means for communicating the results of the analyses to other computing systems for presentation or further analysis.

In the description above and throughout, numerous specific details are set forth in order to provide a thorough understanding of an embodiment of this disclosure. It will be evident, however, to one of ordinary skill in the art, that an embodiment may be practiced without these specific details. In other instances, well-known structures and devices are shown in block diagram form to facilitate explanation. The description of the preferred embodiments is not intended to limit the scope of the claims appended hereto. Further, in the methods disclosed herein, various steps are disclosed illustrating some of the functions of an embodiment. These steps are merely examples, and are not meant to be limiting in any way. Other steps and functions may be contemplated without departing from this disclosure or the scope of an embodiment. Other embodiments include systems and non-volatile media products that execute, embody or store processes that implement the methods described above.

What is claimed is:

1. An airborne particle collection system comprising:
  a monitoring device comprising:
    a housing comprising an air-intake slot, the air-intake slot having a length and a width, wherein the length is greater than the width;
    a motor; and
    a camera sensor including a lens; and a removable collection cartridge comprising:
  a cartridge housing, separate from the housing of the monitoring device;
  an adhesive-coated tape contained within the cartridge housing;
  a supply reel;
  an uptake reel; and
  a tape guide comprising a first segment, and a second segment,
  wherein the first segment defines a particle intake zone, proximate to the air-intake slot when the removable collection cartridge has been inserted into the housing of the monitoring device, and through which the adhesive-coated tape is exposed to capture airborne particles passing through the air-intake slot,
  wherein the second segment defines an inspection zone at which the airborne particles captured at the particle intake zone are transported for optical imaging,
  wherein the motor moves the airborne particles captured by the adhesive-coated tape from the particle intake zone to the inspection zone, and
  wherein the first and second segments are at an angle to each other and the adhesive-coated tape extends from the supply reel, across the first and second segments of the tape guide, and to the uptake reel.

2. The airborne particle collection system of claim 1 wherein the monitoring device comprises:
  a processor; and
  a power source, wherein the processor processes information and, based on the processing, directs the motor to move the adhesive-coated tape.

3. The airborne particle collection system of claim 2 wherein the monitoring device comprises:
  a network interface controller, coupled to the processor, that receives a plurality of instructions from a remote server over a network, wherein the plurality of instructions comprise:
    a first instruction to move the collection media; and
    a second instruction to transmit to the remote server an image of the airborne particles that have been captured on the collection media.

4. The airborne particle collection system of claim 1 wherein the monitoring device is powered by an AC power source.

5. The airborne particle collection system of claim 1 comprising:
  a light emitting diode (LED) illumination source;
  an ultra-violet (UV) LED illumination source; and
  an imaging processing module, each of the camera sensor, variable lens, LED illumination source, UV LED illumination source, and imaging processing module being contained within the housing of the monitoring device, and
  wherein the LED and UV LED illumination sources illuminate the airborne particles collected onto the collection media for imaging by the camera sensor, the variable lens comprises a lens with an electronically controlled focal length, and the imaging processing module comprises logic to recognize particles of interest imaged by the camera sensor.

6. The airborne particle collection system of claim 1 comprising:
  a light emitting diode (LED) illumination source;
  an ultra-violet (UV) LED illumination source; and
  an imaging processing module, each of the camera sensor, variable lens, LED illumination source, and UV LED illumination source being contained within the housing of the monitoring device,
  wherein the imaging processing module is at a cloud server, remote from the monitoring device, and
  wherein the LED and UV LED illumination sources illuminate the airborne particles collected onto the collection media for imaging by the camera sensor, the variable lens comprises a lens with an electronically controlled focal length, and the imaging processing module comprises logic to recognize particles of interest imaged by the camera sensor.

7. The airborne particle collection system of claim 1 wherein the monitoring device comprises a processor, wherein the processor receives information from a remote server.

8. The airborne particle collection system of claim 5 wherein the camera sensor comprises a red-green-blue (RGB) camera sensor.

9. The airborne particle collection system of claim 1 wherein the monitoring device comprises a processor identifying a collected particle as being of a particular type of pollen by transmitting to a remote server a geographical location of the monitoring device, and obtaining from the remote server context information based on the geographical location of the monitoring device.

10. The airborne particle collection system of claim 9 wherein the context information comprises at least one of pollen types known to be currently blooming at the geographical location, wind patterns at the geographical location, or a listing of pollen types detected by other monitoring devices.

11. The airborne particle collection system of claim 1 comprising a processor identifying a collected particle as being of a particular type of spore by transmitting to a remote server a geographical location of monitoring device, and obtaining from the remote server context information based on the geographical location of the monitoring device.

12. The airborne particle collection system of claim 1 comprising a processor identifying a collected particle as being of a particular type of biological particle by transmitting to a remote server a geographical location of the monitoring device, and obtaining from the remote server context information based on the geographical location of the monitoring device.

13. The airborne particle collection system of claim 1 wherein the air-intake slot of the housing aligns with the particle intake zone.

14. The airborne particle collection system of claim 1 wherein the air-intake slot of the housing faces the particle intake zone.

15. The airborne particle collection system of claim 1 wherein the first and second segments of the tape guide are orthogonal to each other.

16. The airborne particle collection system of claim 15 wherein the tape guide comprises a third segment, the third segment extending between an end of the first segment and an end of the second segment.

17. The airborne particle collection system of claim 1 wherein airflow in the particle intake zone is turbulent.

18. The airborne particle collection system of claim 5 wherein the LED illumination source comprises quantum-dots.

19. An airborne particle collection system comprising:
a monitoring device comprising:
- a housing comprising an air-intake slot, the air-intake slot having a length and a width, wherein the length is greater than the width, and the width varies in a funnel-like fashion from a first value to a second value, less than the first value, through a thickness of the housing;
- a motor;
- a camera sensor;
- one or more illumination sources to identify airborne particles based on optical image characteristics, the one or more illumination sources comprising at least one illumination source emitting visible light; and
- a base; and a removable collection cartridge comprising:
- a cartridge housing separate from the housing of the monitoring device;
- an adhesive-coated tape contained within the cartridge housing; and
- a tape guide comprising a first segment defining a particle intake zone, and a second segment defining an inspection zone, the first and second segments being orthogonal to each other,
- wherein the adhesive-coated tape extends across the first and second segments of the tape guide, and the first and second segments of the tape guide are at an angle to each other, and
- wherein the removable collection cartridge when inserted into the monitoring device, the camera sensor, and the one or more illumination sources, are positioned such that the camera sensor and the one or more illumination sources are above the removable collection cartridge, the camera sensor and the one or more illumination sources thereby being further from the base than the removable collection cartridge.

20. An airborne particle collection system comprising:
a monitoring device comprising:
- a housing comprising an air-intake slot;
- a motor;
- a camera sensor;
- one or more illumination sources to identify airborne particles based on optical image characteristics; and
- a base; and a removable collection cartridge comprising:
- a cartridge housing separate from the housing of the monitoring device;
- an adhesive-coated tape contained within the cartridge housing; and
- a tape guide comprising a first segment defining a particle intake zone, and a second segment defining an inspection zone,
- wherein the adhesive-coated tape extends across the first and second segments of the tape guide, and the first and second segments of the tape guide are orthogonal to each other,
- wherein the removable collection cartridge when inserted into the monitoring device, the camera sensor, and the one or more illumination sources, are positioned such that the camera sensor and the one or more illumination sources are above the removable collection cartridge, the camera sensor and the one or more illumination sources thereby being further from the base than the removable collection cartridge, and
- wherein the air-intake slot faces the particle intake zone and comprises a length, and a width, wherein the length is greater than the width, and the width varies in a funnel-like fashion from a first value to a second value, less than the first value, through a thickness of the housing to provide airflow in the particle intake zone that is turbulent.

* * * * *